US009915647B2

(12) United States Patent
Yadava et al.

(10) Patent No.: US 9,915,647 B2
(45) Date of Patent: Mar. 13, 2018

(54) METHODS, COMPOSITIONS AND KITS FOR ASSAYING MITOCHONDRIAL FUNCTION

(71) Applicants: Baystate Medical Center, Inc., Springfield, MA (US); UNIVERSITY OF MASSACHUSETTS, Boston, MA (US)

(72) Inventors: Nagendra Yadava, Longmeadow, MA (US); Alejandro Pablo Heuck, Amherst, MA (US); Chul Kim, West Springfield, MA (US)

(73) Assignees: BAYSTATE MEDICAL CENTER, INC., Springfield, MA (US); UNIVERSITY OF MASSACHUSETTS, Boston, MA (US)

(*) Notice: Subject to any disclaimer, the term of this patent is extended or adjusted under 35 U.S.C. 154(b) by 0 days.

(21) Appl. No.: 15/087,521

(22) Filed: Mar. 31, 2016

(65) Prior Publication Data
US 2016/0282337 A1 Sep. 29, 2016

Related U.S. Application Data

(63) Continuation of application No. 13/441,418, filed on Apr. 6, 2012, now abandoned.

(60) Provisional application No. 61/473,730, filed on Apr. 8, 2011.

(51) Int. Cl.
C12Q 1/02 (2006.01)
G01N 33/50 (2006.01)
C07K 14/33 (2006.01)

(52) U.S. Cl.
CPC ......... *G01N 33/5079* (2013.01); *C07K 14/33* (2013.01); *G01N 33/5005* (2013.01); *G01N 2333/33* (2013.01)

(58) Field of Classification Search
CPC .................................................. C12Q 1/025
See application file for complete search history.

(56) References Cited

U.S. PATENT DOCUMENTS

| 7,666,656 | B2 | 2/2010 | Sun | |
|---|---|---|---|---|
| 2005/0048596 | A1 | 3/2005 | Kristian et al. | |
| 2005/0159349 | A1 | 7/2005 | Soto et al. | |
| 2005/0170329 | A1 | 8/2005 | Murphy et al. | |
| 2006/0204435 | A1* | 9/2006 | Stuart | A61K 49/0002 424/1.49 |
| 2006/0252114 | A1 | 11/2006 | Raychaudhuri et al. | |
| 2007/0026090 | A1 | 2/2007 | Tirosh et al. | |
| 2007/0274917 | A1 | 2/2007 | Lange et al. | |
| 2008/0095794 | A1 | 4/2008 | Sun et al. | |
| 2008/0112964 | A1 | 5/2008 | Kirkham et al. | |

(Continued)

OTHER PUBLICATIONS

Fujikawa et al., "A sensitive, simple assay of mitochondrial ATP synthesis of cultured mammalian cells suitable for high-throughput analysis," Biochemical and Biophysical Research Communications 401:538-543, Sep. 27, 2010.*

(Continued)

Primary Examiner — Rosanne Kosson
(74) Attorney, Agent, or Firm — James S. Keddie; Bozicevic, Field & Francis, LLP

(57) ABSTRACT

The invention provides methods, compositions, devices, and kits relating to the use of cholesterol-dependent cytolysins (e.g., PFOs) for measuring intracellular mitochondrial activity.

15 Claims, 55 Drawing Sheets

(56) References Cited

U.S. PATENT DOCUMENTS

| | | |
|---|---|---|
| 2008/0132948 A1 | 6/2008 | Surti et al. |
| 2008/0175827 A1 | 7/2008 | Fissore et al. |
| 2009/0285846 A1 | 11/2009 | Tweten |
| 2010/0009895 A1 | 1/2010 | Lindhorst et al. |
| 2010/0233781 A1 | 9/2010 | Bangera et al. |
| 2015/0198585 A1 | 7/2015 | Nagendra |

OTHER PUBLICATIONS

Rood, "Virulence genes of Clostridium perfringens," Annual Reviews in Microbiology 52:333-360, 1998.*
Annis et al., Bax forms multispanning monomers that oligomerize to permeabilize membranes luring apoptosis. EMBO J. Jun. 15, 2005;24(12):2096-103.
Braun et al., Pneumolysin causes neuronal cell death through mitochondrial damage, Infect Immun. Sep. 2007;75(9):4245-54.
Barrientos, In vivo and in organella assessment of OXPHOS activities. Methods. Apr. 2002;26(4):307-16.
Bet Arbet et al., Chronic systemic pesticide exposure reproduces features of Parkinson's disease. Nat Neurosci. Dec. 2000;3(12):1301-6.
Carroll et al., Bovine complex I is a complex of 45 different subunits. J Bioi Chern. Oct. 27, 2006;281(43):32724-7.
Carlson, et al. "Selective inhibition by preparations of *Streptococcal* filtrates of the oxidative metabolism of mitochondria procured from rabbit myocardium", J Exptl. Med. 104:577-587, 1956.
Compton et al., Mitochondrial dysfunction impairs tumor suppressor p53 expression/function. J Bioi Chern. Jun. 10, 2011;286(23):20297-312.
Coskun et al., Systemic mitochondrial dysfunction and the etiology of Alzheimer's disease and down syndrome dementia. J Alzheimers Dis. 2010.
Cuezv A et al., The tumor suppressor function of mitochondria: translation into the clinics. Biochim Biophys Acta. Dec. 2009;1792(12):1145-58.
Distelmaier et al., Mitochondrial complex I deficiency: from organelle dysfunction to clinical disease. Brain. Apr. 2009;132(Pt 4):833-42.
Div Akaruni et al., Thiazolidinediones are acute, specific inhibitors of the mitochondrial pyruvate carrier. Proc Natl Acad Sci US A. Apr. 2, 2013;110(14):5422-7.
Ferrick et al., Advances in measuring cellular bioenergetics using extracellular flux. Drug Discov Today. Mar. 2008;I3(5-6):268-74.
Flanagan et al., Cholesterol exposure at the membrane surface is necessary and sufficient to trigger perfringolysin 0 binding. Biochemistry. May 12, 2009;48(18):3977-87.
Gasparre et al., Disruptive mitochondrial DNA mutations in complex I subunits are markers of oncocytic phenotype in thyroid tumors. Proc Natl Acad Sci US A May 22, 2007;104(21):9001-6. Epub May 15, 2009.
Gerencser et al., Quantitative microplate-based respirometry with correction for oxygen diffusion. Anal Chem. Aug. 15, 2009;81(16):6868-78.
Gostimska YA et al., In situ assay of the intramitochondrial enzymes: use of alamethicin for permeabilization of mitochondria. Anal Biochem. Feb. 1, 2003;313(1):46-52.
Heuck et al., Assembly and topography of the prepore complex in cholesterol-dependent cytolysins. J Bioi Chern. Aug. 15, 2003;278(33):31218-25.
Heuck et al., Conformational changes that effect oligomerization and initiate pore formation are triggered throughout perfringolysin 0 upon binding to cholesterol. J.Biol.Chem. Aug. 3, 2007;282(31):22629-37.
Heuck et al., The cholesterol-dependent cytolysin family of gram-positive bacterial toxins. Subcell Biochem. 2010;51:551-77, chapter 20.
Hotze et al., Monomer-monomer interactions drive the prepore to pore conversion of a beta-barrel-forming cholesterol-dependent cytolysin. J Bioi Chern. Mar. 29, 2002;277(13): 11597-605.

Hutter et al., High-resolution respirometry—a modem tool in aging research. Exp Gerontol. Jan. 2006;41(1): 103-9. Epub Nov. 23, 2005. Erratum in: Exp Gerontol. Apr. 2006;41(4):457.
Jacob et al., Membrane cell permeabilization with saponin and multiparametric analysis by flow cytometry. Cytometry. 1991;12(6):550-8.
Jekabsons et al., In situ respiration and bioenergetic status of mitochondria in primary cerebellar granule neuronal cultures exposed continuously to glutamate. J Bioi Chem. Jul. 30, 2004;279(31):32989-3000.
Koene et al., Mitochondrial medicine: entering the era of treatment. J Intern Med. Feb. 2009;265(2):193-209.
Koene et al., Mouse models for nuclear DNA-encoded mitochondrial complex I deficiency. J Inherit Metab Dis. Apr. 2011;34(2):293-307.
Kuznetsov et al., Analysis of mitochondrial function in situ in permeabilized muscle fibers, tissues and cells. Nat Protoc. 2008;3(6):965-76.
Lange et al., Plasma membranes contain half the phospholipid and 90% of the cholesterol and sphingomyelin in cultured human fibroblasts. J Bioi Chem. Mar. 5, 1989;264(7):3786-93.
Li et al., Transient oxidative stress damages mitochondrial machinery inducing persistent beta-cell dysfunction. J Bioi Chem. Aug. 28, 2009;284(35):23602-12.
Loeffen et al., Isolated complex I deficiency in children: clinical, biochemical and genetic aspects. Hum Mutat. 2000;15(2): 123-34.
Lu et al., Implications of mitochondrial DNA mutations and mitochondrial dysfunction in tumorigenesis. Cell Res. Jul. 2009;19(7):802-15.
McKenzie et al., Assembly factors of human mitochondrial complex I and their defects in disease. IUBMB Life. Jul. 2010;62(7):497-502.
Merglen et al., Glucose sensitivity and metabolism-secretion coupling studied during two-year continuous culture in INS-IE insulinoma cells. Endocrinology. Feb. 2004;145(2):667-78.
Mihajlovic et al., Antimicrobial peptides in toroidal and cylindrical pores. Biochim Biophys Acta. Aug. 2010;1798 (8):1485-93.
Moe et al., Phospholipid hydrolysis caused by Clostridium perfringens a-toxin facilitates the targeting of perfringolysin to membrane bilayers. Biochemistry. Nov. 9, 2010;49(44):9498-507. Supporting Information.
Montoya et al., Beta-barrel membrane protein folding and structure viewed through the lens of alpha-hemolysin. Biochim Biophys Acta. Jan. 10, 2003;1609(1):19-27.
Martinez, et al., Regulation of Mitochondrial Cholesterol Metabolism, In: Subcellular Biochemistry. Bittman (Ed.). 1997. Chapter 8:205-234.
Nakamura et al., Contribution of tryptophan residues to the structural changes in perfringolysin during interaction with liposomal membranes. J Biochem. Jun. 1998;123(6): 1145-55.
Nicholls et al., Mitochondria and neuronal survival. Physiol Rev. Jan. 2000;80(1):315-60.
O'Riordan et al., Analysis of intracellular oxygen and metabolic responses of mammalian cells by time-resolved fluorometry. Anal Chem. Dec. 15, 2007;79(24):9414-9.
Pagel-Langenickel et al., The role of mitochondria in the pathophysiology of skeletal muscle insulin resistance. Endocr Rev. Feb. 2010;31(1):25-51.
Scheffler et al., Molecular genetics of the mammalian NADH-ubiquinone oxidoreductase. J Bioenerg Biomembr. Jun. 2001;33(3):243-50.
Shepard et al., Identification of a membrane-spanning domain of the thiol-activated pore-forming toxin Clostridium perfringens perfringolysin 0: an alpha-helical to beta-sheet transition identified by fluorescence spectroscopy. Biochemistry. Oct. 13, 1998;37(41):14563-74.
Shepard, et al., The mechanism of pore assembly for a cholesterol-dependent cytolysin: formation of a large prepore complex precedes the insertion of the transmembrane 13-hairpins, Biochemistry 39:10284-10293, 2000.
Stumvoll et al., Type 2 diabetes: principles of pathogenesis and therapy. Lancet. Apr. 9-15, 2005;365(9467): 1333-46.

(56) References Cited

OTHER PUBLICATIONS

Tucker et al., Recent advances in the genetics of mitochondrial encephalopathies. Curr Neurol Neurosci Rep. Jul. 2010;10(4):277-85.
Vali et al., Integrating glutathione metabolism and mitochondrial dysfunction with implications for Parkinson's disease: a dynamic model. Neuroscience. Nov. 23, 2007;149(4):917-30.
Wallace, A mitochondrial paradigm of metabolic and degenerative diseases, aging, and cancer: a dawn for evolutionary medicine. Annu Rev Genet. 2005;39:359-407.
Weng et al., Functional role of J domain of cysteine string protein in Ca2+-dependent secretion from acinar cells. Am J Physiol Gastrointest Liver Physiol. May 2009;296(5):G1030-9.
Wu et al., Multiparameter metabolic analysis reveals a close link between attenuated mitochondrial bioenergetic function and enhanced glycolysis dependency in human tumor cells. Am J Physiol Cell Physiol. Jan. 2007;292(I): C125-36.
Yadava et al., Impaired mitochondrial metabolism and mammary carcinogenesis. J Mammary Gland Bioi Neoplasia. Mar. 2013;18(1):75-87.
Yadava et al., Species-specific and mutant MWFE proteins. Their effect on the assembly of a functional mammalian mitochondrial complex I. J Bioi Chem. Jun. 14, 2002;277(24):21221-30.
Yadava et al., Unique features of pancreatic beta-cell mitochondrial NADH metabolism. FASEB. 2011 ;25:720.11. Abstract only.
Kim, Cytotoxicity of vibrio vulnificus cytolysin on pulmonary endothelial cells. Experimental Molecular Medicine. Jun. 1997;29(2): 117-121.
Kwon et al., Vibrio vulnificus cytolysin induces superoxide anion-initiated apoptotic signaling pathway in human ECV304 cells. J Bioi Chern. Dec. 14, 2001;276(50):47518-23.
Popova et al., Anthrolysin 0 and fermentation products mediate the toxicity of Bacillus anthracis to lung epithelial ells under microaerobic conditions. FEMS Immunol Med Microbial. Feb. 2011;61(1): 15-27.
Weissmann et al., Studies On Lysosomes. III. The Effects of Streptolysins 0 and S On The Release Of Acid Hydrolases From A Granular Fraction Of Rabbit Liver. J Exp Med. 1963.
Genbank Submission; NCBI, Accession No. AAR97343; Ward et al.; May 10, 2005.
Genbank Submission; NCBI, Accession No. ABE66337; Ni et al.; Apr. 6, 2006.
Genbank Submission; NCBI, Accession No. ABK58695; Jefferies et al.; Dec. 29, 2006.
Genbank Submission; NCBI, Accession No. AB02I366; Jefferies et al.; Jan. 11, 2010.
Genbank Submission; NCBI, Accession No. ABY46062; Lapidus et al.; Nov. 21, 2011.
Genbank Submission; NCBI, Accession No. ACI76900; Leopold et al.; Jun. 8, 2009.
Genbank Submission; NCBI, Accession No. BAD7779I; Kimoto et al.; Jan. 17, 2012.
Genbank Submission; NCBI, Accession No. BAE72438; Watanabe et al.; Jan. 7, 2006.
Genbank Submission; NCBI, Accession No. DQ838568; Papageorgiou et al.; Aug. 9, 2006.
Genbank Submission; NCBI, Accession No. EU522488; Gelber et al.; May 19, 2008.
Genbank Submission; NCBI, Accession No. NP 268546; Ferretti et al.; Sep. 10, 2012.
Genbank Submission; NCBI, Accession No. NP 561079; Shimizu et al.; Aug. 31, 2012.
Genbank Submission; NCBI, Accession No. NP 782466; Bruggemann et al.; Jan. 20, 2012.
Genbank Submission; NCBI, Accession No. P23564; Geoffroy et al.; Nov. 28, 2012.
Genbank Submission; NCBI, Accession No. P31830; Haas et al.; Nov. 28, 2012.
Genbank Submission; NCBI, Accession No. Q53957; Okomura et al.; Nov. 28, 2012.
Genbank Submission; NCBI, Accession No. U84782; Billington et al.; Nov. 16, 2001.
Genbank Submission; NCBI, Accession No. YP 001699692; Hu et al.; Jan. 26, 2012.
Genbank Submission; NCBI, Accession No. YP 001886995; Brinkac et al.; Jan. 27, 2012.
Genbank Submission; NCBI, Accession No. YP 001921918; Brinkac et al.; Jan. 27, 2012.
Genbank Submission; NCBI, Accession No. YP 002369889; Dodson et al.; Sep. 27, 2012.
Genbank Submission; NCBI, Accession No. YP _002770211; Hosoyama et al.; Oct. 28, 2011.
Genbank Submission; NCBI, Accession No. YP 037419; Han et al.; Sep. 27, 2012.
Genbank Submission; NCBI, Accession No. YP _878174; Bettegowda et al.; Sep. 27, 2012.
Genbank Submission; NCBI, Accession No. ZP 02620972; Dec. 9, 2010.
Genbank Submission; NCBI, Accession No. ZP 02950902; Nov. 9, 2010.
Genbank Submission; NCBI, Accession No. ZP 03017964; Nov. 9, 2010.
International Search Report and Written Opinion for PCT/US2012/032540, dated Oct. 1, 2012, 6 pages.
International Preliminary Report on Patentability, PCT/US2012/032540, dated Oct. 17, 2013, 8 pages.
Extended European Search Report for European Patent Application EP12819805.8, dated Mar. 12, 2015, 6 pages.
Partial Supplementary European Search Report for European Patent Application EP12819805.8, dated Nov. 18, 2014, 6 pages.
Result 1, alignment of SEQ ID N0:1 with SEQ ID N0:2 of Sun et al., U.S. Pat. No. 7,666,656 82, from a search in the issued patents protein database, performed on Feb. 13, 2015 in the parent U.S. Appl. No. 13/441,418.
Keiser et al., "Studies on Lysosomes, IV. Solubilization of Enzymes during Mitochondrial Swelling and Disruption of Lysosomes by Streptolysin S and Other Hemolytic Agents" The Journal of Cell Biology—vol. 22, Jul. 1, 1964, pp. 101-113.

* cited by examiner

SEQUENCE LISTING

<160> NUMBER OF SEQ ID NOS: 12

<210> SEQ ID NO 1
<211> LENGTH: 500
<212> TYPE: PRT
<213> ORGANISM: Clostridium perfringens

<400> SEQUENCE: 1

Met Ile Arg Phe Lys Lys Thr Lys Leu Ile Ala Ser Ile Ala Met Ala

-continued

```
1               5                   10                  15
Leu Cys Leu Phe Ser Gln Pro Val Ile Ser Phe Ser Lys Asp Ile Thr
                20                  25                  30
Asp Lys Asn Gln Ser Ile Asp Ser Gly Ile Ser Ser Leu Ser Tyr Asn
                35                  40                  45
Arg Asn Glu Val Leu Ala Ser Asn Gly Asp Lys Ile Glu Ser Phe Val
 50                  55                  60
Pro Lys Glu Gly Lys Lys Thr Gly Asn Lys Phe Ile Val Val Glu Arg
 65                  70                  75                  80
Gln Lys Arg Ser Leu Thr Thr Ser Pro Val Asp Ile Ser Ile Ile Asp
                85                  90                  95
Ser Val Asn Asp Arg Thr Tyr Pro Gly Ala Leu Gln Leu Ala Asp Lys
                100                 105                 110
Ala Phe Val Glu Asn Arg Pro Thr Ile Leu Met Val Lys Arg Lys Pro
                115                 120                 125
Ile Asn Ile Asn Ile Asp Leu Pro Gly Leu Lys Gly Glu Asn Ser Ile
                130                 135                 140
Lys Val Asp Asp Pro Thr Tyr Gly Lys Val Ser Gly Ala Ile Asp Glu
145                 150                 155                 160
Leu Val Ser Lys Trp Asn Glu Lys Tyr Ser Ser Thr His Thr Leu Pro
                165                 170                 175
Ala Arg Thr Gln Tyr Ser Glu Ser Met Val Tyr Ser Lys Ser Gln Ile
                180                 185                 190
Ser Ser Ala Leu Asn Val Asn Ala Lys Val Leu Glu Asn Ser Leu Gly
                195                 200                 205
Val Asp Phe Asn Ala Val Ala Asn Asn Glu Lys Lys Val Met Ile Leu
                210                 215                 220
Ala Tyr Lys Gln Ile Phe Tyr Thr Val Ser Ala Asp Leu Pro Lys Asn
225                 230                 235                 240
Pro Ser Asp Leu Phe Asp Asp Ser Val Thr Phe Asn Asp Leu Lys Gln
                245                 250                 255
Lys Gly Val Ser Asn Glu Ala Pro Pro Leu Met Val Ser Asn Val Ala
                260                 265                 270
Tyr Gly Arg Thr Ile Tyr Val Lys Leu Glu Thr Thr Ser Ser Ser Lys
                275                 280                 285
Asp Val Gln Ala Ala Phe Lys Ala Leu Ile Lys Asn Thr Asp Ile Lys
                290                 295                 300
Asn Ser Gln Gln Tyr Lys Asp Ile Tyr Glu Asn Ser Ser Phe Thr Ala
305                 310                 315                 320
Val Val Leu Gly Gly Asp Ala Gln Glu His Asn Lys Val Val Thr Lys
                325                 330                 335
Asp Phe Asp Glu Ile Arg Lys Val Ile Lys Asp Asn Ala Thr Phe Ser
                340                 345                 350
Thr Lys Asn Pro Ala Tyr Pro Ile Ser Tyr Thr Ser Val Phe Leu Lys
                355                 360                 365
Asp Asn Ser Val Ala Ala Val His Asn Lys Thr Asp Tyr Ile Glu Thr
                370                 375                 380
Thr Ser Thr Glu Tyr Ser Lys Gly Lys Ile Asn Leu Asp His Ser Gly
385                 390                 395                 400
Ala Tyr Val Ala Gln Phe Glu Val Ala Trp Asp Glu Val Ser Tyr Asp
                405                 410                 415
Lys Glu Gly Asn Glu Val Leu Thr His Lys Thr Trp Asp Gly Asn Tyr
                420                 425                 430
```

Gln Asp Lys Thr Ala His Tyr Ser Thr Val Ile Pro Leu Glu Ala Asn
            435                 440                 445

Ala Arg Asn Ile Arg Ile Lys Ala Arg Glu Cys Thr Gly Leu Ala Trp
450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
            485                 490                 495

Ile Thr Tyr Asn
            500

<210> SEQ ID NO 2
<211> LENGTH: 500
<212> TYPE: PRT
<213> ORGANISM: Clostridium perfringens

<400> SEQUENCE: 2

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
            85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
            115                 120                 125

Ile Asn Ile Asn Ile Asp Leu Pro Gly Leu Lys Gly Glu Asn Ser Ile
130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Thr His Thr Leu Pro
            165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
            195                 200                 205

Val Asp Phe Asn Ala Val Ala Asn Asn Glu Lys Lys Val Met Ile Leu
            210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
            245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
            275                 280                 285

Asp Val Gln Ala Ala Phe Lys Ala Leu Ile Lys Asn Thr Asp Ile Lys

```
                290                 295                 300
Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
                340                 345                 350

Thr Lys Asn Pro Ala Tyr Pro Ile Ser Tyr Thr Ser Val Phe Leu Lys
                355                 360                 365

Asp Asn Ser Val Ala Ala Val His Asn Lys Thr Asp Tyr Ile Glu Thr
                370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
                420                 425                 430

Gln Asp Lys Thr Ala His Tyr Ser Thr Val Ile Pro Leu Glu Ala Asn
                435                 440                 445

Ala Arg Asn Ile Arg Ile Lys Ala Arg Glu Cys Thr Gly Leu Ala Trp
                450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
                500

<210> SEQ ID NO 3
<211> LENGTH: 500
<212> TYPE: PRT
<213> ORGANISM: Clostridium perfringens

<400> SEQUENCE: 3

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
                20                  25                  30

Asp Lys Asn Gln Ser Ile Asp Ser Gly Ile Ser Ser Leu Ser Tyr Asn
                35                  40                  45

Arg Asn Glu Val Leu Ala Ser Asn Gly Asp Lys Ile Glu Ser Phe Val
                50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
                100                 105                 110

Ala Phe Val Glu Asn Arg Pro Thr Ile Leu Met Val Lys Arg Lys Pro
                115                 120                 125

Ile Asn Ile Asn Ile Asp Leu Pro Gly Leu Lys Gly Glu Asn Ser Ile
                130                 135                 140

Lys Val Asp Asp Pro Thr Tyr Gly Lys Val Ser Gly Ala Ile Asp Glu
145                 150                 155                 160
```

Leu Val Ser Lys Trp Asn Glu Lys Tyr Ser Thr His Thr Leu Pro
            165                 170                 175

Ala Arg Thr Gln Tyr Ser Glu Ser Met Val Tyr Ser Lys Ser Gln Ile
        180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
            245                 250                 255

Lys Gly Val Ser Asn Glu Ala Pro Pro Leu Met Val Ser Asn Val Ala
        260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
        290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
            325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
        355                 360                 365

Asp Asn Ser Val Ala Ala Val His Asn Lys Thr Asp Tyr Ile Glu Thr
        370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
            405                 410                 415

Lys Glu Gly Asn Glu Val Leu Thr His Lys Thr Trp Asp Gly Asn Tyr
        420                 425                 430

Gln Asp Lys Thr Ser His Tyr Ser Thr Val Ile Pro Leu Glu Ala Asn
        435                 440                 445

Val Arg Asn Ile Arg Ile Lys Ala Arg Glu Cys Thr Gly Leu Ala Trp
450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
            485                 490                 495

Ile Thr Tyr Asn
        500

<210> SEQ ID NO 4
<211> LENGTH: 542
<212> TYPE: PRT
<213> ORGANISM: Clostridium perfringens

<400> SEQUENCE: 4

Met Lys Phe Lys Ile Ile Ser Leu Leu Asn Pro Ile Lys Phe Leu Lys
1               5                   10                  15

Phe Lys Ser Ser Ile Lys Phe Leu Gly Phe Met Ser Leu Thr Asn Glu
            20                  25                  30

Gly Lys Ile Lys Lys Arg Gly Ile Tyr Ile Met Ile Arg Phe Lys Lys
            35                  40                  45

Thr Lys Leu Ile Ala Ser Ile Ala Met Ala Leu Cys Leu Phe Ser Gln
 50                  55                  60

Pro Val Ile Ser Phe Ser Lys Asp Ile Thr Asp Lys Asn Gln Ser Ile
 65                  70                  75                  80

Asp Ser Gly Ile Ser Ser Leu Ser Tyr Asn Arg Asn Glu Val Leu Ala
                85                  90                  95

Ser Asn Gly Asp Lys Ile Glu Ser Phe Val Pro Lys Glu Gly Lys Lys
            100                 105                 110

Thr Gly Asn Lys Phe Ile Val Glu Arg Gln Lys Arg Ser Leu Thr
            115                 120                 125

Thr Ser Pro Val Asp Ile Ser Ile Ile Asp Ser Val Asn Asp Arg Thr
130                 135                 140

Tyr Pro Gly Ala Leu Gln Leu Ala Asp Lys Ala Phe Val Glu Asn Arg
145                 150                 155                 160

Pro Thr Ile Leu Met Val Lys Arg Lys Pro Ile Asn Ile Asn Ile Asp
                165                 170                 175

Leu Pro Gly Leu Lys Gly Glu Asn Ser Ile Lys Val Asp Pro Thr
            180                 185                 190

Tyr Gly Lys Val Ser Gly Ala Ile Asp Glu Leu Val Ser Lys Trp Asn
            195                 200                 205

Lys Lys Tyr Ser Ser Thr His Thr Leu Pro Ala Arg Thr Gln Tyr Ser
210                 215                 220

Glu Ser Met Val Tyr Lys Ser Gln Ile Ser Ser Ala Leu Asn Val
225                 230                 235                 240

Asn Ala Lys Val Leu Glu Asn Ser Leu Gly Val Asp Phe Asn Ala Val
                245                 250                 255

Ala Asn Asn Glu Lys Lys Val Met Ile Leu Ala Tyr Lys Gln Ile Phe
            260                 265                 270

Tyr Thr Val Ser Ala Asp Leu Pro Lys Asn Pro Ser Asp Leu Phe Asp
            275                 280                 285

Asp Ser Val Thr Phe Asn Asp Leu Lys Gln Lys Gly Val Ser Asn Glu
290                 295                 300

Ala Pro Pro Leu Met Val Ser Asn Val Ala Tyr Gly Arg Thr Ile Tyr
305                 310                 315                 320

Val Lys Leu Glu Thr Thr Ser Ser Lys Asp Val Gln Ala Ala Phe
                325                 330                 335

Lys Ala Leu Ile Lys Asn Thr Asp Ile Lys Asn Ser Gln Gln Tyr Lys
            340                 345                 350

Asp Ile Tyr Glu Asn Ser Ser Phe Thr Ala Val Val Leu Gly Gly Asp
            355                 360                 365

Ala Gln Glu His Asn Lys Val Val Thr Lys Asp Phe Asp Glu Ile Arg
370                 375                 380

Lys Val Ile Lys Asp Asn Ala Thr Phe Ser Thr Lys Asn Pro Ala Tyr
385                 390                 395                 400

Pro Ile Ser Tyr Thr Ser Val Phe Leu Lys Asp Asn Ser Val Ala Ala
                405                 410                 415

Val His Asn Lys Thr Asp Tyr Ile Glu Thr Thr Ser Thr Glu Tyr Ser
            420                 425                 430

Lys Gly Lys Ile Asn Leu Asp His Ser Gly Ala Tyr Val Ala Gln Phe
            435                 440                 445

```
Glu Val Ala Trp Asp Glu Val Ser Tyr Asp Lys Gly Asn Glu Val
            450                 455                 460

Leu Thr His Lys Thr Trp Asp Gly Asn Tyr Gln Asp Lys Thr Ala His
465                 470                 475                 480

Tyr Ser Thr Val Ile Pro Leu Glu Ala Asn Ala Arg Asn Ile Arg Ile
                    485                 490                 495

Lys Ala Arg Glu Cys Thr Gly Leu Ala Trp Glu Trp Trp Arg Asp Val
                500                 505                 510

Ile Ser Glu Tyr Asp Val Pro Leu Thr Asn Asn Ile Asn Val Ser Ile
            515                 520                 525

Trp Gly Thr Thr Leu Tyr Pro Gly Ser Ser Ile Thr Tyr Asn
530                 535                 540

<210> SEQ ID NO 5
<211> LENGTH: 500
<212> TYPE: PRT
<213> ORGANISM: Clostridium perfringens

<400> SEQUENCE: 5

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
                20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
        50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
130                 135                 140

Lys Val Asp Asp Pro Thr Tyr Gly Lys Val Ser Gly Ala Ile Asp Glu
145                 150                 155                 160

Leu Val Ser Lys Trp Asn Asp Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285
```

```
Asp Val Gln Ala Ala Phe Lys Ala Leu Ile Lys Asn Thr Asp Ile Lys
            290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
355                 360                 365

Asp Asn Ser Val Ala Ala Val His Asn Lys Thr Asp Tyr Ile Glu Thr
        370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
435                 440                 445

Ala Arg Asn Ile Arg Ile Lys Ala Arg Glu Cys Thr Gly Leu Ala Trp
        450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500

<210> SEQ ID NO 6
<211> LENGTH: 499
<212> TYPE: PRT
<213> ORGANISM: Clostridium perfringens

<400> SEQUENCE: 6

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Glu Ala Ile
        115                 120                 125

Asn Ile Asn Ile Asp Leu Pro Gly Leu Lys Gly Glu Asn Ser Ile Lys
130                 135                 140

Val Asp Asp Pro Thr Tyr Gly Lys Val Ser Gly Ala Ile Asp Glu Leu
```

```
            145                 150                 155                 160

Val Ser Lys Trp Asn Glu Lys Tyr Ser Ser Thr His Thr Leu Pro Ala
                    165                 170                 175

Arg Thr Gln Tyr Ser Glu Ser Met Val Tyr Ser Lys Ser Gln Ile Ser
                    180                 185                 190

Ser Ala Leu Asn Val Asn Ala Lys Val Leu Glu Asn Ser Leu Gly Val
                    195                 200                 205

Asp Phe Asn Ala Val Ala Asn Glu Lys Lys Val Met Ile Leu Ala
    210                 215                 220

Tyr Lys Gln Ile Phe Tyr Thr Val Ser Ala Asp Leu Pro Lys Asn Pro
    225                 230                 235                 240

Ser Asp Leu Phe Asp Asp Ser Val Thr Phe Asn Asp Leu Lys Gln Lys
                    245                 250                 255

Gly Val Ser Asn Glu Ala Pro Pro Leu Met Val Ser Asn Val Ala Tyr
                    260                 265                 270

Gly Arg Thr Ile Tyr Val Lys Leu Glu Thr Thr Ser Ser Lys Asp
                    275                 280                 285

Val Gln Ala Ala Phe Lys Ala Leu Ile Lys Asn Thr Asp Ile Lys Asn
    290                 295                 300

Ser Gln Gln Tyr Lys Asp Ile Tyr Glu Asn Ser Ser Phe Thr Ala Val
    305                 310                 315                 320

Val Leu Gly Gly Asp Ala Gln Glu His Asn Lys Val Val Thr Lys Asp
                    325                 330                 335

Phe Asp Glu Ile Arg Lys Val Ile Lys Asp Asn Ala Thr Phe Ser Thr
                    340                 345                 350

Lys Asn Pro Ala Tyr Pro Ile Ser Tyr Thr Ser Val Phe Leu Lys Asp
                    355                 360                 365

Asn Ser Val Ala Ala Val His Asn Lys Thr Asp Tyr Ile Glu Thr Thr
                    370                 375                 380

Ser Thr Glu Tyr Ser Lys Gly Lys Ile Asn Leu Asp His Ser Gly Ala
    385                 390                 395                 400

Tyr Val Ala Gln Phe Glu Val Ala Trp Asp Glu Val Ser Tyr Asp Lys
                    405                 410                 415

Glu Gly Asn Glu Val Leu Thr His Lys Thr Trp Asp Gly Asn Tyr Gln
                    420                 425                 430

Asp Lys Thr Ala His Tyr Ser Thr Val Ile Pro Leu Glu Ala Asn Ala
                    435                 440                 445

Arg Asn Ile Arg Ile Lys Ala Arg Glu Cys Thr Gly Leu Ala Trp Glu
    450                 455                 460

Trp Trp Arg Asp Val Ile Ser Glu Tyr Asp Val Pro Leu Thr Asn Asn
    465                 470                 475                 480

Ile Asn Val Ser Ile Trp Gly Thr Thr Leu Tyr Pro Gly Ser Ser Ile
                    485                 490                 495

Thr Tyr Asn

<210> SEQ ID NO 7
<211> LENGTH: 500
<212> TYPE: PRT
<213> ORGANISM: Clostridium perfringens

<400> SEQUENCE: 7

Met Ile Arg Phe Lys Lys Thr Lys Leu Ile Ala Ser Ile Ala Met Ala
    1               5                   10                  15

Leu Cys Leu Phe Ser Gln Pro Val Ile Ser Phe Ser Lys Asp Ile Thr
```

```
                 20                  25                  30
Asp Lys Asn Gln Ser Ile Asp Ser Gly Ile Ser Ser Leu Ser Tyr Asn
                 35                  40                  45

Arg Asn Glu Val Leu Ala Ser Asn Gly Asp Lys Ile Glu Ser Phe Val
                 50                  55                  60

Pro Lys Glu Gly Lys Lys Ala Gly Asn Lys Phe Ile Val Val Glu Arg
 65                  70                  75                  80

Gln Lys Arg Ser Leu Thr Thr Ser Pro Val Asp Ile Ser Ile Ile Asp
                 85                  90                  95

Ser Val Asn Asp Arg Thr Tyr Pro Gly Ala Leu Gln Leu Ala Asp Lys
                100                 105                 110

Ala Leu Val Glu Asn Arg Pro Thr Ile Leu Met Val Lys Arg Lys Pro
                115                 120                 125

Ile Asn Ile Asn Ile Asp Leu Pro Gly Leu Lys Gly Glu Asn Ser Ile
                130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
                180                 185                 190

Ser Ser Ala Leu Asn Val Asn Ala Lys Val Leu Glu Asn Ser Leu Gly
                195                 200                 205

Val Asp Phe Asn Ala Val Ala Asn Asn Glu Lys Lys Val Met Ile Leu
                210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
                260                 265                 270

Tyr Gly Arg Thr Ile Tyr Val Lys Leu Glu Thr Thr Ser Ser Ser Lys
                275                 280                 285

Asp Val Gln Ala Ala Phe Lys Ala Leu Ile Lys Asn Thr Asp Ile Lys
                290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
                340                 345                 350

Thr Lys Asn Pro Ala Tyr Pro Ile Ser Tyr Thr Ser Val Phe Leu Lys
                355                 360                 365

Asp Asn Ser Val Ala Ala Val His Asn Lys Thr Asp Tyr Ile Glu Thr
                370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
                420                 425                 430

Gln Asp Lys Thr Ala His Tyr Ser Thr Val Ile Pro Leu Glu Ala Asn
                435                 440                 445
```

```
Ala Arg Asn Ile Arg Ile Lys Ala Arg Glu Cys Thr Gly Leu Ala Trp
    450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500

<210> SEQ ID NO 8
<211> LENGTH: 509
<212> TYPE: PRT
<213> ORGANISM: Clostridium perfringens

<400> SEQUENCE: 8

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ser Ser Arg Ser Lys Asp Ile Thr Asp Lys Asn Gln Ser Ile Asp
            35                  40                  45

Ser Gly Ile Ser Ser Leu Ser Tyr Asn Arg Asn Glu Val Leu Ala Ser
50                  55                  60

Asn Gly Asp Lys Ile Glu Ser Phe Val Pro Lys Glu Gly Lys Lys Ala
65                  70                  75                  80

Gly Asn Lys Phe Ile Val Val Glu Arg Gln Lys Arg Ser Leu Thr Thr
                85                  90                  95

Ser Pro Val Asp Ile Ser Ile Asp Ser Val Asn Asp Arg Thr Tyr
            100                 105                 110

Pro Gly Ala Leu Gln Leu Ala Asp Lys Ala Phe Val Glu Asn Arg Pro
            115                 120                 125

Thr Ile Leu Met Val Lys Arg Lys Pro Ile Asn Ile Asn Ile Asp Leu
130                 135                 140

Pro Gly Leu Lys Gly Glu Asn Ser Ile Lys Val Asp Asp Pro Thr Tyr
145                 150                 155                 160

Gly Lys Val Ser Gly Ala Ile Asp Glu Leu Val Ser Lys Trp Asn Glu
                165                 170                 175

Lys Tyr Ser Ser Thr His Thr Leu Pro Ala Arg Thr Gln Tyr Ser Glu
            180                 185                 190

Ser Met Val Tyr Ser Lys Ser Gln Ile Ser Ser Ala Leu Asn Val Asn
            195                 200                 205

Ala Lys Val Leu Glu Asn Ser Leu Gly Val Asp Phe Asn Ala Val Ala
210                 215                 220

Asn Asn Glu Lys Lys Val Met Ile Leu Ala Tyr Lys Gln Ile Phe Tyr
225                 230                 235                 240

Thr Val Ser Ala Asp Leu Pro Lys Asn Pro Ser Asp Leu Phe Asp Asp
                245                 250                 255

Ser Val Thr Phe Asn Asp Leu Lys Gln Lys Gly Val Ser Asn Glu Ala
            260                 265                 270

Pro Pro Leu Met Val Ser Asn Val Ala Tyr Gly Arg Thr Ile Tyr Val
            275                 280                 285

Lys Leu Glu Thr Thr Ser Ser Ser Lys Asp Val Gln Ala Ala Phe Lys
290                 295                 300

Ala Leu Ile Lys Asn Thr Asp Ile Lys Asn Ser Gln Gln Tyr Lys Asp
```

```
            305                 310                 315                 320
Ile Tyr Glu Asn Ser Ser Phe Thr Ala Val Val Leu Gly Gly Asp Ala
                325                 330                 335

Gln Glu His Asn Lys Val Val Thr Lys Asp Phe Asp Glu Ile Arg Lys
                340                 345                 350

Val Ile Lys Asp Asn Ala Thr Phe Ser Thr Lys Asn Pro Ala Tyr Pro
                355                 360                 365

Ile Ser Tyr Thr Ser Val Phe Leu Lys Asp Asn Ser Val Ala Ala Val
        370                 375                 380

His Asn Lys Thr Asp Tyr Ile Glu Thr Thr Ser Thr Glu Tyr Ser Lys
385                 390                 395                 400

Gly Lys Ile Asn Leu Asp His Ser Gly Ala Tyr Val Ala Gln Phe Glu
                405                 410                 415

Val Ala Trp Asp Glu Val Ser Tyr Asp Lys Glu Gly Asn Glu Val Leu
                420                 425                 430

Thr His Lys Thr Trp Asp Gly Asn Tyr Gln Asp Lys Thr Ala His Tyr
            435                 440                 445

Ser Thr Val Ile Pro Leu Glu Ala Asn Ala Arg Asn Ile Arg Ile Lys
        450                 455                 460

Ala Arg Glu Cys Thr Gly Leu Ala Trp Glu Trp Trp Arg Asp Val Ile
465                 470                 475                 480

Ser Glu Tyr Asp Val Pro Leu Thr Asn Asn Ile Asn Val Ser Ile Trp
                485                 490                 495

Gly Thr Thr Leu Tyr Pro Gly Ser Ser Ile Thr Tyr Asn
                500                 505

<210> SEQ ID NO 9
<211> LENGTH: 509
<212> TYPE: PRT
<213> ORGANISM: Clostridium perfringens

<400> SEQUENCE: 9

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ser Ser Arg Ser Lys Asp Ile Thr Asp Lys Asn Gln Ser Ile Asp
            35                  40                  45

Ser Gly Ile Ser Ser Leu Ser Tyr Asn Arg Asn Glu Val Leu Ala Ser
        50                  55                  60

Asn Gly Asp Lys Ile Glu Ser Phe Val Pro Lys Glu Gly Lys Lys Ala
65                  70                  75                  80

Gly Asn Lys Phe Ile Val Val Glu Arg Gln Lys Arg Ser Leu Thr Thr
                85                  90                  95

Ser Pro Val Asp Ile Ser Ile Ile Asp Ser Val Asn Asp Arg Thr Tyr
            100                 105                 110

Pro Gly Ala Leu Gln Leu Ala Asp Lys Ala Phe Val Glu Asn Arg Pro
        115                 120                 125

Thr Ile Leu Met Val Lys Arg Lys Pro Ile Asn Ile Asn Ile Asp Leu
130                 135                 140

Pro Gly Leu Lys Gly Glu Asn Ser Ile Lys Val Asp Asp Pro Thr Tyr
145                 150                 155                 160

Gly Lys Val Ser Gly Ala Ile Asp Glu Leu Val Ser Lys Trp Asn Glu
                165                 170                 175
```

```
Lys Tyr Ser Ser Thr His Thr Leu Pro Ala Arg Thr Gln Tyr Ser Glu
            180                 185                 190

Ser Met Val Tyr Ser Lys Ser Gln Ile Ser Ser Ala Leu Asn Val Asn
        195                 200                 205

Ala Lys Val Leu Glu Asn Ser Leu Gly Val Asp Phe Asn Ala Val Ala
210                 215                 220

Asn Asn Glu Lys Lys Val Met Ile Leu Ala Tyr Lys Gln Ile Phe Tyr
225                 230                 235                 240

Thr Val Ser Ala Asp Leu Pro Lys Asn Pro Ser Asp Leu Phe Asp Asp
            245                 250                 255

Ser Val Thr Phe Asn Asp Leu Lys Gln Lys Gly Val Ser Asn Glu Ala
        260                 265                 270

Pro Pro Leu Met Val Ser Asn Val Ala Tyr Gly Arg Thr Ile Tyr Val
            275                 280                 285

Lys Leu Glu Thr Thr Ser Ser Lys Asp Val Gln Ala Ala Phe Lys
        290                 295                 300

Ala Leu Ile Lys Asn Thr Asp Ile Lys Asn Ser Gln Gln Tyr Lys Asp
305                 310                 315                 320

Ile Tyr Glu Asn Ser Ser Phe Thr Ala Val Val Leu Gly Gly Asp Ala
                325                 330                 335

Gln Glu His Asn Lys Val Val Thr Lys Asp Phe Asp Glu Ile Arg Lys
            340                 345                 350

Val Ile Lys Asp Asn Ala Thr Phe Ser Thr Lys Asn Pro Ala Tyr Pro
            355                 360                 365

Ile Ser Tyr Thr Ser Val Phe Leu Lys Asp Asn Ser Val Ala Ala Val
        370                 375                 380

His Asn Lys Thr Asp Tyr Ile Glu Thr Thr Ser Thr Glu Tyr Ser Lys
385                 390                 395                 400

Gly Lys Ile Asn Leu Asp His Ser Gly Ala Tyr Val Ala Gln Phe Glu
                405                 410                 415

Val Ala Trp Asp Glu Val Ser Tyr Asp Lys Glu Gly Asn Glu Val Leu
            420                 425                 430

Thr His Lys Thr Trp Asp Gly Asn Tyr Gln Asp Lys Thr Ala His Tyr
        435                 440                 445

Ser Thr Val Ile Pro Leu Glu Ala Asn Ala Arg Asn Ile Arg Ile Lys
450                 455                 460

Ala Arg Glu Ala Thr Gly Leu Ala Trp Glu Trp Trp Arg Asp Val Ile
465                 470                 475                 480

Ser Glu Tyr Asp Val Pro Leu Thr Asn Asn Ile Asn Val Ser Ile Trp
                485                 490                 495

Gly Thr Thr Leu Tyr Pro Gly Ser Ser Ile Thr Tyr Asn
            500                 505

<210> SEQ ID NO 10
<211> LENGTH: 509
<212> TYPE: PRT
<213> ORGANISM: Clostridium perfringens

<400> SEQUENCE: 10

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ser Ser Arg Ser Lys Asp Ile Thr Asp Lys Asn Gln Ser Ile Asp
        35                  40                  45
```

-continued

```
Ser Gly Ile Ser Ser Leu Ser Tyr Asn Arg Asn Glu Val Leu Ala Ser
    50                  55                  60
Asn Gly Asp Lys Ile Glu Ser Phe Val Pro Lys Glu Gly Lys Lys Ala
 65                  70                  75                  80
Gly Asn Lys Phe Ile Val Val Glu Arg Gln Lys Arg Ser Leu Thr Thr
                 85                  90                  95
Ser Pro Val Asp Ile Ser Ile Ile Asp Ser Val Asn Asp Arg Thr Tyr
                100                 105                 110
Pro Gly Ala Leu Gln Leu Ala Asp Lys Ala Phe Val Glu Asn Arg Pro
                115                 120                 125
Thr Ile Leu Met Val Lys Arg Lys Pro Ile Asn Ile Asn Ile Asp Leu
                130                 135                 140
Pro Gly Leu Lys Gly Glu Asn Ser Ile Lys Val Asp Asp Pro Thr Tyr
145                 150                 155                 160
Gly Lys Val Ser Gly Ala Ile Asp Glu Leu Val Ser Lys Trp Asn Glu
                165                 170                 175
Lys Tyr Ser Ser Thr His Thr Leu Pro Ala Arg Thr Gln Tyr Ser Glu
                180                 185                 190
Ser Met Val Tyr Ser Lys Ser Gln Ile Ser Ser Ala Leu Asn Val Asn
                195                 200                 205
Ala Lys Val Leu Glu Asn Ser Leu Gly Val Asp Phe Asn Ala Val Ala
                210                 215                 220
Asn Asn Glu Lys Lys Val Met Ile Leu Ala Tyr Lys Gln Ile Phe Tyr
225                 230                 235                 240
Thr Val Ser Ala Asp Leu Pro Lys Asn Pro Ser Asp Leu Phe Asp Asp
                245                 250                 255
Ser Val Thr Phe Asn Asp Leu Lys Gln Lys Gly Val Ser Asn Glu Ala
                260                 265                 270
Pro Pro Leu Met Val Ser Asn Val Ala Tyr Gly Arg Thr Ile Tyr Val
                275                 280                 285
Lys Leu Glu Thr Thr Ser Ser Ser Lys Asp Val Gln Ala Ala Phe Lys
                290                 295                 300
Ala Leu Ile Lys Asn Thr Asp Ile Lys Asn Ser Gln Gln Tyr Lys Asp
305                 310                 315                 320
Ile Tyr Glu Asn Ser Ser Phe Thr Ala Val Leu Gly Gly Asp Ala
                325                 330                 335
Gln Glu His Asn Lys Val Val Thr Lys Asp Phe Asp Glu Ile Arg Lys
                340                 345                 350
Val Ile Lys Asp Asn Ala Thr Phe Ser Thr Lys Asn Pro Ala Tyr Pro
                355                 360                 365
Ile Ser Tyr Thr Ser Val Phe Leu Lys Asp Asn Ser Val Ala Ala Val
                370                 375                 380
His Asn Lys Thr Asp Tyr Ile Glu Thr Thr Ser Thr Glu Tyr Ser Lys
385                 390                 395                 400
Gly Lys Ile Asn Leu Asp His Ser Gly Ala Tyr Val Ala Gln Phe Glu
                405                 410                 415
Val Ala Trp Asp Glu Val Ser Tyr Asp Lys Glu Gly Asn Glu Val Leu
                420                 425                 430
Thr His Lys Thr Trp Asp Gly Asn Tyr Gln Ser Lys Thr Ala His Tyr
                435                 440                 445
Ser Thr Val Ile Pro Leu Glu Ala Asn Ala Arg Asn Ile Arg Ile Lys
450                 455                 460
```

```
Ala Arg Glu Ala Thr Gly Leu Ala Trp Glu Trp Arg Asp Val Ile
465                 470                 475                 480

Ser Glu Tyr Asp Val Pro Leu Thr Asn Asn Ile Asn Val Ser Ile Trp
                485                 490                 495

Gly Thr Thr Leu Tyr Pro Gly Ser Ser Ile Thr Tyr Asn
                500                 505
```

<210> SEQ ID NO 11
<211> LENGTH: 509
<212> TYPE: PRT
<213> ORGANISM: Clostridium perfringens

<400> SEQUENCE: 11

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Ser Ser Arg Ser Lys Asp Ile Thr Asp Lys Asn Gln Ser Ile Asp
                35                  40                  45

Ser Gly Ile Ser Ser Leu Ser Tyr Asn Arg Asn Glu Val Leu Ala Ser
        50                  55                  60

Asn Gly Asp Lys Ile Glu Ser Phe Val Pro Lys Gly Lys Lys Ala
65                  70                  75                  80

Gly Asn Lys Phe Ile Val Val Glu Arg Gln Lys Arg Ser Leu Thr Thr
                85                  90                  95

Ser Pro Val Asp Ile Ser Ile Ile Asp Ser Val Asn Asp Arg Thr Tyr
                100                 105                 110

Pro Gly Ala Leu Gln Leu Ala Asp Lys Ala Phe Val Glu Asn Arg Pro
            115                 120                 125

Thr Ile Leu Met Val Lys Arg Lys Pro Ile Asn Ile Asn Ile Asp Leu
    130                 135                 140

Pro Gly Leu Lys Gly Glu Asn Ser Ile Lys Val Asp Asp Pro Thr Tyr
145                 150                 155                 160

Gly Lys Val Ser Gly Ala Ile Asp Glu Leu Val Ser Lys Trp Asn Glu
                165                 170                 175

Lys Tyr Ser Ser Thr His Thr Leu Pro Ala Arg Thr Gln Tyr Ser Glu
                180                 185                 190

Ser Met Val Tyr Ser Lys Ser Gln Ile Ser Ser Ala Leu Asn Val Asn
            195                 200                 205

Ala Lys Val Leu Glu Asn Ser Leu Gly Val Asp Phe Asn Ala Val Ala
    210                 215                 220

Asn Asn Glu Lys Lys Val Met Ile Leu Ala Tyr Lys Gln Ile Phe Tyr
225                 230                 235                 240

Thr Val Ser Ala Asp Leu Pro Lys Asn Pro Ser Asp Leu Phe Asp Asp
                245                 250                 255

Ser Val Thr Phe Asn Asp Leu Lys Gln Lys Gly Val Ser Asn Glu Ala
                260                 265                 270

Pro Pro Leu Met Val Ser Asn Val Ala Tyr Gly Arg Thr Ile Tyr Val
            275                 280                 285

Lys Leu Glu Thr Thr Ser Ser Lys Asp Val Gln Ala Ala Phe Lys
    290                 295                 300

Ala Leu Ile Lys Asn Thr Asp Ile Lys Asn Ser Gln Gln Tyr Lys Asp
305                 310                 315                 320

Ile Tyr Glu Asn Ser Ser Phe Cys Ala Val Val Leu Gly Gly Asp Ala
                325                 330                 335
```

-continued

```
Gln Glu His Asn Lys Val Cys Thr Lys Asp Phe Asp Glu Ile Arg Lys
                340                 345                 350

Val Ile Lys Asp Asn Ala Thr Phe Ser Thr Lys Asn Pro Ala Tyr Pro
            355                 360                 365

Ile Ser Tyr Thr Ser Val Phe Leu Lys Asp Asn Ser Val Ala Ala Val
370                 375                 380

His Asn Lys Thr Asp Tyr Ile Glu Thr Thr Ser Thr Glu Tyr Ser Lys
385                 390                 395                 400

Gly Lys Ile Asn Leu Asp His Ser Gly Ala Tyr Val Ala Gln Phe Glu
                405                 410                 415

Val Ala Trp Asp Glu Val Ser Tyr Asp Lys Glu Gly Asn Glu Val Leu
            420                 425                 430

Thr His Lys Thr Trp Asp Gly Asn Tyr Gln Asp Lys Thr Ala His Tyr
        435                 440                 445

Ser Thr Val Ile Pro Leu Glu Ala Asn Ala Arg Asn Ile Arg Ile Lys
    450                 455                 460

Ala Arg Glu Ala Thr Gly Leu Ala Trp Glu Trp Arg Asp Val Ile
465                 470                 475                 480

Ser Glu Tyr Asp Val Pro Leu Thr Asn Asn Ile Asn Val Ser Ile Trp
                485                 490                 495

Gly Thr Thr Leu Tyr Pro Gly Ser Ser Ile Thr Tyr Asn
            500                 505

<210> SEQ ID NO 12
<211> LENGTH: 509
<212> TYPE: PRT
<213> ORGANISM: Clostridium perfringens

<400> SEQUENCE: 12

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ser Ser Arg Ser Lys Asp Ile Thr Asp Lys Asn Gln Ser Ile Asp
        35                  40                  45

Ser Gly Ile Ser Ser Leu Ser Tyr Asn Arg Asn Glu Val Leu Ala Ser
    50                  55                  60

Asn Gly Asp Lys Ile Glu Ser Phe Val Pro Lys Gly Lys Lys Ala
65                  70                  75                  80

Gly Asn Lys Phe Ile Val Val Glu Arg Gln Lys Arg Ser Leu Thr Thr
                85                  90                  95

Ser Pro Val Asp Ile Ser Ile Ile Asp Ser Val Asn Asp Arg Thr Tyr
            100                 105                 110

Pro Gly Ala Leu Gln Leu Ala Asp Lys Ala Phe Val Glu Asn Arg Pro
        115                 120                 125

Thr Ile Leu Met Val Lys Arg Lys Pro Ile Asn Ile Asn Ile Asp Leu
    130                 135                 140

Pro Gly Leu Lys Gly Glu Asn Ser Ile Lys Val Asp Asp Pro Thr Tyr
145                 150                 155                 160

Gly Lys Val Ser Gly Ala Ile Asp Glu Leu Val Ser Lys Trp Asn Glu
                165                 170                 175

Lys Tyr Ser Ser Thr His Thr Leu Pro Ala Arg Thr Gln Tyr Ser Glu
            180                 185                 190

Ser Met Val Tyr Ser Lys Ser Gln Ile Ser Ser Ala Leu Asn Val Asn
```

-continued

```
            195                 200                 205
Ala Lys Val Leu Glu Asn Ser Leu Gly Val Asp Phe Asn Ala Val Ala
        210                 215                 220
Asn Asn Glu Lys Lys Val Met Ile Leu Ala Tyr Lys Gln Ile Phe Tyr
225                 230                 235                 240
Thr Val Ser Ala Asp Leu Pro Lys Asn Pro Ser Asp Leu Phe Asp Asp
                245                 250                 255
Ser Val Thr Phe Asn Asp Leu Lys Gln Lys Gly Val Ser Asn Glu Ala
                260                 265                 270
Pro Pro Leu Met Val Ser Asn Val Ala Tyr Gly Arg Thr Ile Tyr Val
                275                 280                 285
Lys Leu Glu Thr Thr Ser Ser Ser Lys Asp Val Gln Ala Ala Phe Lys
        290                 295                 300
Ala Leu Ile Lys Asn Thr Asp Ile Lys Asn Ser Gln Gln Tyr Lys Asp
305                 310                 315                 320
Ile Tyr Glu Asn Ser Ser Phe Cys Ala Val Val Leu Gly Gly Asp Ala
                325                 330                 335
Gln Glu His Asn Lys Val Cys Thr Lys Asp Phe Asp Glu Ile Arg Lys
                340                 345                 350
Val Ile Lys Asp Asn Ala Thr Phe Ser Thr Lys Asn Pro Ala Tyr Pro
                355                 360                 365
Ile Ser Tyr Thr Ser Val Phe Leu Lys Asp Asn Ser Val Ala Ala Val
        370                 375                 380
His Asn Lys Thr Asp Tyr Ile Glu Thr Thr Ser Thr Glu Tyr Ser Lys
385                 390                 395                 400
Gly Lys Ile Asn Leu Asp His Ser Gly Ala Tyr Val Ala Gln Phe Glu
                405                 410                 415
Val Ala Trp Asp Glu Val Ser Tyr Asp Lys Glu Gly Asn Glu Val Leu
                420                 425                 430
Thr His Lys Thr Trp Asp Gly Asn Tyr Gln Ser Lys Thr Ala His Tyr
        435                 440                 445
Ser Thr Val Ile Pro Leu Glu Ala Asn Ala Arg Asn Ile Arg Ile Lys
        450                 455                 460
Ala Arg Glu Ala Thr Gly Leu Ala Trp Glu Trp Trp Arg Asp Val Ile
465                 470                 475                 480
Ser Glu Tyr Asp Val Pro Leu Thr Asn Asn Ile Asn Val Ser Ile Trp
                485                 490                 495
Gly Thr Thr Leu Tyr Pro Gly Ser Ser Ile Thr Tyr Asn
                500                 505
```

METHODS, COMPOSITIONS AND KITS FOR ASSAYING MITOCHONDRIAL FUNCTION

RELATED APPLICATION

This application claims priority under 35 U.S.C. § 119(e) to U.S. Provisional Patent Application Ser. No. 61/473,730, filed Apr. 8, 2011, and entitled "Methods, Compositions and Kits for Assaying Mitochondrial Function," which is incorporated herein by reference in its entirety for all purposes.

GOVERNMENT SUPPORT

This work was supported under grant number 5R21NS057224-03, awarded by National Institutes of Health (NIH). The U.S. Government has certain rights in the invention.

FIELD OF THE INVENTION

The invention relates to methods for evaluating intracellular functions as well as cell health and viability.

BACKGROUND OF THE INVENTION

Mitochondrial dysfunction is at the core of many encephalomyopathies, diabetes and cancer. Inherited mutations in over 100 genes constituting the oxidative phosphorylation (OxPhos) machinery are linked with mitochondrial encephalomyopathies in humans. The diseases resulting from defective OxPhos are also referred to as mitochondrial diseases or mitochondrial disorders. They are usually multisystemic fatal disorders with progressive onset with age. Impaired mitochondrial metabolism is also thought to play a key role in the pathophysiology of diabetes and cancer. Mutational analysis of mitochondrial (mt)DNA suggests that mitochondrial dysfunction is a widespread phenomenon, which occurs in almost all types of cancers. Somatic mutations in the mtDNA, which encodes proteins essential for OxPhos, are found associated with almost all types of cancer. However, their functional relevance is yet to be determined in most cases.

The COSMIC (Catalogue Of Somatic Mutations In Cancer) database reveals that mutations in nuclear genes associated with oxidative phosphorylation functions is common. Somatic mutations in over 25 nuclear genes associated with respiratory Complex I (NADH-ubiquinone oxidoreductase) structure/function have been identified. In addition, switching of the cellular metabolism from oxidative metabolism to glycolysis, which is known as metabolic reprogramming, is one of the hallmarks of cancer phenotypes. This could be due to somatic mutations in mtDNA, nDNA or negative regulation of the oxidative phosphorylation due to host and environmental factors. Mitochondrial dysfunction is also implicated in other age-associated diseases such as Parkinson's disease, and Alzheimer's disease. Thus, there is an need for simple and accurate methods to assess the mitochondrial function in the context of pathophysiology. Such methods can lead to determinations of "cause and effect" relationships between the mitochondrial metabolism and pathophysiology, and efficacies of therapeutic interventions in restoring normal mitochondrial metabolism. Accordingly, methods for accurately measuring mitochondrial function are important not only for detecting and understanding these diseases, but also for evaluating therapies and other treatments that impact oxidative phosphorylation In terms of cellular bioenergetics, it can be useful to determine the reserve (spare) capacity of mitochondria to make ATP (the oxidative phosphorylation capacity), and its relationship with the maximal oxygen consumption by the respiratory chain (the respiratory capacity), which determine the fate of cells under conditions of acute/high ATP demand.

SUMMARY OF THE INVENTION

Aspects of the invention relate to methods, compositions, and devices that are useful for measuring mitochondrial functions accurately and reproducibly under intracellular conditions. In some embodiments, the invention relates to methods, compositions, and devices that are useful for measuring mitochondrial functions accurately and reproducibly under different conditions without isolating the mitochondria from cells. In some embodiments, cholesterol-dependent cytolysins (CDCs) (e.g., perfringolysin O (PFO)) are used to permeabilize plasma membranes and not internal cellular membranes such as mitochondrial membranes. This selective permeabilization allows accurate evaluations of intracellular mitochondrial activities, by assaying, for example, the uptake and/or release of mitochondrial substrates and/or products that can be measured outside a selectively permeabilized cell.

Unlike methods that involve removing mitochondria from cells, analyses with permeabilized cells provide a more accurate assessment of the biological or physiological status of mitochondria, while allowing direct correlation with whole cells containing the same amount of mitochondria as in permeabilized cells. Traditionally, methods for analyzing intracellular mitochondrial activity involve using detergents or other permeabilization agents that are damaging to one or both of the cellular and mitochondrial membranes. Detergents, for example, typically solubilize mitochondrial membranes, and even with careful titrations below <0.01% it is difficult to establish concentrations of detergents under which mitochondrial function is sustained.

Cholesterol-dependent cytolysin-based (e.g., PFO-based) methods provide effective permeabilization of cellular membranes without disrupting the mitochondrial membranes. Thus, permeabilization with cytolysins avoids unwanted release of mitochondrial molecules into the cell and surrounding cellular environment. This also avoids cytosolic molecules entering the mitochondria and interfering with mitochondrial function. Moreover, cholesterol-dependent cytolysins are surprisingly effective at creating conditions suitable for measuring mitochondrial activity in cells. In some embodiments, cholesterol-dependent cytolysin-based (e.g., PFO-based) methods provide effective permeabilization of cellular membranes without disrupting the mitochondrial membranes at concentrations over a wide dynamic range up to 50 nM or more in some cases (e.g., 0.1 to 20 nM). Also, since the cytolysins are proteins, they can typically be handled very accurately at different dilutions.

Therefore, cholesterol-dependent cytolysin-based permeabilization techniques can be used to evaluate one or more mitochondrial activities without disrupting the cellular environment, because mitochondrial membranes remain largely intact when exposed to a cholesterol-dependent cytolysin (e.g., PFO) as described herein. Substrate uptake and/or product release can be assayed to evaluate one or more mitochondrial-specific functions (e.g., oxidative phosphorylation). Accordingly, cholesterol-dependent cytolysin-based (e.g., PFO-based) assay results can provide an accurate assessment of mitochondrial activity in a natural cellular environment. In some embodiments, cholesterol-dependent cytolysin-based (e.g., PFO-based) assay results can provide an accurate assessment of mitochondrial activity in cells obtained from subjects suspected of having a mitochondrial disorder.

In some embodiments, cholesterol-dependent cytolysin-based (e.g., PFO-based) cell permeabilization allows for analysis of the effects of exogenous agents (e.g., molecules that are impermeable across the plasma membrane) on one or more intracellular functions. In some embodiments, cholesterol-dependent cytolysins (e.g., PFOs) facilitate the use of exogenous agents such as dyes, fluorescent proteins, markers or other agents to probe one or more intracellular functions. For example, cholesterol-dependent cytolysin-based (e.g., PFOs) may facilitate the use of exogenous agents such as ion sensitive dyes (e.g., calcium sensing dyes, pH sensing dyes, etc.) or ion sensitive fluorescent proteins to probe one or more intracellular functions. In some embodiments, cholesterol-dependent cytolysin-based (e.g., PFOs) may be used to facilitate transfection of cells with exogenous nucleic acids (e.g., expression vectors).

Methods are provided, in some embodiments, that are based on selective permeabilization of the plasma membrane with a cholesterol-dependent pore forming protein, perfringolysin O (PFO) from the *Clostridium perfringens*. In some embodiments, because relatively large amounts of cholesterol are concentrated in the plasma membrane compared with intracellular membranes, intracellular membranes remain largely unaffected by CDCs such as PFO. In some embodiments, compared with traditional cell permeabilization techniques, such as those employing digitonin, PFO-permeabilized cells preserve mitochondrial integrity, and produce reproducible results across a wide range of cell types and buffer conditions.

In some embodiments, methods are provided that utilize PFO-based cell permeabilization (e.g., in a microplate format) that are useful for determining spare oxidative phosphorylation (OxPhos) capacity and other features of mitochondrial bioenergetics. In some embodiments, the methods permit assessment of mitochondrial function without isolating mitochondria from cells. In some embodiments, the methods are useful for determining (i) spare and total OxPhos capacities, (ii) spare and total respiratory capacities, (iii) specific defects in electron transport/respiratory chain (ETC/RC) capacities, (iv) TCA cycle function, and/or (v) cell-specific features of mitochondrial metabolism. In some embodiments, PFO-based assays may be used for measuring spare OxPhos (SOC) capacity and spare respiratory (ETC/RC) capacity (SRC) in a single assay. In some embodiments, evaluating spare or total OxPhos capacity involves using adequate amounts of ADP (e.g., 1 mM for cells, ≥2 mM for myoblasts), and Pi (e.g., ≥10 mM) in the respiration medium along with a desired substrate. In some embodiments, the methods are useful for determining spare OxPhos capacity and other bioenergetic features without the need to isolate mitochondria from cells. In some embodiments, methods are useful for determining: (i) cell-specific features of mitochondrial metabolism, (ii) direct and/or indirect effects of drugs on ETC/RC function and other mitochondrial functions, (iii) defects OxPhos complexes, (iv) uncoupling activity of compounds and/or (v) conditions that can impair functional integrity of mitochondria.

In some embodiments, the methods disclosed herein are useful for assessing mitochondrial function and metabolism in cell lines, primary cells and tissues. In some embodiments, the methods are useful for determining oxidative phosphorylation and respiratory chain capacities. In some embodiments, the methods are useful for determining the capacity of individual respiratory OxPhos Complexes (I-V).

In some embodiments, the methods are useful for evaluating mitochondrial permeability transitions. In some embodiments, the methods are useful for diagnosing impaired mitochondrial metabolism, e.g., due to genetic mutations or drug toxicity. In some embodiments, the methods are useful for evaluating organelles' (e.g., mitochondria, Lysosomes, nucleus, endoplasmic reticulum etc.) function under conditions maintain mitochondrial function. In some embodiments, the methods are useful for evaluating protein topology in internal membranes by assessing protease sensitivity of internal membrane proteins following PFO-based permeabilization. In some embodiments, the methods are useful for facilitating delivery of macromolecules inside cells using conditional pore-formation.

In some embodiments, PFO-permeabilized cells are used to determine conditions for maximal respiratory response with different NADH substrates (e.g., pyruvate, isocitrate, α-ketoglutarate and glutamate) when added individually. In some embodiments, the methods disclosed herein are useful for assessing mitochondrial function with small samples applicable to clinical research. In some embodiments, the methods are useful for assessing mitochondrial permeability transition and other cellular processes, and organelles under the conditions that do not destroy mitochondrial functions.

In some embodiments, PFO derivatives are provided that can be used at as low as 0.1 nM concentrations for mitochondrial function assays. In some embodiments, PFO derivatives are provided that can be used in the absence of DTT or other reducing agents. In such embodiments, $O_2$ consumption resulting from DTT or other reducing agents is avoided. In some embodiments, a minimal amount of DTT is used (e.g., ≤100 nM of DTT). In some embodiments, PFO-based assays are provided that are applicable across different cells, e.g., β cells, fibroblasts, neuronal cells, primary myoblasts/tubes, mammary epithelial cells, embryonic fibroblasts, macrophages, splenocytes and thymocytes, and different species of cells, e.g., mouse, rat, hamster and human. In some embodiments, different variants of PFO are provided (See, e.g., Tables 3 and 5).

According to some aspects of the invention methods are provided that comprise contacting a preparation comprising a cell with a cholesterol-dependent cytolysin and measuring an intracellular function of the cell. In some embodiments, the intracellular function is a metabolic rate of the cell, a respiratory rate of the cell, a proportion of aerobic to anaerobic respiration, a rate of consumption of a molecule, or a production rate of a molecule. In some embodiments, the intracellular function is indicative of cell health or cell viability. In some embodiments, the intracellular function is mitochondrial function. In some embodiments, the methods are used as an apoptosis (a cell death mechanism) assay.

It should be appreciated that a preparation typically comprises a plurality of cells. Such preparations may comprise one or more cells of any type. In some embodiments, the cells may be animal cells or plant cells. In some embodiments, the cells are primary cells. In some embodiments, the cells are obtained from an individual. The cells may be any mammalian cells. The cells may be any human cells. The cells may be selected from the group consisting of Lymphocytes, B cells, T cells, cytotoxic T cells, natural killer T cells, regulatory T cells, T helper cells, myeloid cells, granulocytes, basophil granulocytes, eosinophil granulocytes, neutrophil granulocytes, hypersegmented neutrophils, monocytes, macrophages, reticulocytes, platelets, mast cells, thrombocytes, megakaryocytes, dendritic cells, thyroid cells, thyroid epithelial cells, parafollicular cells, parathyroid cells, parathyroid chief cells, oxyphil cells, adrenal cells, chromaffin cells, pineal cells, pinealocytes, glial cells, glioblasts, astrocytes, oligodendrocytes, microglial cells, magnocellular neurosecretory cells, stellate cells, boettcher cells; pituitary cells, gonadotropes, corticotropes, thyrotropes, somatotrope, lactotrophs, pneumocyte, type I pneumocytes, type II pneumocytes. Clara cells; goblet cells, alveolar macrophages, myocardiocytes, pericytes, gastric cells, gastric chief cells, parietal cells, goblet cells, paneth cells, G cells, D cells, ECL cells, I cells, K cells, S cells, enteroendocrine cells, enterochromaffin cells, APUD cell, liver cells, hepatocytes, Kupffer cells, bone cells, osteoblasts, osteocytes, osteoclast, odontoblasts, cementoblasts, aneloblasts, cartilage cells, chondroblasts, chondrocytes, skin cells, hair cells, trichocytes, keratinocytes, melanocytes, nevus cells, muscle cells, myocytes, myoblasts, myotubes, adipocyte, fibroblasts, tendon cells, podocytes, juxtaglomerular cells, intraglomerular mesangial cells, extraglomerular mesangial cells, kidney cells, kidney cells, macula densa cells, spermatozoa, sertoli cells, leydig cells, oocytes, and mixtures thereof. Accordingly, the cells may be of mesenchymal, ectodermal, and endodermal origin. The cells may be selected from the group consisting of cord-blood cells, stem cells, embryonic stem cells, adult stem cells, progenitor cells, induced progenitor cells, autologous cells, isograft cells, allograft cells, xenograft cells, and genetically engineered cells.

According to some aspects of the invention, methods are provided that comprise contacting a preparation comprising a cell with a cholesterol-dependent cytolysin (CDC) and determining the level of a molecule in the preparation, in which the level of the molecule is indicative of an intracellular function of the cell. In some embodiments, the level of the molecule is indicative of mitochondrial function. In some embodiments, the cholesterol-dependent cytolysin is a protein or variant or derivative thereof selected from Table 1. In some embodiments, the cholesterol-dependent cytolysin is a protein having an amino acid sequence corresponding to a GenBank Accession Number listed in Table 1, or a variant or derivative thereof. In some embodiments, the cholesterol-dependent cytolysin is a protein that is a member of the family of cholesterol-dependent cytolysins listed in Table 1, or a variant or derivative thereof.

In some embodiments, the cholesterol-dependent cytolysin is a Perfringolysin O (PFO). As used herein, the term "Perfringolysin O (PFO)" refers to a cytolysin of a *Clostridium perfringens* bacterium, or a variant, derivative or recombinant form of such a cytolysin that is capable of forming pores in a plasma membrane of a cell. In some embodiments. PFOs form pores in the plasma membrane of cells in a cholesterol-dependent manner. In some embodiments, the PFO comprises an amino acid sequence as set forth in any one of SEQ ID NOS: 1-12, or a variant or derivative thereof. In some embodiments, the PFO comprises an amino acid sequence that is a fragment of an amino acid sequence as set forth in any one of SEQ ID NOS: 1-12. In some embodiments, the fragment comprises an amino acid sequence as set forth in any one of SEQ ID NOS: 1-7 that does not include an N-terminal signal sequence. In some embodiments, the N-terminal signal sequences is the first 10, 11, 12, 13, 14, 15, 16, 17, 18, 19, 20, 21, 22, 23, 24, 25, 26, 27, 28, 29, 30, 31, 32, 33, 34, or 35 amino acids of the amino acid sequence. In some embodiments, the PFO comprises an amino acid sequence that has at least 50%, at least 60%, at least 70%, at least 80%, at least 85%, at least 90%, at least 95%, at least 99%, or more sequence identity or sequence homology with a sequence as set forth in any one of SEQ ID NOS: 1-12. Sequence homology can be calculated using various, publicly available software tools developed by NCBI (Bethesda, Md.), for example, that can be obtained through the internet. Exemplary tools include "protein blast" available online at blast.ncbi.nlm.nih.gov/Blast.cgi, which may be utilized with its default settings. In some embodiments, the PFO comprises an amino acid sequence that has an amino acid substitution at up to 25, up to 20, up to 15, up to 10, up to 5, or up to 2 positions compared with the sequence as set forth in any one of SEQ ID NOS: 1-12.

In some embodiments, the PFO comprises an amino acid sequence that has one or more conservative amino acid substitutions, e.g., one or more conservative amino acid substitutions compared with any one of SEQ ID NO: 1-12. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Accordingly, conservative amino acid substitutions may provide functionally equivalent variants, or homologs of a protein.

In some embodiments, the PFO comprises an amino acid sequence as set forth in SEQ ID NO: 1 or 2 with a cysteine to alanine substitution at amino acid position 459. In some embodiments of the methods, the PFO comprises an amino acid sequence as set forth in SEQ ID NO: 1 or 2 with a threonine to cysteine substitution at amino acid position 319 and/or a valine to cysteine substitution at amino acid position 334. In such embodiments, methods that utilize the PFO may further comprise adding a reducing reagent to the preparation. In certain embodiments, the reducing reagent is Dithiothreitol (DTT) or 2-Mercaptoethanol.

In some embodiments, the PFO comprises an amino acid sequence as set forth in SEQ ID NO: 1 or 2 with a cysteine to alanine substitution at amino acid position 459, and one or more other amino acid substitutions. In some embodiments of the methods, the PFO comprises an amino acid sequence as set forth in SEQ ID NO: 1 or 2 with a threonine to cysteine substitution at amino acid position 319 and/or a valine to cysteine substitution at amino acid position 334, and one or more other amino acid substitutions.

In some embodiments, an isolated perfringolysin O (PFO) is provided that comprises an amino acid sequence as set forth in SEQ ID NO: 1 or 2 with an aspartate to serine substitution at amino acid position 434. In some embodiments, an isolated perfringolysin O (PFO) is provided that comprises an amino acid sequence as set forth in SEQ ID NO: 1 or 2 with an aspartate to serine substitution at amino acid position 434 and one or more other amino acid substitutions.

In some embodiments of the methods involving determining the level of a molecule in a preparation, the molecule is $O_2$. In some embodiments, the level of $O_2$ in the preparation is indicative of the oxygen consumption rate of the cell. In some embodiments, the oxygen consumption rate is indicative of mitochondrial function. In some embodiments of the methods involving determining the level of a molecule in a preparation, the molecule is $H^+$. In some embodiments, the level of $H^+$ in the preparation is indicative of the $H^+$ production rate of the cell.

In some embodiments, the methods further comprise contacting the cell with a cellular-respiration effector. In some embodiments, the cellular-respiration effector is a nucleotide or a protonophore. In some embodiments, the nucleotide is adenosine diphosphate (ADP). In such embodiments, the methods may further comprise measuring the oxygen consumption rate of the cell, wherein the ADP-stimulated oxygen consumption rate is indicative of oxidative phosphorylation in the cell. In some embodiments, the protonophore is cyanide-p-trifluoromethoxyphenylhydrazone (FCCP). In such embodiments, the methods may further comprise measuring the oxygen consumption rate of the cell, wherein the FCCP-stimulated oxygen consumption rate is indicative of electron transport and respiratory chain function in the cell.

In some embodiments, the methods further comprise contacting the cell with glutamate, pyruvate, malate, isocitrate, alpha-ketoglutarate or a combination thereof. In such embodiments, results of the methods may be indicative of the enzymatic activity of Complex I (NADH-ubiquinone oxidoreductase) in the cell.

In some embodiments, the methods further comprise contacting the cell with succinate. In such embodiments, the results of the methods may be indicative of the enzymatic activity of Complex II (succinate-ubiquinone oxidoreductase) in the cell.

In some embodiments, the methods further comprise contacting the cell with Glycerol 3-phosphate. In such embodiments, results of the methods may be indicative of the enzymatic activity of Complex III (ubiquinol-cytochrome c oxidoreductase) in the cell.

In some embodiments, the methods further comprise contacting the cell with N,N,N',N'-Tetramethyl-p-Phenylenediamine (TMPD) and/or ascorbate. In such embodiments, results of the methods may be indicative of the enzymatic activity of Complex IV (cytochrome c oxidase) in the cell.

In some embodiments, the methods further comprise contacting the cell with succinate and ADP and/or contacting the cell with glycerol-3-phosphate. In some embodiments, the methods further comprise contacting the cell with succinate, glycerol-3-phosphate and ADP. In such embodiments, results of the methods may be indicative of the enzymatic activity of Complex V (ATP synthase) in the cell.

In some embodiments, the methods further comprise contacting the cell with a respiratory chain inhibitor, an oxidative phosphorylation inhibitor, an uncoupling agent, a transport inhibitor, an ionophore or a krebs cycle inhibitor. In some embodiments, the methods further comprise contacting the cell with rotenone, malonate, antimycin A, KCN, and oligomycin.

In some embodiments, the methods further comprise contacting the cell with a test agent and determining an effect of the test agent on an intracellular function (e.g., mitochondrial function). In some embodiments, the test agent is a drug candidate. Accordingly, in some embodiments, the methods provide assays for drug screens. The methods may be used in some embodiments to screen libraries of unknown or known compounds (e.g., known bioactive compounds) to identify compounds that affect intracellular function, such as uncoupling ATP synthesis with respiratory chain function. In other embodiments, the methods may be used to evaluate the toxicity of compounds. Accordingly, in some embodiments, the methods may be used for evaluating lead compounds.

In some embodiments, the methods further comprise identifying one or more genetic mutations in the cell. In some embodiments, the results of the methods are indicative of whether the one or more genetic mutations affect the intracellular function (e.g., mitochondrial function) of the cell. In some embodiments, the one or more genetic mutations are associated with a mitochondrial disorder.

In some embodiments, methods are provided that involve contacting a preparation comprising a cell obtained from a subject with a cholesterol-dependent cytolysin; and determining the level of a molecule in the preparation, wherein the level of the molecule is indicative of the presence or absence of a respiratory chain deficiency in the cell.

In some embodiments, the cell is obtained from an individual having or suspected of having a mitochondrial disorder. In some embodiments, the results of the methods aid in diagnosing an individual as having one or more mitochondrial disorders. In some embodiment, the mitochondrial disorder is selected from the group consisting of Myoclonic Epilepsy with Ragged Red Fibers (MERRF); Mitochondrial Myopathy, Encephalopathy, Lactacidosis, and Stroke (MELAS); Diabetes mellitus and deafness (DAD) a combination, which at an early age can be due to mitochondrial disease; Maternally Inherited Diabetes and Deafness (MIDD), Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (Co-Q10) Deficiency; Neuropathy, ataxia, retinitis pigmentosa, and ptosis (NARP); Myoneurogenic gastrointestinal encephalopathy (MNGIE); Complex I Deficiency; Complex II Deficiency; Complex III Deficiency; Complex IV Deficiency; Complex V Deficiency; another mitochondrial disease; and other myopathies that effect mitochondrial function. In some embodiments, the mitochondrial disorder is passed genetically from parent to child (i.e., is an inherited disorder).

In some embodiments, an individual having one or more symptoms of a mitochondrial disorder may be suspected of having the mitochondrial disorder. Symptoms of mitochondrial disorders include muscle weakness or exercise intolerance, heart failure or rhythm disturbances, dementia, movement disorders, stroke-like episodes, deafness, blindness, droopy eyelids, limited mobility of the eyes, vomiting, and seizures. During physical activity, muscles may become easily fatigued or weak. Muscle cramping may occur. Nausea, headache, and breathlessness are also associated with these disorders. Often, mitochondrial disorders occur or first manifest at a young age (e.g., during childhood, before the age of 20). Accordingly, in some embodiments, the methods may be useful for diagnosing or aiding in diagnosing a mitochondrial disorder in an individual who is a child. However, it should be appreciated that the diagnostic methods disclosed herein may be used with individuals of any age.

A "subject," "individual," or "patient," is used interchangeably herein, which refers to a vertebrate, preferably a mammal, more preferably a human. Mammals include, but are not limited to, murines, simians, humans, farm animals, sport animals, and pets. In some embodiments, the subject, individual or patient is a child. In some embodiments, the subject, individual or patient is a young child. In some embodiments, the subject, individual or patient is an infant. As defined herein, the term "child" or "children" as used herein means persons over the age of 3 years and prior to adolescence. As used herein, the term "young child" or "young children" means persons from the age of more than 12 months up to the age of three years. As used herein, the term "infant" means a person not more than 12 months of age. In some embodiments, the subject, individual or patient is at or above the age of adolescence.

In some embodiments, methods of transfecting a cell with an exogenous nucleic acid are provided. In some embodiments, the methods involve contacting the cell with any one or more of the cholesterol-dependent cytolysins disclosed herein; and contacting the cell with the exogenous nucleic acid (e.g., an expression vector, a cloning vector, etc.). In some embodiments, the methods are useful for transfecting cells that are difficult to transfect with conventional transfection reagents (e.g., liposome based reagents). In some embodiments, the methods are useful for transfecting cells grown in suspension, e.g., hematopoietic cells. In some embodiments, the methods are useful for transfecting stem cells or primary cells.

In some embodiments of the methods, the preparation is contained in a container, e.g., a well. In some embodiments, the container is a well in a multi-well plate. Accordingly, in some embodiments, the methods may be performed in a multiplex format (e.g., high-throughput format). In some embodiments, the methods are conducted using a multi-well extracellular flux analyzer.

According to some aspects of the invention, kits are provided that comprise a container housing a cholesterol-dependent cytolysin and a container housing a reagent for evaluating an intracellular function of a cell. In some embodiments, the intracellular function is a mitochondrial function. In some embodiments, kits are provided that comprise a container housing a cholesterol-dependent cytolysin and a container housing a cellular-respiration effector.

In some embodiments of the kits, the cellular-respiration effector is a nucleotide or a protonophore. In certain embodiments, the nucleotide is adenosine diphosphate (ADP). In certain embodiments, the protonophore is cyanide-p-trifluoromethoxyphenylhydrazone (FCCP).

In some embodiments, kits are provided that comprise a container housing glutamate, pyruvate, malate, isocitrate, alpha-ketoglutarate or a combination thereof. In some embodiments, kits are provided that comprise a container housing succinate. In some embodiments, kits are provided that comprise a container housing Glycerol 3-phosphate. In some embodiments, kits are provided that comprise a container housing N,N,N',N'-Tetramethyl-p-Phenylenediamine (TMPD). In some embodiments, kits are provided that comprise a container housing ascorbate.

In some embodiments, kits are provided that comprise a container housing a respiratory chain inhibitor, a oxidative phosphorylation inhibitor, an uncoupling agent, a transport inhibitor, an ionophore or a krebs cycle inhibitor. In some embodiments, kits are provided that comprise a container housing rotenone, malonate, antimycin A, KCN, or oligomycin. In some embodiments, kits are provided that comprise a container housing assay buffer.

In some embodiments of the kits, the cholesterol-dependent cytolysin is selected from Table 1 or a variant or derivative thereof. In some embodiments, the cholesterol-dependent cytolysin is Perfringolysin O (PFO). In some embodiments, the PFO comprises an amino acid sequence as set forth in any one of SEQ ID NOS: 1-12, or a variant or derivative thereof. In some embodiments, the PFO comprises an amino acid sequence as set forth in SEQ ID NO: 1 or 2 with a cysteine to alanine substitution at amino acid position 459. In some embodiments, the PFO comprises an amino acid sequence as set forth in SEQ ID NO: 1 or 2 with a threonine to cysteine substitution at amino acid position 319 and/or a valine to cysteine substitution at amino acid position 334. In some embodiments, kits are provided that comprise a container housing a reducing reagent. In some embodiments, the reducing reagent is Dithiothreitol (DTT) or 2-Mercaptoethanol.

In some embodiments of the kits, at least one container is a reusable container. In some embodiments of the kits, at least one container is a single-use container. In some embodiments of the kits, at least one container is a tube or bottle. In some embodiments of the kits, the tube is a snap-top tube or a screw-top tube. In some embodiments of the kits, the bottle is a snap-top bottle or a screw-top bottle. In some embodiments of the kits, at least one container is a glass vial. In some embodiments of the kits, the containers are housed together in a box or a package. In some embodiments, the kits further comprise instructions for permeabilizing a cell. In some embodiments, the kits further comprise instructions for storing at least one container at a particular temperature (e.g., less than 0° C., room temperature). In some embodiments, the kits further comprise instructions for carrying out any of the methods disclosed herein using reagents provided in the kits.

While in some embodiments the kits disclosed herein are useful for research purposes, in other embodiments, the kits disclosed herein are useful for diagnostic purposes. Accordingly, in some embodiments, the kits contain one or more reagents or components useful in methods for diagnosing or aiding in diagnosing an individual as having a mitochondrial disorder, including, for example, any of the mitochondrial disorders disclosed herein.

BRIEF DESCRIPTION OF THE DRAWINGS

FIG. 3A shows primary pancreatic β-cells. FIG. 3B shows Chinese hamster lung fibroblasts. Injections were as follows: "a" was 1 mM ADP+10 µM Cytochrome c (Cyt C or CC) with nPFO (25 nM) or Digitonin (DIG, 0.010% in FIG. 3A, 0.005% in FIG. 3B) in the presence of succinate as respiratory substrate; and "b" was 1 µg/ml oligomycin. OCR rates either shown as absolute value (FIG. 3A) or normalized to 3rd rate (FIG. 3B).

FIG. 5A shows relative levels of ADP- and FCCP-stimulated respiration in Chinese hamster lung fibroblasts, the V79-G3.

Injections were as follows: "a" was 1 mM ADP; "b" was 2 µM FCCP. FIG. 5B shows oligomycin sensitivity (coupling test) of the ADP-stimulated respiration in permeabilized V79-G3 cells compared to the sensitivity of basal respiration in intact cells. Injections were as follows "a" was 1 mM ADP or ADP+nPFO; and "b" was 2 µg/ml oligomycin. FIG. 5C shows respiratory decline following nPFO permeabilization is due to ADP limitation resulting from the dilution of the cytosol. Injections were as follows: "a" was 5 nM nPFO; and "b" was buffer (nPFO) or 1 mM ADP (nPFO+ADP) or 1 mM ADP+10 µM Cytochrome c (nPFO+ADP+CC).

FIG. 6A shows rat insulinoma INS1E cells. Injections were as follows: "a" was nPFO+ADP; and "b" was FCCP. FIG. 6B shows primary rat 0/islet-cells. Injections were as follows "a" was nPFO. "b" was succinate+ADP, and "c" was FCCP. The lower rates of basal respiration in primary cells are due to pre-starvation and the absence of any exogenous substrates prior to injection arrow "b".

FIG. 7A shows results of a complex I mutant showing the lack of respiration on Complex I substrates. FIG. 7B shows complemented control cells showing the restoration respiration on Complex I substrates. FIG. 7C shows the data from panel B with the basal rate before arrow "a" is set to "0". Injections were as follows: "a" was nPFO, and "b" was succinate (Suc), or glutamate+malate (Glu+Mal).

FIG. 11A shows Complex I, II, & III-dependent respiration determined by measuring respiratory inhibition with the increasing concentrations of rotenone (Rot), thenoyltrifluoroacetone (TTFA), antimycin A (Ant A) respectively compared to control (Con). FIG. 11B shows percent maximal respiratory inhibition by rotenone, TTFA and antimycin A in INS1E cells.

FIG. 12A shows results from primary β-cells. FIG. 12B shows results from primary astrocytes. FIG. 12C shows results from CCL16 lung fibroblasts. FIG. 12D shows NAD(P)H levels in isolated mitochondria in the presence of glutamate+malate and rotenone. Arrows indicate the following: "a" indicates cell permeabilization; and "b" indicates substrate+ADP (for FIGS. 12A,12B) or ADP (for FIG. 12C). In FIG. 12C, all substrates were added in the respiration buffer before permeabilization. Pyruvate, glutamate, malate, isocitrate, α-ketoglutarate and rotenone are indicated with one letter symbols: P, G, M, I, K and R respectively.

FIG. 13A shows INS1E cells. FIG. 13B shows V79 Chinese hamster lung fibroblasts. FIG. 13C shows primary β-cells. Arrows indicate the following: "a" indicate permeabilization with ADP (for FIGS. 13A, 13B) or without ADP (for FIG. 13C); "b" indicates FCCP (for FIGS. 13A,13B) or ADP (for FIG. 13C); "c" indicates FCCP. Maximal respiratory stimulations with ADP and FCCP were taken as the indices of the oxidative phosphorylation and respiratory capacities, respectively.

FIG. 14A shows that glucose (Glu) and pyruvate (Pyr) stimulate respiration in INS1E cells, which gradually declines in the presence of oligomycin. Lo & Hi indicates 2 mM and 16.7 mM glucose. FIG. 14B shows the respiratory decline in the presence of oligomycin is due to the limitations in substrate supply to the respiratory chain. Letters P, S, F indicate permeabilization, succinate and FCCP, respectively.

FIG. 16A shows exogenous Cyt C used for maximal respiration. β cells were first permeabilized with 0.01% digitonin (DIG) and then 1 mM ADP either alone (ADP) or with 10 µM Cyt C (ADP+CC) was added at right arrow. Control group did not receive either ADP or Cyt C. FIG. 16B shows respiratory coupling with ATP synthesis under the assay conditions used in FIG. 16A. Cells were first permeabilized with 0.01% DIG in the presence (Oligo-FCCP) or absence (Control, Oligo, FCCP) of 2 µg/ml Oligo and then following additions were made: "Control", which is ADP+CC; "Oligo", which is control plus Oligo; "FCCP", which is control plus 2 µM FCCP; "Oligo-FCCP", which is Oligo plus 2 M FCCP. FIG. 16C shows data from FIG. 16B with basal rate set at 100% for the comparison of ADP- and FCCP-stimulated respiration rates. FIGS. 16D-16F show results from primary rat astrocytes (FIG. 16D), hamster B2-MWFE cells (FIG. 16E) and human H1080 cells (FIG. 16F) that were first permeabilized with indicated concentrations of digitonin (DIG) and then 1 mM ADP with 10 µM Cyt C (ADP+CC) was added.

The ADP- and FCCP-stimulated respiration over basal respiration rates (BRR) were indicative of Spare OxPhos capacity (SOC) and spare respiratory capacity (SRC), respectively. FIG. 17A shows the respiratory response of primary pancreatic β cells permeabilized with 25 nM nPFO or 0.01% digitonin (DIG). Succinate and ADP were added at the time of permeabilization in the presence of 10 μM Cyt C (Succ+ADP). 1 μg/ml oligomycin (Oligo) was added to determine the coupling efficiency. FIG. 17B shows results of nPFO titration using INS1E cells. Assay conditions were the same as in FIG. 17A except Cyt C was not added. ADP with varying concentrations of nPFO (@ADP) and 2 μM FCCP (@FCCP) were added. FIG. 17C shows SOC compared with SRC in INS1E cells. FIG. 17D shows nPFO concentration compared with SOC in INS1E cells. FIG. 17E shows SOC compared with SRC in V79-G3 cells. FIG. 17F shows nPFO concentration compared with SOC and SRC in V79-G3 cells.

FIG. 18A shows mitochondrial integrity in nPFO-permeabilized INS1E cells ("ADP" indicates 1 mM ADP alone; "ADP+CC" indicates 1 mM ADP+10 μM Cyt C). FIG. 18B shows respiratory coupling in nPFO-permeabilized INS1E cells ("ADP" indicates 1 mM ADP alone; "oligo" indicates 1 mM ADP with 1 μg/ml oligomycin; "ADP+FCCP" indicates 1 mM ADP+1 μg/ml oligomycin+2 μM FCCP). FIG. 18C shows data from FIG. 18B normalized with basal rate set at 100% for comparison of ADP- and FCCP-stimulated respiration rates. FIG. 18D shows integrity in nPFO-permeabilized V79-G3 cells ("control" indicates buffer only; "ADP" indicates 1 mM ADP; "ADP+CC" indicates 1 mM ADP with 10 μM Cyt C). FIG. 18E shows respiratory decline in nPFO-permeabilized (nPFO) compared with oligomycin-treated intact (Oligo) V79-G3 cells. FIG. 18F shows oligomycin-insensitive respiration in intact compared with permeabilized V79-G3 cells ("Oligo" indicates 1 mM ADP followed by oligomycin; "nPFO+ADP_Oligo" indicates nPFO with 1 mM ADP followed by oligomycin). FIGS. 18G and 18H show mitochondrial integrity in nPFO-permeabilized HEK293 and SHSY-5Y cells, respectively ("ADP" indicates 1 mM ADP; "ADP+CC" indicates 1 mM ADP+10 μM Cyt C).

In FIGS. 19A-19C, the succinate and ADP were added with nPFO, while in FIGS. 19D-19F they were added after permeabilization with nPFO. FIG. 19A shows SOC and SRC in intact (SRCi) and permeabilized (SRCp) HEK293 cells. In "Control," 2 μM FCCP was added to non-permeabilized cells; In "nPFO," 3 μM FCCP was added to permeabilized cells after measuring succinate+ADP-stimulated respiration. FIG. 19B shows an estimation of total OxPhos (TOC) capacity in HEK293 cells by adding SOC to the oligomycin-sensitive portion of basal respiration rate. Total respiratory capacity is estimated by the maximal respiration rate in nPFO-permeabilized cells ("PSA_F" indicates nPFO+succinate+ADP followed by FCCP addition; "O_PSAF" indicates oligomycin followed by nPFO+succinate+ADP+FCCP addition). FIG. 19C shows an coupling efficiency of HEK293 cells determined by monitoring oligomycin-sensitive portion of the ADP-stimulated respiration ("PSA_O" indicates nPFO+succinate+ADP followed by oligomycin addition; "O_PSAF" indicates oligomycin followed by nPFO+succinate+ADP+FCCP addition). FIG. 19D-19F shows a strategy for determination of TOC by serial additions of nPFO, ADP, and FCCP in different cells such as HEK293 (FIG. 19D). SHSY-5Y (FIG. 19E) and β cells (FIG. 19F).

FIG. 20A depicts substrate-dependent variation in OxPhos capacity of primary β cells in Ca2+-free LKB buffer containing 2 mM glucose ("succ" indicates succinate; "G+M" indicates glutamate+malate; "G3-P" indicates glycerol-3-phosphate). FIG. 20B shows the effect of free Ca2+ on succinate-supported OxPhos in β cells under assay conditions used in the experiments associated with FIG. 20A ("control" indicates succinate+ADP; "CaCl$_2$" indicates 700 μM CaCl$_2$ added with succinate+ADP). FIG. 20C shows the effect of different respiration buffers on the OxPhos capacity of HEK293 cells. Cells were incubated in different buffers (see Table 6) and then ADP-stimulated respiration was measured. 2 μg/ml oligomycin was added to test the coupling efficiency. FIG. 20D shows coupling efficiency (CE) in different buffers. Data from FIG. 20C are plotted. FIG. 20E shows the effect of phosphate (KH$_2$PO$_4$) on OxPhos and respiratory capacity. See Table 6 for LKB, HKB, and MAS buffers. KH$_2$PO$_4$ is the LKB with 10 mM KH$_2$PO$_4$ instead of 0.4 mM. FIG. 20F shows data from FIG. 20E re-plotted after setting basal respiration rate to 100%. FIG. 20G shows, for INS1E cells, spare OxPhos capacity in different buffers, comparing LKB with LPBT, and HKB with HPBT. Basal respiration rate before permeabilization was set at 100%. FIG. 20H shows differences in the basal and ADP-stimulated respiration rates of INS1E cells in high Na+ and high K+ buffers. Actual respiration rates in LPBT and HPBT buffers for FIG. 20G are shown. FIG. 20I shows the effect of different buffers on Complex I- and Complex II-dependent respirations in INS1E cells.

In FIGS. 21A-21C, Complex I dependence of the glutamate+malate (Glu+Mal)-supported respiration is shown. Assays were performed in free Ca2+LKB buffer containing 15 mM glucose. β cells were permeabilized with 1 nM nPFO and ADP-stimulated respiration was measured using the indicated substrates. In FIG. 21A a rotenone sensitivity test of the Glu+Mal-supported respiration is shown. 2 μM rotenone (Rot) was used to inhibit Complex I. In FIG. 21B, a lack of Glu+Mal-supported respiration in Complex I-deficient CCL16-B2 cells is shown. FIG. 21C shows complex I activity rescued in B2-MWFE cells (which are CCL16-B2 cells complemented with wild type Chinese hamster Ndufa1 cDNA). FIG. 21D provides data showing that malate effects efficient utilization of NADH generating substrates such as pyruvate (P), isocitrate (I), glutamate (G), and .-ketoglutarate (K ("PF", "IF", "GF" and "KF" indicate, respectively, P, I, G, and K being added separately with 2 μM FCCP; "PGMIKF" indicates P, I, G, and K added together with FCCP). Malate was added last (3rd arrow from left) in all groups except in PGMIKF, which received it with other substrates. FIG. 21E shows a lack of Complex I-dependent respiration on individual substrates (P, G, M, I, K) in primary β cells ("PA", "GA", "MA", "IA" and "KA" indicate, respectively, P, G, I, M, and K added separately with 1 mM ADP). Succinate-supported respiration (SA) was used as positive control. While the SA group received 2 μM FCCP at 3rd injection, other groups received 10 mM succinate. FIG. 21F shows complex I-dependent respiration in rat astrocytes compared with INS1E cells. Glu+Mal supported respiration was monitored in astrocytes and IS1E cells in the presence (Astro_GM+ROT, INS1E_GM+ROT) and absence (Astro_GM, INS1E_GM) of 2 μM rotenone.

FIG. 22A shows progressive respiratory decline in INS1E cells in the presence of oligomycin. LKB buffer containing 2 mM glucose in the presence of 1.3 mM $CaCl_2$ was used for the assays; EGTA was not added. After measuring the basal respiration rates in 2 mM glucose, 14.7 mM glucose or 10 mM pyruvate were added (left arrow) to measure respiratory stimulations. Subsequently, approximately 90 min later, 2 μg/ml oligomycin (Oligo) was added. Control group received buffer only. FIG. 22B shows effects of oligomycin on ETC/RC function of INS1E cells. Ca2+-free LKB buffer with 16.7 mM glucose and without added EGTA was used for the assays. β cells were incubated for approximately 60 min in 16.7 mM glucose before the assay was performed. All groups were treated with 2 μg/ml oligomycin (Oligo) at indicated time point, and then received 10 mM succinate and/or 2 μM FCCP with ±nPFO. "Control" indicates buffer only; "Succ+FCCP" indicates succinate+FCCP only (no PFO); "nPFO+FCCP_Succ" indicates nPFO+FCCP followed by succinate addition; "nPFO+Succ+FCCP" indicates nPFO+succinate+FCCP added together.

FIG. 23A shows an actual graph obtained from the XF24 analyzer. Successive additions of 1 μM FCCP were made using ports A, B, C, and D resulting in cumulative concentrations of 1, 2, 3, and 4 μM FCCP respectively. FIG. 23B shows a linear relationship of the basal and maximal respiration rates with cell density. Data from rates 3 (without FCCP) and 6 (with 2 μM FCCP) in FIG. 23A were used.

FIG. 23A shows relative mitochondrial function in digitonin (0.01% DIG) compared with saponin (5-25 μg/ml SAP) permeabilized cells. FIG. 23B shows relative mitochondrial function in digitonin (0.01% DIG) compared with alamethicin (3-30 μg/ml ALA) permeabilized cells.

FIGS. 25A and 25B are shown after setting basal respiration rate to 100% in FIG. 25C. FIG. 25D shows a comparison of nPFO and dbPFO using INS1E cells. Assays were performed in Ca2+-free LKB with 2 mM glucose and cells were permeabilized with 1 nM nPFO or 1 nM dbPFO+1 mM DTT. FIG. 25E shows the effects of 1 mM DTT on respiration of permeabilized INS1E cells. FIG. 25F shows the effect of 1 mM DTT on the respiration of intact INS1E cell.

FIG. 28A shows the relative performance at 0.1 nM. FIG. 28B shows the relative performance at 1.0 nM. FIG. 28C shows a comparison of activity of nPFO at both 0.1 and 1.0 nM concentrations. FIG. 28D shows a comparison of activity among PFO variants at both concentrations (0.1 & 1.0 nM). Assays were performed in LPBT buffer (see Table 6).

FIGS. 29A and 29B show inverse relationships between digitonin concentration and respiratory activity in LKB buffer. In FIG. 29A, succinate was present in the medium before permeabilization and in FIG. 29B it was added with ADP. Compare arrows ADP and Succ+ADP in both panels. Assay was done with starved INS1E cells. FIGS. 29C and 29D show effects of the respiratory buffer used in non-starved INS1E cells. Respiration declines faster in LKB buffer (FIG. 29C) compared to that in LPBT (FIG. 29D) at all digitonin concentrations tested. FIGS. 29E and 29F show that Cytochrome c loss with digitonin is associated with respiratory decline. Addition of exogenous Cytochrome c (CC) with succinate+ADP inhibits the respiratory decline even at highest digitonin concentration used (0.01%) in both LKB & LPBT buffers.

FIG. 30A shows respiratory decline following the addition of oligomycin (Oligo; 1 μg/ml) and response to uncoupler FCCP (2 μM). FIG. 30B shows data in FIG. 30A re-plotted with base line set to 100% at rate 4. A faster decline and no response to FCCP is depicted in high K+ buffer (HPBT).

FIGS. 31A and 31D show base-line normalized respiration rates of rotenone-treated HEK293 human cells in LKB (FIG. 31A) and LPBT (FIG. 31D) buffers ("Rot" indicates 0, 10, 20, 50 & 1000 nM rotenone added at arrow; "P/GM/A" indicates 1 nM rPFO, glutamate+malate (10 mM each), 1 mM ADP & 3 μM FCCP; "succ" indicates 10 mM succinate). FIGS. 31B and 31E show respiration rates and rotenone concentrations plotted from data in FIGS. 31A and 31D, respectively ("Basal" indicates decline in respiration of intact cells; "Glu+Mal" indicates Complex I dependent respiration in the presence of FCCP; and "succ" indicates Complex II-dependent respiration in the presence of FCCP). FIG. 31C shows percent inhibition of Complex I and II-dependent respirations at different rotenone doses ("LKB-CI, CII" indicates Complex I and II functions in LKB buffer; and "LPBT-CI, II" indicates Complex I and II functions in LPBT buffer). FIG. 31F shows a relationship between the basal Complex I inhibition (in intact cells) and maximal Complex I inhibition (in permeabilized cells) in LKB (broken lines) and LPBT buffer (solid lines). At maximal rotenone dose (1 μM) no significant difference was observed between basal and maximal as well as between the buffers (see FIGS. 31B and 31E).

FIGS. 32A-32B show differences in the basal and maximal respiration rates of WT and S55A MEFs. Maximal respiration was determined by using the increasing dose of FCCP (2-4 μM). FIGS. 32C-32D show respiratory activity in cells that were permeabilized by recombinant perfringolysin O (rPFO). Complex I and II activities were measured by using specific substrates in the presence of ADP+FCCP ("Glu+Mal" indicates glutamate+malate and "succ" indicates succinate). 100,000 cells/well were spun down in V7 plates and measurements were made after 4 hours of culture.

DETAILED DESCRIPTION OF CERTAIN EMBODIMENTS OF THE INVENTION

Figure 1:
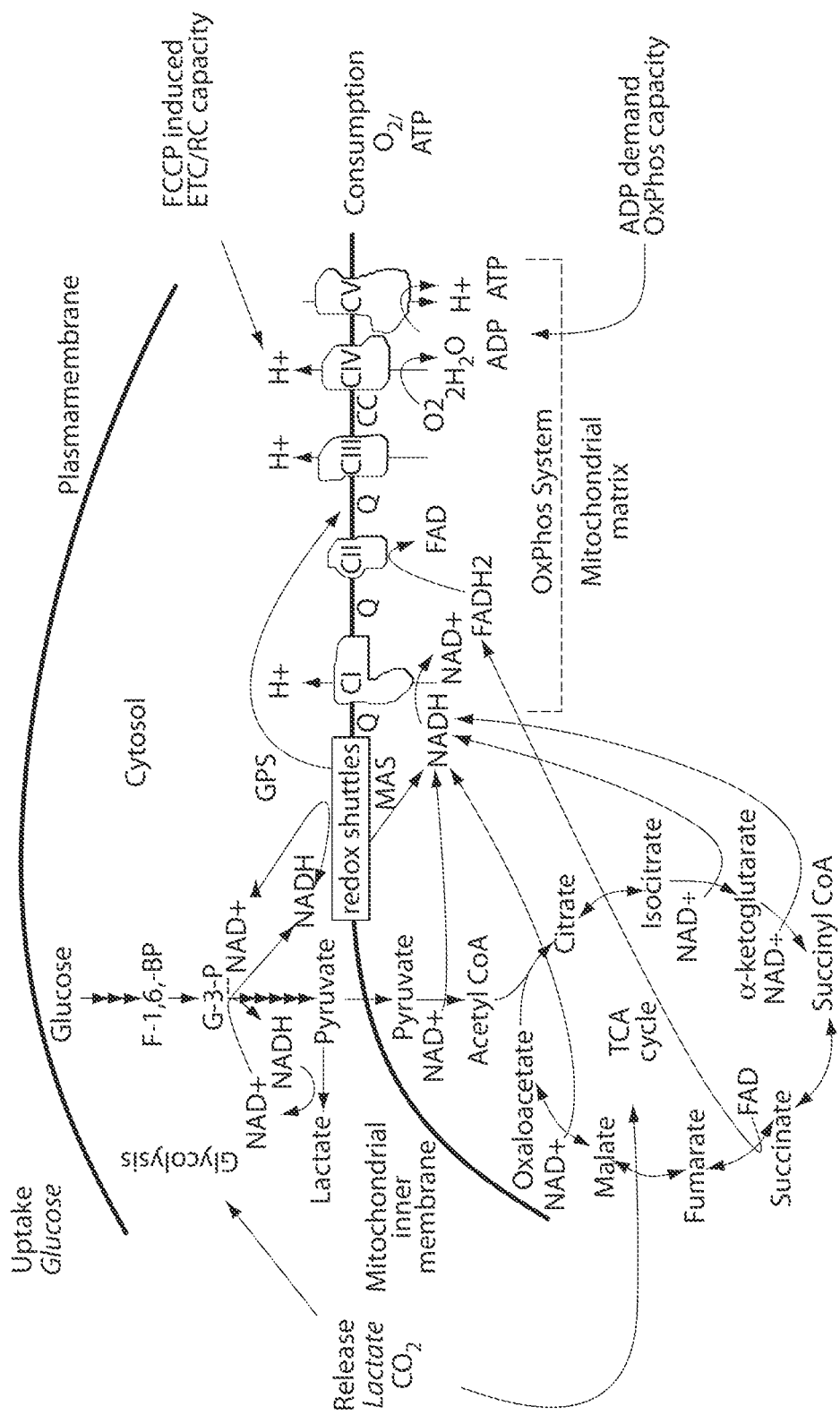
FIG. 1 provides a non-limiting overview of glucose metabolism in a typical mammalian cell. Relationships of the glycolysis, TCA cycle and OxPhos system are shown. The reactions generating and oxidizing NADH and $FADH_2$ are shown. CC: Cytochrome c; Q: ubiquinone; CI-V: OxPhos Complexes I-V; MAS: malate-aspartate shuttle: GPS: glycerol-3-phosphate shuttle. The measurements of lactate, $O_2$ and $CO_2$ levels in the immediate surroundings of cells are expected to give the rates of glycolysis, respiration and the TCA cycle.

In some embodiments, aspects of the invention relate to simple and reproducible assays for mitochondrial function. In some embodiments, one or more assay components can be provided as kits. Aspects of the invention relate to the surprising finding that cytolysin-based (e.g., perfringolysin O (PFO)-based) cell permeabilization eliminates the need for isolating mitochondria, and maintains the cellular microenvironment around mitochondria. This allows functional assays to be performed at close to physiological conditions.

According to some aspects, the invention relates to cholesterol-dependent cytolysins. As used herein, "cholesterol-dependent cytolysins" are members of a family of proteins that form pores in lipid-based membranes in a cholesterol sensitive manner. In some embodiments, cholesterol-dependent cytolysins are pore-forming toxins secreted by Gram-positive bacteria. In some embodiments, cholesterol-dependent cytolysins have a characteristic β-barrel structure. In some embodiments, cholesterol-dependent cytolysins are monomeric proteins that oligomerize on the membrane surface of target cells. In some embodiments, cholesterol-dependent cytolysins form a ring-like pre-pore complex at the membrane surface of target cells, and insert a large β-barrel into the membrane. In some embodiments, the presence of cholesterol in the target membrane is required for pore-formation. In some embodiments, cholesterol-dependent cytolysins selectively permeabilize cellular plasma membranes without damaging mitochondrial membranes. Non-limiting examples of cholesterol-dependent cytolysins are provided in Table 1. Other examples will be apparent to the skilled artisan. In particular embodiments, the cholesterol-dependent cytolysin is a perfringolysin O (PFO).

According to aspects of the invention, the selective permeabilization of cellular membranes by cholesterol-dependent cytolysins (e.g., PFOs) without damaging mitochondrial membranes can be used in assays to measure mitochondrial metabolites. Many mitochondrial metabolites readily cross the mitochondrial membrane to and from the cytosol. However, these metabolites do not readily cross the cellular membrane. This makes it difficult to assay these metabolites without disrupting the cells and in the process disrupting the natural physiological environment of the mitochondria. Surprisingly, cholesterol-dependent cytolysins (e.g., PFOs) have been found to permeabilize cellular membrane sufficiently to allow mitochondrial metabolites to enter and exit the cell. In some embodiments, this allows mitochondrial activity to be evaluated by measuring the extracellular levels of one or more mitochondrial metabolites. According to aspects of the invention, the selectivity of cholesterol-dependent cytolysins (e.g., PFOs) is useful, because it allows the cellular membrane to be permeabilized with respect to mitochondrial metabolites without disrupting the mitochondrial membrane. In some embodiments, this allows the activity of the mitochondria to be evaluated in their natural cellular environment.

According to some aspects of the invention, PFO-based cell permeabilization methods are provided for mitochondrial function assays. The methods are generally applicable across different cell types (e.g., established cell lines and primary cells). Kits that provide reagents for the methods are also provided herein. In some embodiments, these kits are useful for assays of Complexes I, II, III, IV and/or V, Oxidation Phosphorylation (OxPhos) capacity, and/or Respiratory (ETC/RC) capacity. Accordingly, in some embodiments, simple and reproducible assays for mitochondrial function are provided. In some aspects, the assays and kits provide diagnostic tools for mitochondrial dysfunction. In some embodiments, aspects of the invention are useful to understand the role of mitochondrial metabolism in pathophysiology. In some embodiments, aspects of the invention provide diagnostic tools for mitochondrial disorders.

In some embodiments, cholesterol-dependent cytolysin-based (e.g., PFO-based) cell permeabilization eliminates the need for isolating mitochondria, and maintains the cellular microenvironment around them. This permits mitochondrial function assays to be performed at close to physiological conditions using assays techniques that involve measuring the uptake, release, consumption, and/or production of cellular metabolites (e.g., mitochondrial metabolites), for example, using microplate-based respirometry. This also permits examination of the effects of membrane impermeable agents on mitochondrial function.

TABLE 1

Non-Limiting Examples of Cholesterol-Dependent Cytolysins

| PLYLUM Firmicutes CLASS Bacilli ORDER Bacillales FAMILY Bacillaceae | ID | % Identity | % Similarity | Length | Accession # |
|---|---|---|---|---|---|
| GENUS | | | | | |
| *Bacillus* SPECIES | | | | | |
| *B. anthracis* | ALO | 72 (68) | 88 (83) | 462 (512) | ZP_03017964.1 |
| *B. thurigiensis* | TLO | 74 (69) | 88 (83) | 462 (512) | YP_037419 |
| *B. cereus* | CLO | 74 (69) | 88 (84) | 462 (512) | YP_002369889.1 |
| *B. weihenstephanensis* | WLO | 74 (69) | 87 (83) | 462 (512) | ABY46062 |
| Listeriaceae *Listeria* | | | | | |
| *L. monocytogenes* | LLO | 43 (40) | 66 (62) | 469 (529) | DQ838568.1 |
| *L. seeligeri* | LSO | 45 (41) | 67 (63) | 469 (530) | P31830.1 |
| *L. ivanovii* | ILO | 46 (43) | 66 (62) | 469 (528) | AAR97343.1 |
| Planococcaceae *Lysinibacillus* | | | | | |
| *L. sphaericus* | SPH | 76 (72) | 90 (87) | 463 (506) | YP_001699692.1 |
| Paenibacillaceae *Paenibacillus* | | | | | |
| *P. alvei* | ALV | 75 (71) | 87 (84) | 462 (501) | P23564 |
| *Brevibacillus* | | | | | |
| *B. brevis* | BVL | 73 (69) | 88 (84) | 464 (511) | YP_002770211.1 |
| Lactobacillales Streptococcaceae *Streptococcus* | | | | | |
| *S. dysgalactiae** | SLOe | 67 (56) | 83 (70) | 463 (571) | BAD77791 |
| *S. pyogenes* | SLO | 67 (56) | 83 (70) | 463 (571) | NP_268546.1 |
| *S. canis* | SLOc | 66 (55) | 82 (69) | 463 (574) | Q53957 |
| *S. pseudonemoniae* | PSY | 46 (43) | 67 (63) | 466 (471) | ACI76900 |
| *S. pneumonia* | PLY | 46 (43) | 67 (64) | 466 (471) | ABO21366.1 |
| *S. mitis* | MLY | 46 (43) | 67 (63) | 466 (471) | ABK58695 |
| *S. suis* | SLY | 41 (40) | 65 (63) | 465 (497) | ABE66337.1 |
| *S. intermedius* | ILY | 41 (37) | 65 (59) | 469 (532) | B212797.1 |
| *S. mitis* (Lectinolysin) | LLY | 39 (29) | 62 (47) | 463 (665) | BAE72438.1 |
| Clostridia Clostridiales Clostridiaceae *Clostridium* | | | | | |
| *C. perfringens* | PFO | | | 463 (500) | NP_561079 |
| *C. butyricum* | BRY | 69 (65) | 85 (82) | 462 (513) | ZP_02950902.1 |
| *C. tetani* | TLY | 60 (55) | 78 (72) | 464 (527) | NP_782466.1 |
| *C. botulinum*B | BUYb | 60 (49) | 78 (63) | 464 (602) | YP_001886995.1 |
| *C. botulinum* E3 | BLYe | 60 (48) | 77 (60) | 464 (602) | YP_001921918.1 |
| *C. botulinum*C | BLYc | 60 (56) | 79 (74) | 463 (518) | ZP_02620972.1 |
| *C. novyi* | NVL | 58 (54) | 78 (73) | 463 (514) | YP_878174.1 |
| Actinobacteria Actinobacteria Bifidobacteriales Bifidobacteriaceae *Gardenella* | | | | | |
| *G. vaginallis* | VLY | 40 (39) | 65 (60) | 466 (516) | EU522488.1 |
| Actinomycetales Actinomycetaceae *Arcanobacterium* | | | | | |
| *A. pyogenes* | PLO | 41 (38) | 60 (56) | 469 (534) | U84782.2 |

Perfringolysin O [*Clostridium perfringens* str. 13]
gi|18309145|ref|NP_561079.1|

(SEQ ID NO: 1)
MIRFKKTKLIASIAMALCLFSQPVISFSKDITDKNQSIDSGISSLSYNRN

EVTLASNGDKIESFVPKEGKKTGNKFIVVERQKRSLTTSPVDISIIDSVN

DRTYPGALQLADKAFVENRPTILMVKRKPININIDLPGLKGENSIKVDDP

TYGKVSGAIDELVSKWNEKYSSTHTLPARTQYSESMVYSKSQISSALNVN

AKVLENSLGVDFNAVANNEKKVMILAYKQIFYTVSADLPKNPSDLFDDSV

TFNDLKQKGVSNEAPPLMVSNVAYGRTIYVKLETTSSSKDVQAAFKALIK

NTDIKNSQQYKDIYENSSFTAVVLGGDAQEHNKVVTKDFDEIRKVIKDNA

TFSTKNPAYPISYTSVFLKDNSVAAVHNKTDYIETTSTEYSKGKINLDHS

GAYVAQFEVAWDEVSYDKEGNEVLTHKTWDGNYQDKTAHYSTVIPLEANA

RNIRIKARECTGLAWEWWRDVISEYDVPLTNNINVSIWGTTLYPGSSITY

N

Oxidative Phosphorylation (OxPhos)

Figure 15:
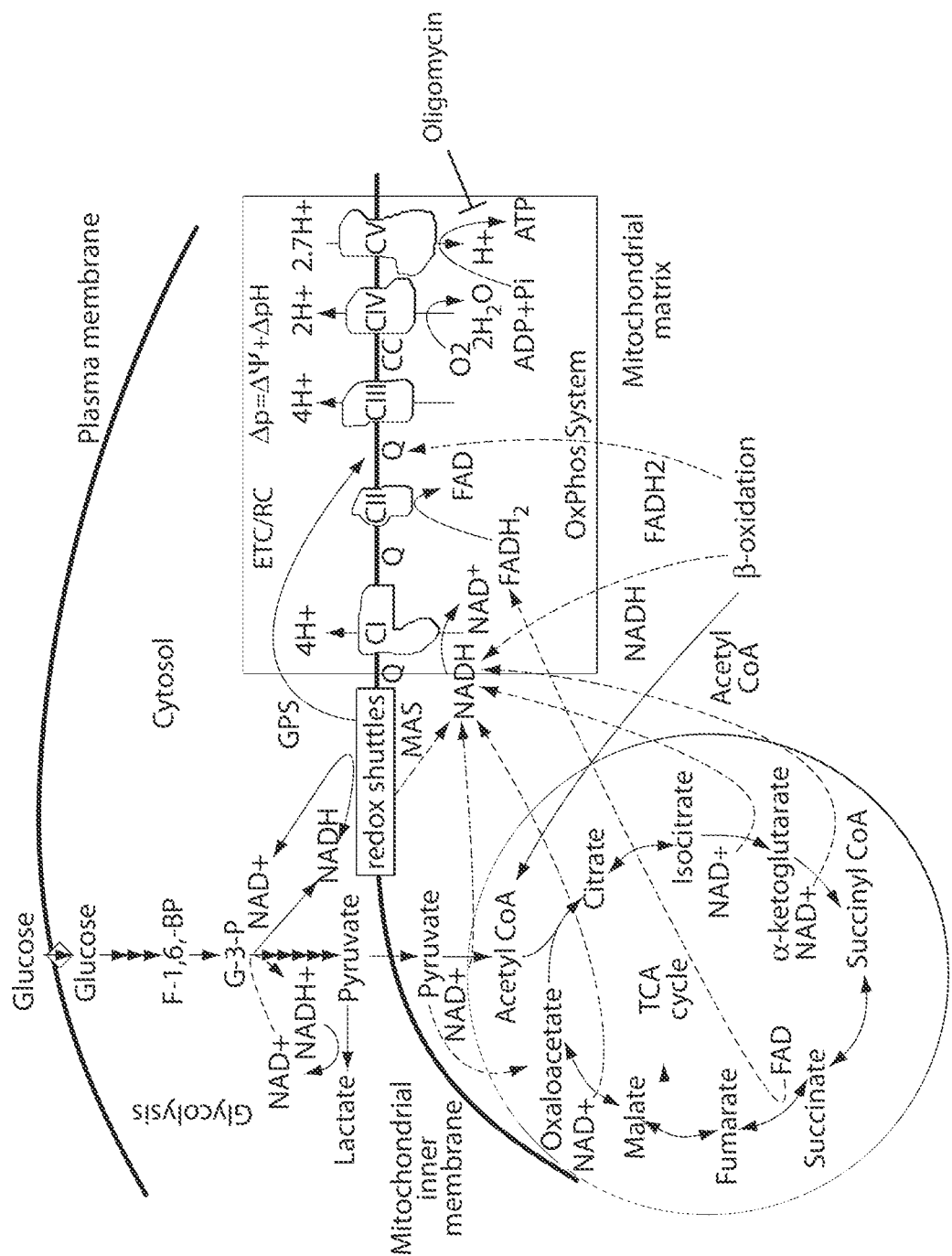
FIG. 15 shows inter-relationships among the glycolysis, TCA cycle and OxPhos. Emphasis is given to reactions that generate electron donors such as NADH and FADH$_2$ to support OxPhos as indicated. The NADH and FADH$_2$ generating reactions are shown by broken lines, while those consuming them are shown by solid lines. Reversible reactions are shown by lines with arrowheads on both ends. F-1, 6-BP, fructose-1, 6-bisphosphate; G-3-P, glyceraldehyde-3-phosphate; GPS: glycerol-3-phosphate shuttle; MAS: malate aspartate shuttle; CI-V: OxPhos complexes I-V; .p: proton motive force; mitochondrial membrane potential; pH: pH difference across mitochondrial inner membrane; Pi: inorganic phosphate; Q: ubiquinone.

OxPhos, one of the key functions of mitochondria, is carried out by five multimeric enzyme complexes (I-V, see below) with the help of electron donors (NADH, & $FADH_2$) and electron carriers (ubiquinone, Cytochrome c). The NADH and $FADH_2$ feed electrons to the electron transport/respiratory chain (ETC/RC) that establishes an electrochemical gradient ($\Delta p = \Delta \psi_m + \Delta pH$) across the inner mitochondrial membrane called proton motive force ($\Delta p$). The $\Delta p$ is the driving force for ATP synthesis using ADP and Pi. Four enzyme complexes constitute the ETC/RC. Complex I is NADH-ubiquinone oxidoreductase; Complex II is succinate-ubiquinone oxidoreductase; Complex III is ubiquinol-Cytochrome c oxidoreductase; and Complex IV is Cytochrome c-ubiquinone oxidoreductase. Coupled electron transfer with proton translocation across the mitochondrial membrane by Complexes I, III, and IV establishes $\Delta p$, which drives ATP synthesis using the ATP synthase (Complex V) (see FIGS. 1 and 15). Primarily, the ETC/RC function is supported by mitochondrially generated NADH and FADH2 from the oxidative metabolism of pyruvate via the tricarboxylic acid (TCA) cycle. Under certain circumstances, 13-oxidation of fatty acids and amino acids' metabolism also contribute to mitochondrial NADH/$FADH_2$ pool. Often, the pyruvate oxidative metabolism predominates. Thus, the oxidation of other substrates is tightly regulated based on the physiological context of a given cell. NADH is also generated within cytosol from the reaction of glyceraldehyde-3-phosphate dehydrogenase (GAPDH). The metabolic flux through GAPDH is dependent on continuous NADH oxidation to regenerate NAD+ that supports GAPDH function. Within the cytosol the NADH is regenerated by lactate dehydrogenase (LDH) and by NADH redox shuttling using the malate-aspartate (MAS) and glycerol-3-phosphate (GPS) shuttles (see FIG. 1). The relative contribution of LDH and redox shuttles in regenerating NAD+ is a consideration in different cell types and tissues under normal and pathophysiological conditions.

Mitochondrial Dysfunction and Disease:

Impairments in OxPhos are often referred to as mitochondrial dysfunction (and are associated with mitochondrial disorders), and can result from hereditary and somatic mutations in nuclear genes or mtDNA, or functional impairments by drugs or toxins. Mutations in over 100 genes constituting the oxidative phosphorylation machinery are linked with mitochondrial encephalopathies in humans, which are the most common metabolic diseases with an incidence of over ~1/5000 in live births. Respiratory chain Complex I deficiency is a cause of mitochondrial diseases in many cases. Twenty five of at least fifty known genes implicated in Complex I biogenesis are found associated with mitochondrial diseases. Pathogenic mutations in structural subunits (e.g., NDUFA1, 2, 11; NDUFS1-4, 6-8; NDUFV1,2) and assembly factors (e.g., NDUFAF1-6) have been identified. Neurodegenerative diseases such as Parkinson's disease, Alzheimer's disease, and Huntington's disease are also associated with mitochondrial dysfunction. Further, mtDNA mutations are found associated with almost all types of cancers. Type 2 diabetes is also linked with declining mitochondrial function in relevant tissues such as β-cells and muscles. Type 2 diabetes represents a major clinical challenge due to the sharp rise in obesity-induced disease. Thus, in some embodiments, methods are provided for accurate assessment of mitochondrial function in the context of pathophysiology.

Mitochondrial Function Assays:

Plasma membrane permeabilization removes the permeability barrier of cells and allows accurate estimation of mitochondrial function in intact cells. The selective permeabilization of the plasma membrane has been achieved by exploiting the differential distribution of the cholesterol in membranes. Because most cholesterol is present in the plasma membrane, intracellular membranes are expected to remain largely untouched by cholesterol dependent pore forming agents. Thus, it is possible to selectively permeabilize the plasma membrane in the presence of cholesterol-dependent pore forming agents. Disclosed herein are mitochondrial function assay methods based on a method of cell permeabilization, using a cholesterol dependent pore forming protein (e.g., perfringolysin O (PFO) from *Clostridium perfringens*). The mechanism of pore formation by PFOs has been characterized.

Applications:

In some embodiments, methods and kits disclosed herein are useful with systems for analyzing extracellular flux (XF) (e.g., commercially available extracellular flux (XF) analyzers, e.g., available from Seahorse Bioscience) to assess mitochondrial function in cells. In some embodiments, users of such analyzers who investigate bioenergetic pathways isolate cells or tissue, adhere them to a culture plate, and perform bioenergetic assessments. These techniques may be used to provide valuable information and insight into mitochondrial biology, under conditions that allow for experimental control of the substrate supply and demand. According to aspects of the invention, whole cells may be selectively permeabilized directly in the plates (e.g., XF plates), allowing for control over substrate supply and demand, access to both oxidative phosphorylation and respiratory chain components, as well as eliminating the need to go through complicated and potentially damaging mitochondrial isolation techniques.

Kits:

In some embodiments, cholesterol-dependent cytolysins and assay-specific reagents are packaged into a kit format. In some embodiments, the kit design may vary with respect to specific assays rather than cells types. In some embodiments, these kits are designed to address specific aspects of mitochondrial metabolism such as the OxPhos, TCA cycle, and cell-specific OxPhos/TCA cycle features. Kits are provided for Complex I-IV assays, OxPhos capacity and ETC/RC capacity assays.

Assays for Complex I, II, and OxPhos & ETC/RC capacities are disclosed herein and corresponding kits are provided in some embodiments. In some embodiments, ADP-stimulated respiration is a measure of the Complex V activity, e.g., when the substrates are not limiting. In some embodiments, the use of succinate with glycerol-3-phosphate together ensures that the ETC/RC activity is not limiting factor, and thus the ADP-stimulated, oligomycin-sensitive respiration is the output of Complex V function. Similarly, in some embodiments, the carboxyatractiloside-sensitive respiration gives the functional output of the ATP/ADP nucleotide translocator (ANT). In some embodiments, the activity of Complex III is assayed using glycerol-3-phosphate+succinate supported, Antimycin A-sensitive respiration. Likewise, the activity of Complex IV is assayed in some embodiments using ascorbate+TMPD supported, KCN-sensitive respiration as described. In some embodiments, a kit has components selected from: PFO, ADP, FCCP and assay buffer.

The actual concentration of reagents will typically vary with the experimental design (e.g., 24-well vs. 96-well assay format) and the number of assays. PFO can typically be used in a range of 1-100 nM. ADP can typically be used in a range of 1-2 mM. And FCCP can typically be used in a range of 2-4 µM. The components are typically provided as 100-1000-fold concentrated stocks, which can be used at desired concentrations within the recommended range by the user to get the maximal mitochondrial performance within the assays.

It should be appreciated that a kit may include one or more components (e.g., one or more substrates or inhibitors) for a specific Complex assay (e.g., one of Complex I-V) along with a cholesterol-dependent cytolysin (e.g., PFO), and optionally one or more reducing agents (e.g., DTT or other suitable reducing agent). The different components may be provided in separate containers in a kit. However, in some embodiments, two or more different components may be combined in a single container (e.g., sample tube, well, etc.). Table 2 provides non-limiting examples of components of kits for mitochondrial complexes.

TABLE 2

Non-Limiting Examples of Components of Kits for Mitochondrial Complexes

| Complex | Substrate | Inhibitor |
|---|---|---|
| Complex I: | glutamate (G); pyruvate (P), malate (M), isocitrate (I) and alpha-ketoglutarate (K) in different combinations; commonly used are glutamate + malate (GM), or pyruvate + malate (PM); PM; GM, PGMIK; GMIK combinations). | Rotenone |
| Complex II: | Succinate (S) | malonate |
| Complex III: | Glycerol 3-phosphate | Antimycin A |
| Complex IV: | TMPD + Ascorbate | KCN |
| Complex V: | Succinate (with or without glycerol-3-phosphate) + ADP | Oligomycin |

Microplate-Based Respirometry:

In some embodiments, functional assays will be based on a microplate-based system or device, for example using the extracellular flux (XF) analyzer from Seahorse Biosciences. In some embodiments, wild type PFO and/or its variants will be used for selective plasma membrane permeabilization to eliminate the substrate transport barrier, and characteristics of mitochondrial performance (e.g., maximal mitochondrial performance) can be determined. Methods for assaying specific mitochondrial functions that work across different cell types can be implemented. In some embodiments, one or more microplates may be preloaded (and/or provided) with one or more assay components (e.g., substrates, inhibitors, etc.) and one or more cholesterol-dependent cytolysins (e.g., PFO), and optionally one or more reducing agents (e.g., DTT or other suitable reducing agent).

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

Exemplary embodiments of the invention will be described in more detail by the following examples. These embodiments are exemplary of the invention, which one skilled in the art will recognize is not limited to the exemplary embodiments.

EXAMPLES

Example 1: Experimental Design and Methodology

PFO-Based Cell Permeabilization Methods for Mitochondrial Function Assays:

Wild type PFOs and variants have been tested for maximal mitochondrial performance (see Table 1 for examples of PFOs) using methods disclosed herein. Specific assays for different OxPhos components applicable to a wide variety of were developed based on cell permeabilization methods described herein. Both established and primary cells were utilized to test the general applicability of PFO-based assays.

It has been recognized that a reducing agent may be used to increase shelf life of wild-type PFO. PFO contains only one Cys residue at position 459. To avoid the need of a reducing agent in permeabilization reactions, a Cys free derivative, $PFO^{C459A}$, has been used. This variant has activity comparable to wild type PFO. A mutant $rPFO^{T319C-V334C}$ provides for conditional cell permeabilization, as it does not form pore in the membrane following insertion until a reducing agent, such as DTT is added. After treatment with $rPFO^{T319C-V334C}$ the cells may be washed to remove the protein before the experiment.

TABLE 3

PFO variants and their properties: To simplify the mutation notation, all derivatives that include C459A mutation will be called rPFO.

Figure 9:
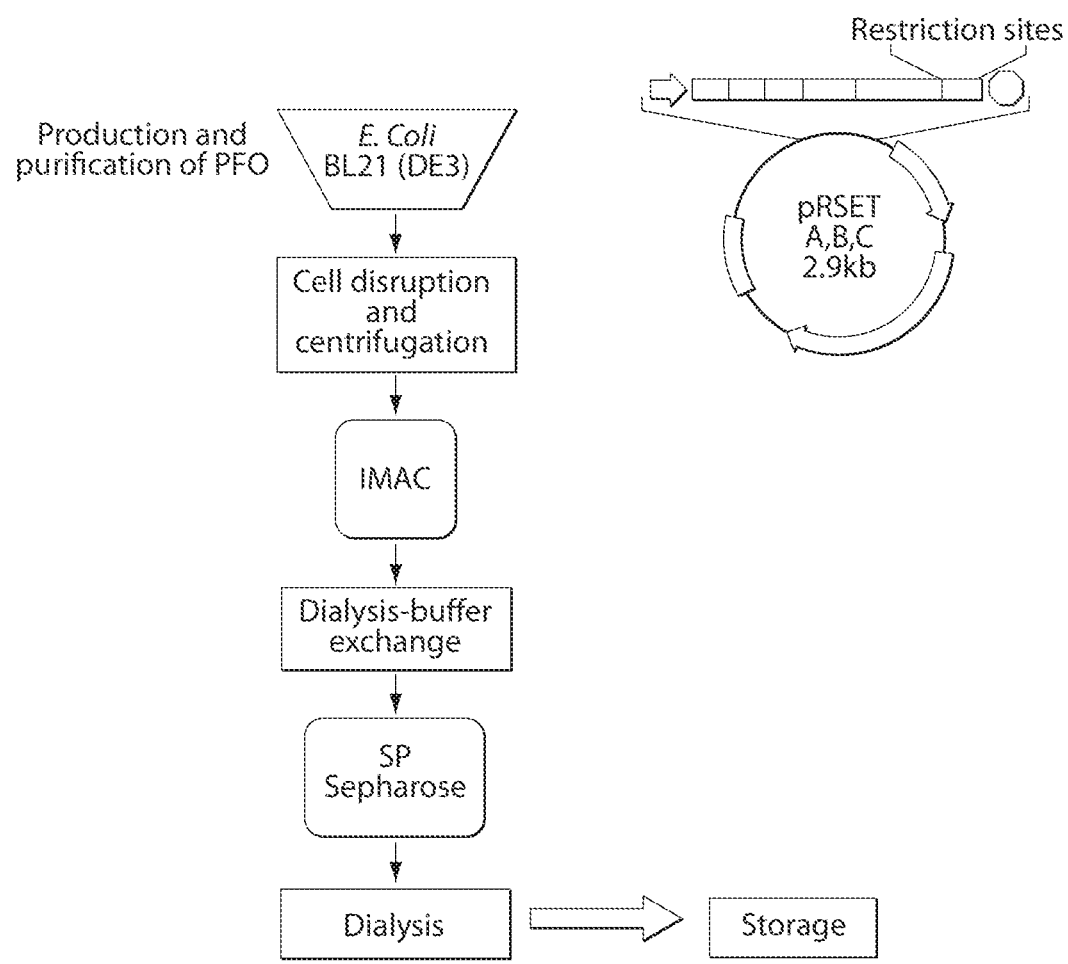
FIG. 9 provides an overview of a PFO purification scheme.
Figure 10:
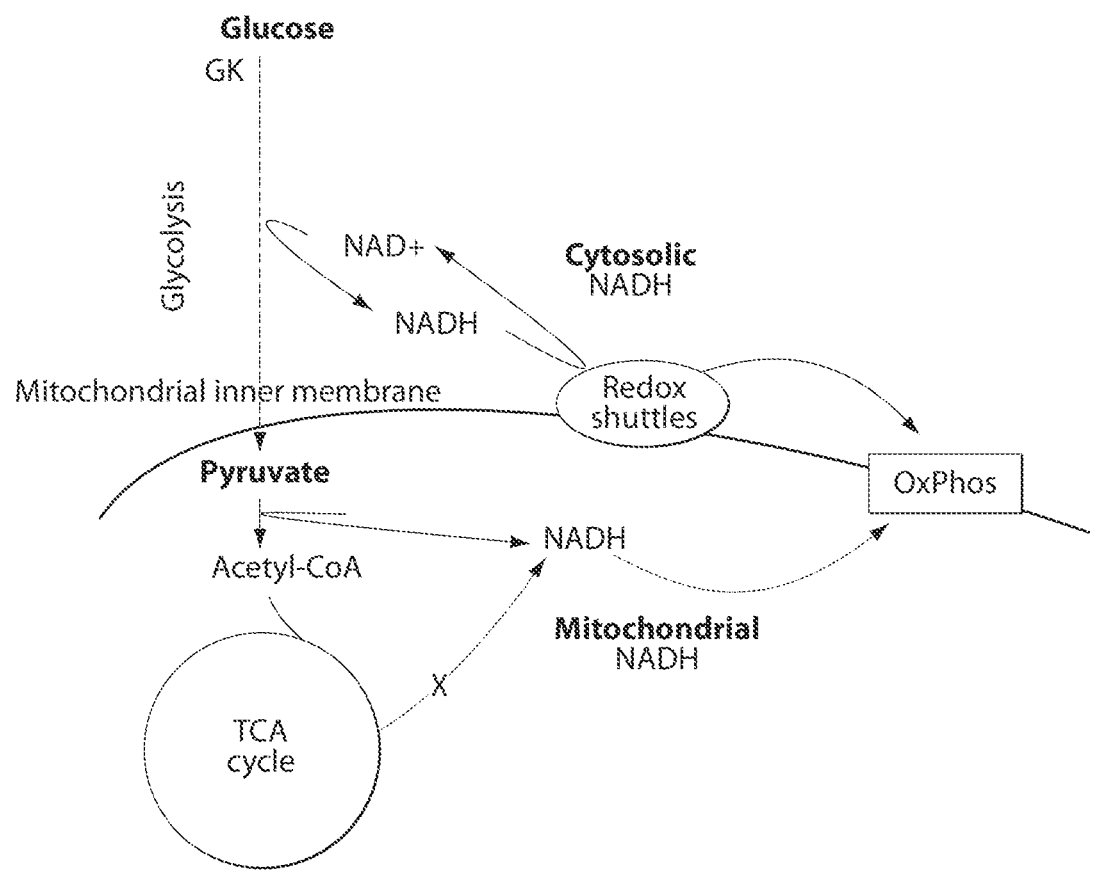
FIG. 10 provides an outline of a working model showing that β-cell respiration is primarily supported by the redox shuttles when cells are intact. Complex I-dependent respiration should drop significantly when β-cells are permeabilized if it is primarily supported by redox shuttle.
Figure 11A:
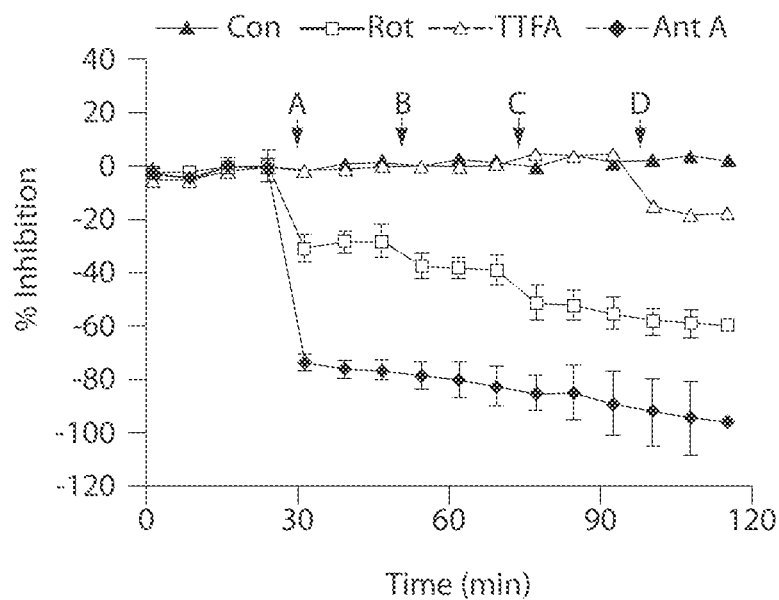
FIGS. 11A and 11B show that β-cells display low level of Complex I-dependent respiration.
Figure 11B:
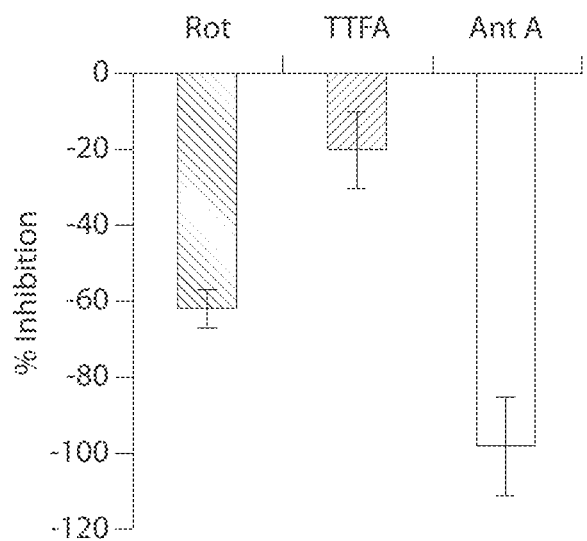
Figure 12A:
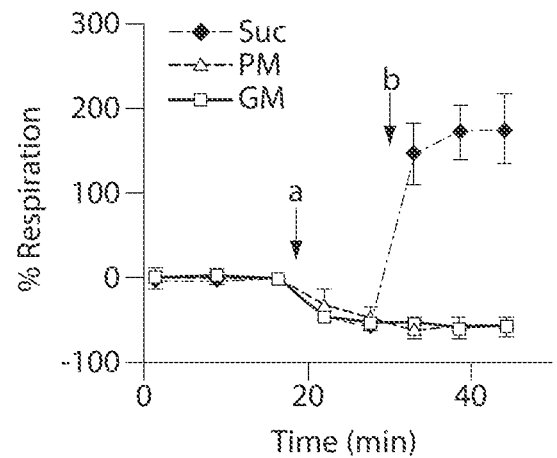
FIGS. 12A-12D show that permeabilized β-cells do not display Complex I-dependent respiration.
Figure 12B:
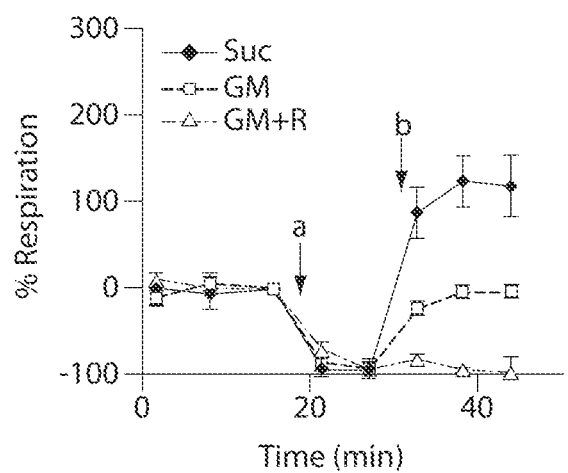
Figure 12C:
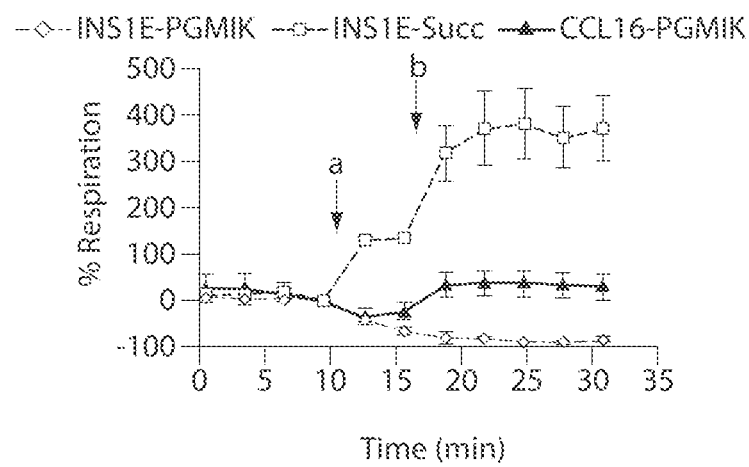
Figure 12D:
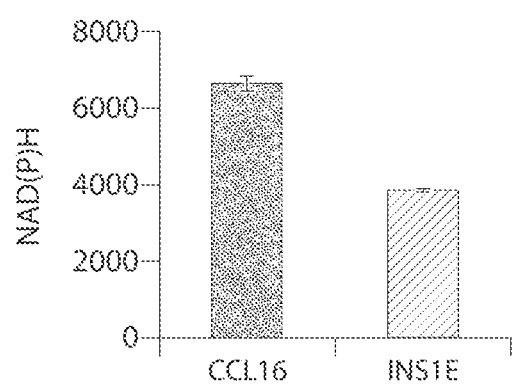
Figure 13A:
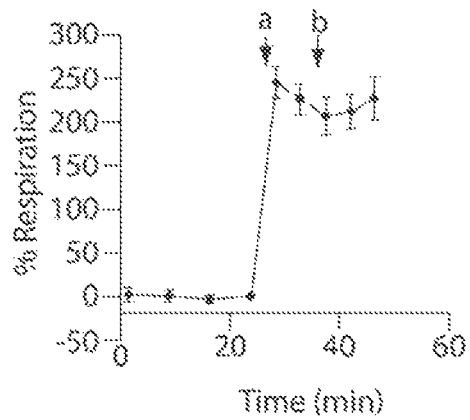
FIGS. 13A-13C show that β-cell's relative respiratory (ETC/RC) and oxidative phosphorylation (OxPhos) capacities are comparable across cell types.
Figure 13B:
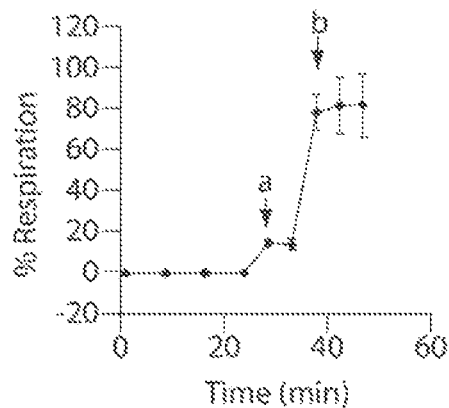
Figure 13C:
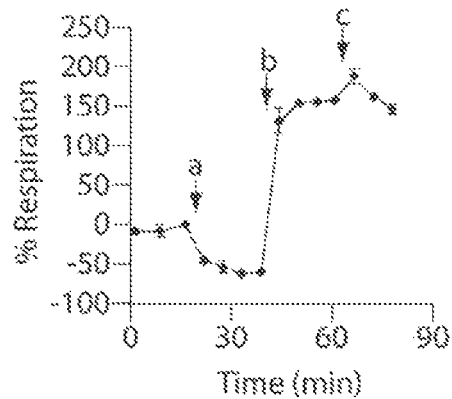
Figure 14A:
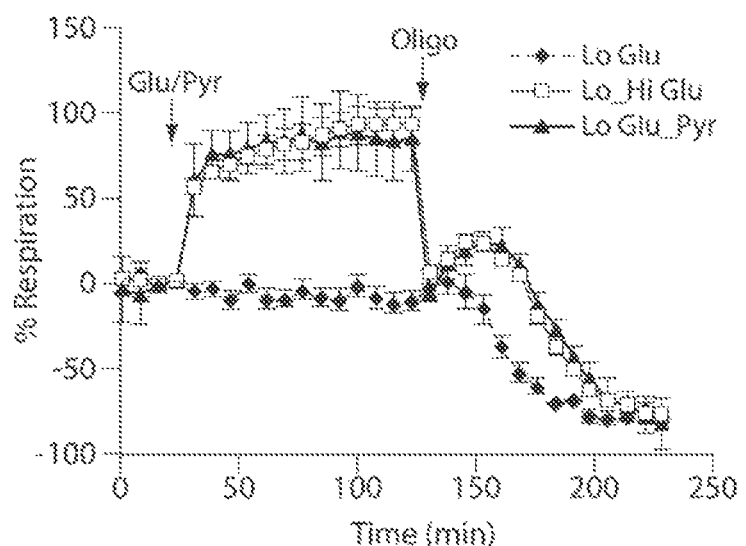
FIGS. 14A and 14B show that β-cell respiration gradually declines when oxidative phosphorylation is inhibited. Test of substrate limitation vs. respiratory chain dysfunction.
Figure 14B:
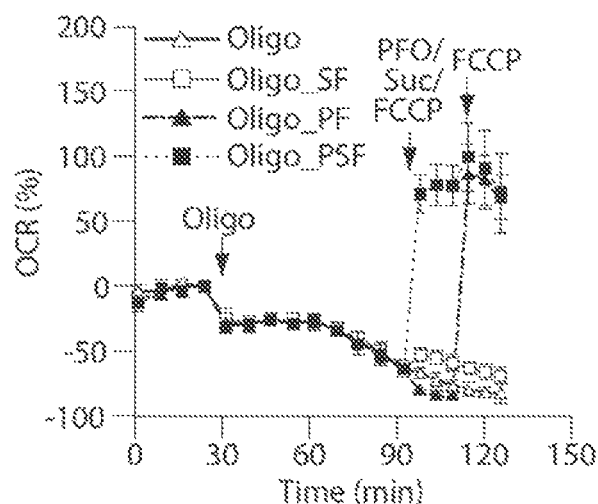

| PFO derivative | Characteristic | Pore formation | SEQ ID NO: |
|---|---|---|---|
| PFO (nPFO) | Wild type/native protein | Yes | 8 |
| rPFO | Recombinant, Cys less derivative of PFO ($PFO^{C459A}$); cholesterol binding may be reduced slightly | Yes | 9 |
| $rPFO^{T319C-V334C}$ | Monomeric binding | Yes, triggered by DTT | 11 | a) Preparation of Functional PFO:

A non-limiting purification scheme that has been used for obtaining recombinant PFO (e.g., wild-type or variant) is illustrated in FIG. 9. Briefly, the scheme involves over-expressing a PFO protein and/or its variants with a His-Tag for affinity purification. In some embodiments, *E. coli* BL21 (DE3) (Invitrogen) cells expressing PFO and rPFOs conditionally are grown in 2 L cultures at 37° C. with constant agitation. Expression of the PFO/rPFO are induced by the addition of isopropyl α-D-thiogalactopyranoside (IPTG, Gold Biochemicals, St. Louis, Mo.) to a final concentration of 1 mM when the turbidity of the culture at 600 nm reaches 0.5-0.6. After 3 h of induction, cells are harvested by centrifugation (4,400 g, 15 min. 4° C.). The cell pellets are suspended in a total of 25 mL of buffer B [10 mM MES (2-(N-morpholino)-ethanesulfonic acid) (pH 6.5), 150 mM NaCl] in the presence of protease inhibitors, PMSF and benzamidine at a concentration of 50 mg/mL. The cells are lysed by one passage through a French pressure cell (1 in. diameter piston, Aminco, Silverspring, Md.) at 15,000 psi.

After clearing the cell lysate by centrifugation at 31,000 g for 15 min. 4° C., the supernatant is loaded onto a column (1.5 cm I.D.×10 cm) containing chelating Sepharose Fast Flow (GE Healthcare, Piscataway, N.J.) that had been pre-loaded with $Ca^{2+}$ and equilibrated with buffer B at room temperature. The column is washed with 115 mL of buffer B (2 mL/min), and a linear gradient 0 to 50 mM imidazole pH 6.5 to remove additional contaminating proteins. The bound PFO/rPFO is eluted with 55 mL of buffer B containing 300 mM imidazole.

The pooled fractions containing the bulk of the protein are dialyzed overnight at 4° C. against 4 L of buffer C [10 mM MES (pH 6.5), 1 mM EDTA], and loaded directly onto a SP Sepharose lip (GE Healthcare, Piscataway, N.J.) cation exchange column (1.5 cm I.D.×10 cm) equilibrated with buffer C. The column is washed with 60 mL, of buffer B (3 mL/min), and 30 mL of 0.1 M NaCl in buffer C before the elution of the PFO/rPFO with a 100 mL linear gradient (3 mL/min) from 0.1 to 0.9 M NaCl in buffer C. PFO eluted at ~0.5 M NaCl and the pooled fractions containing the PFO are dialyzed against buffer A made 10% (v/v) in glycerol, aliquoted into cryovials, quick-frozen in liquid nitrogen, and stored at −80° C. Dithiothreitol (5 mM) is included as a reducing agent when purifying PFO derivatives containing Cys residues. Cys-less derivatives (rPFO) do not need DTT additions.

b) Optimization of the Conditions for Different Mitochondrial Function Assays:

A general methodology for Complex I, II, V, OxPhos capacity, and ETC/RC capacity has been developed. These assays can be implemented with a variety of cell types such as peripheral blood monocytes, myoblasts, neurons, astrocytes, and synaptosomes. In some embodiments, cell-specific modifications may be utilized for certain proteins. The modifications may depend upon the buffer conditions and supplements used. In some embodiments, low $K^+$ containing buffer was found to be advantageous for mitochondrial functional assays, e.g., in assays using INS1E cells. Similar buffers may be suitable for use with other cell types in certain contexts. However, the relative level of different ions (including $K^+$) may be optimized for different cell types in some instances.

To evaluate conditions for primary cells in the context of pathophysiology, a mouse model (Ndufa1$^{S55A}$) of the partial Complex I deficiency (~50%) may be used. As disclosed in Example 11, primary cells (neurons, mouse embryonic fibroblasts, blood monocytes, thymocytes and splenocytes) and synaptosomes may be derived from the Ndufa1$^{K1}$ mice to determine the physiological effects of partial Complex I assembly. Partial Complex I deficiencies are the most common cause of mitochondrial diseases in humans. However, other deficiencies also may be studied using these methods.

Example 2: Experimental Evaluations Using Different Cell Types

Similar experimental conditions may be used for assays of Complexes I-V, and OxPhos and ETC/RC capacity and across different cells (see Table 4 for a non-limiting list of cells).

TABLE 4

Cells for PFO-based mitochondrial function assays.

| Category | Subcategory | Cells | |
|---|---|---|---|
| Cell lines | Adherent cells | HEK293, C2C12, HepG2, A549, H460, MCF7 | |
| | Adherent cells with coating | INS1, SHSY-5Y | |
| | Non-adherent cells | Cell seeding, spin down, and measurements on same day with above cells | |
| | | Cells may be grouped with respect to their OxPhos capacity vs. ETC/RC capacity to provide a reference for each enlisted cell line. | |
| Primary cells | Adherent cells | β-cells, astrocytes, neurons, fibroblasts, hepatocytes, mammary epithelial cells, myocytes/blasts (cardiac, skeletal), Adipocytes (WAT/BAT), adult stem cells | Note: primary cells may require coating of plates (e.g., V7 plates) with PEI or similar reagents e.g. PDL, CellTak. |
| | Non-adherent cells with coatings | Peripheral blood monocytes (PBMCs)/Lymphocytes (T & B cells) | May involve coating of plates with PEI or similar reagents e.g. PDT, CellTak |
| | Others | Synaptosomes | Spun down in PIE-coated plates (e.g., V7 plates) |
| Cells may be grouped with respect to their OxPhos capacity vs. respiratory (ETC/RC) capacity to provide a reference for each enlisted cell line. For example excitable cells, such as β cells, neurons and muscle cells have comparable OxPhos vs. respiratory (ETC/RC) capacity under low inorganic phosphate (Pi) medium/buffer. Under the same conditions non excitable cell such as fibroblasts have lower OxPhos capacity compared to respiratory capacity. Increasing the Pi concentration to 10 mM significantly increases the OxPhos capacity in these cells, but it is still relatively lower than respiratory capacity. | | | |

The conditions for XF-based respirometry have been evaluated with mammary epithelial cells and adult stem cells. Similar experiments may be performed with other cells. For example, different primary cells, such as mammary epithelial cells, mouse embryonic fibroblasts, can be used. In some embodiments, based on experiments with primary neurons and astrocytes, these primary cells can be derived from the Ndufa1$^{S55A}$ mice. In some embodiments, it may be advantageous to optimize the concentrations of different assay components for different cell types. For example, it may be advantageous to grow excitable cells such as muscle cells, and neurons in the presence of different amounts $K^+$, $Ca^{2+}$ and/or carnitine than other cells. However, assays with β-cells, which are also excitable cells, indicate such cells may be evaluated effectively in a wide range of assay conditions. Testing these parameters for a given cell type is possible while using ADP-stimulated and succinate supported respiration as output response for the mitochondrial performance.

Example 3: Assay Using Digitonin as a Permeabilizing Reagent

Figure 2:
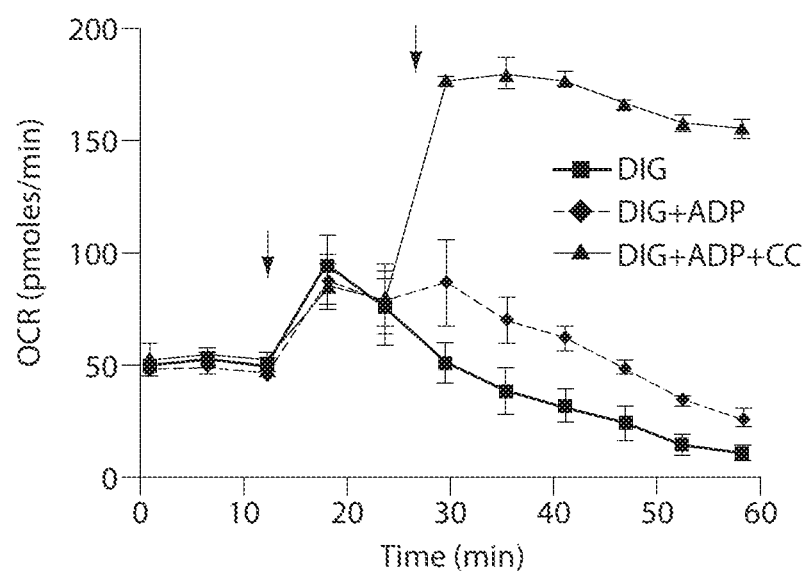
FIG. 2 illustrates digitonin (DIG)-based cell permeabilization. Respiration of INS1E was measured in Ca2+-free buffer containing succinate as substrate using the XF-analyzer. After measuring basal respiration rate, cells were permeabilized with DIG (1st arrow) and then ADP, with or without Cytochrome c (CC) was added ($2^{nd}$ arrow). Second additions were buffer, ADP, and ADP+CC for groups DIG, DIG+ADP, and D1G+ADP+CC respectively.

Digitonin concentration and respiration buffers were optimized for maximal ADP-stimulated respiration using succinate as substrate in the presence and absence of Cytochrome c. FIG. 2 shows representative data for conditions for INS1E cells that involve the addition of exogenous Cytochrome c. A $Ca^{2+}$-free low $K^+$ respiration buffer [20 mM TES pH7.4, 3.5 mM KCL, 120 mM NaCl, 0.4 mM $KH_2PO_4$, 1.2 mM $Na_2SO_4$, 2 mM $MgSO_4$, 1 mM EGTA with 0.4% fatty acid free BSA] was used unless otherwise specified. Since, the intracellular $K^+$ ion concentration is higher (~120 mM), $Ca^{2+}$-free high $K^+$ buffers (25-120 mM NaCl replaced with equimolar KCL in the buffer) were tested to determine if mitochondria performed better. It was found that in certain instances high $K^+$ buffers underperformed compared to the low $K^+$ buffer using INS1E cells. Under the same conditions, the performance of two other commonly used permeabilizing agents, saponin, and alamethicin, was evaluated; performance results were compared with digitonin. Although a comparable level of performance to digitonin was achieved using saponin and alamethicin, the assays were not very reproducible. These studies suggested that for each cell type, the digitonin concentration had to be optimized, and this was more variable across different species than within one particular species. Like other detergents, there were reproducibility issues with digitonin, which was believed to be due to the heterogeneity in pore formation, which cannot be effectively controlled with detergents. The requirement of exogenous Cytochrome c with detergent-based assays suggests that mitochondrial integrity is compromised, which results in the loss of Cytochrome c.

Example 4: PFO-Based Assays

Figure 3A:
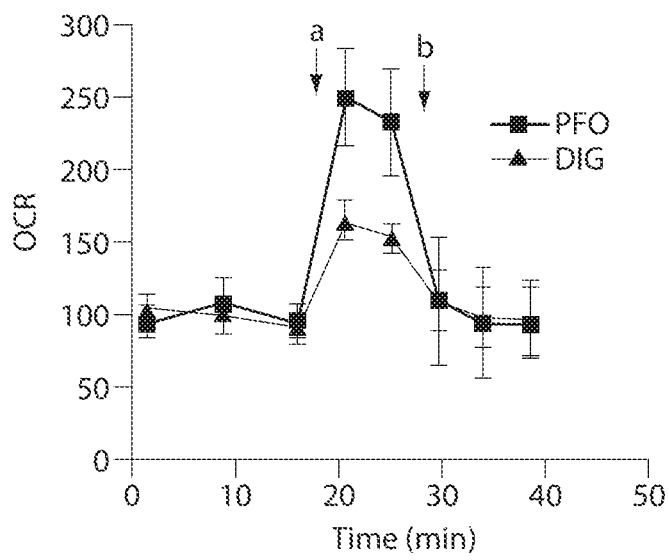
FIGS. 3A and 3B illustrate PFO performance compared with digitonin performance.
Figure 3B:
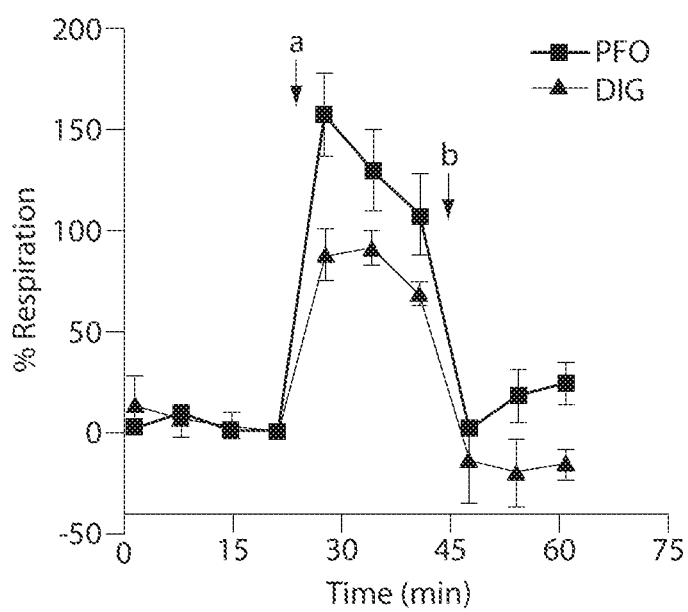
Figure 4:
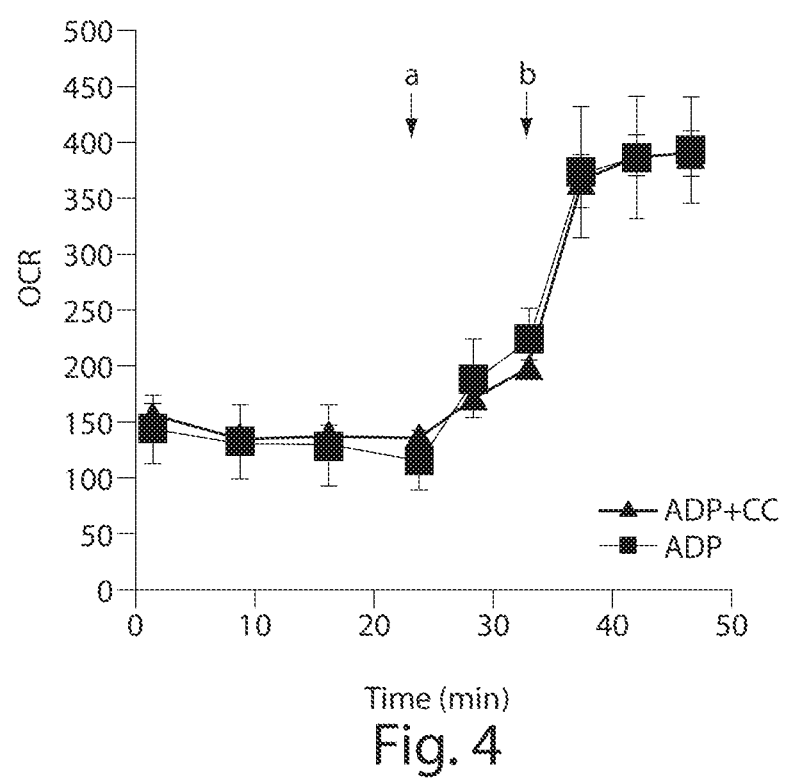
FIG. 4 shows that PFO-based assays do not need exogenous Cytochrome c. Succinate supported, ADP stimulated INS1E cells respiration is shown. Injections were as follows: "a" was nPFO, "b" was ADP with or without Cytochrome c.

A PFO-based assay was developed and found to overcome problems associated with digitonin-based assays. Initially, a wild type PFO was used for selective permeabilization of the plasma membrane. The performance of PFO was compared to digitonin in assays using INS1E cells and Chinese hamster lung fibroblasts, (V79-G3). Surprisingly, PFO outperformed digitonin in both cell types (see FIGS. 3A-3B). The need for exogenous Cytochrome c in PFO-based assays was evaluated. This was accomplished by comparing the ADP-stimulated respiration in the presence and absence of Cytochrome c. The tests showed that even lower concentrations of PFO could be used without the addition of Cytochrome c (FIG. 4).

The lack of exogenous Cytochrome c requirement in assays with PFO indicates that the mitochondrial integrity is better preserved with PFO relative to digitonin. Thus, further studies using PFO were carried out in the absence of Cytochrome c. Although the data shown here are for INS1E cells only, the conditions are applicable to different types of cells.

Figure 5A:
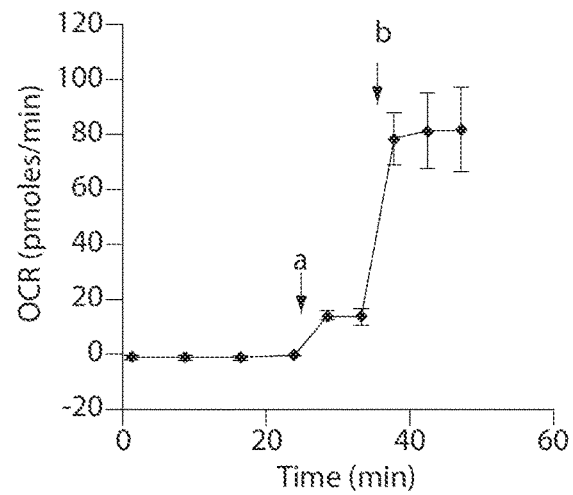
FIGS. 5A-5C illustrate OxPhos capacity and respiratory (ETC/RC) capacity. ADP- and FCCP-stimulated respirations give OxPhos and respiratory capacities, respectively.
Figure 5B:
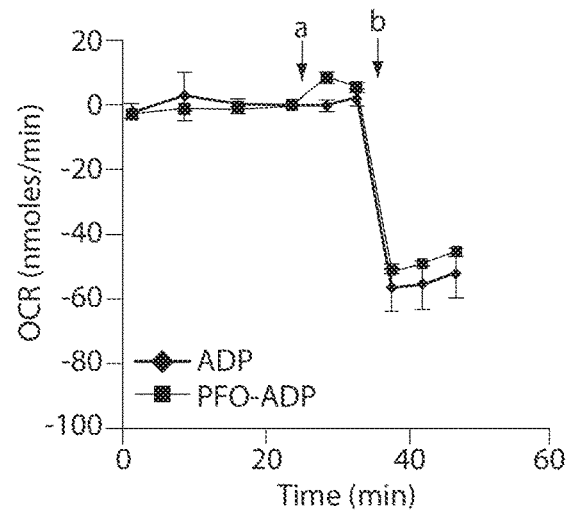
Figure 5C:
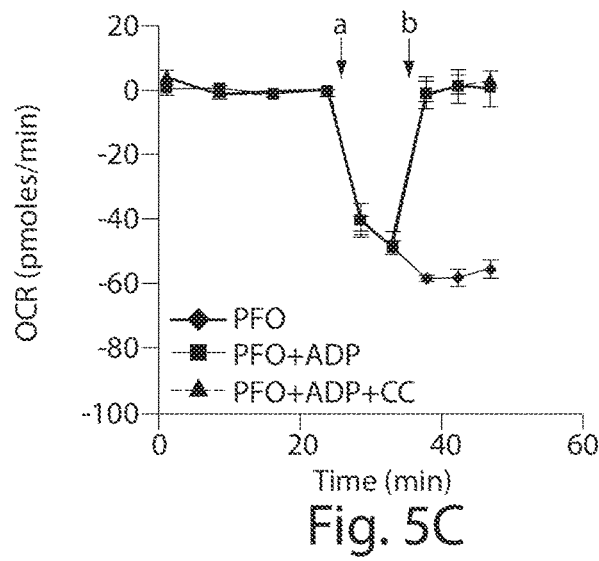
Figure 6A:
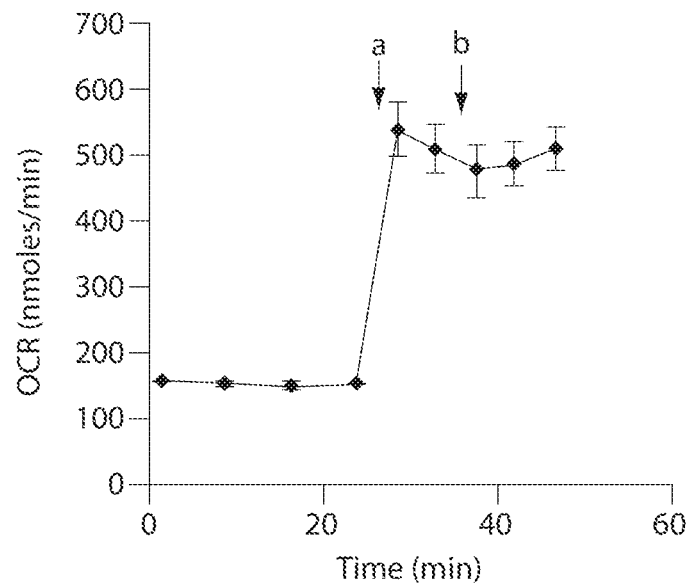
FIGS. 6A and 6B show comparable levels of ADP-stimulated and FCCP-stimulated respiration in rat pancreatic β cells.
Figure 6B:
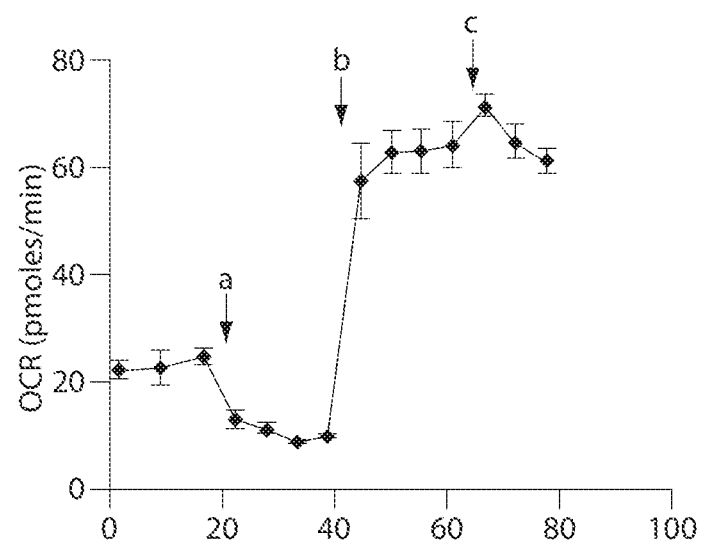

Example 5: Determination of the Spare Oxidative Phosphorylation (OxPhos) and Respiratory (ETC/RC) Capacities To compare the OxPhos and ETC/RC capacities of cells, cells were pre-incubated in Ca2+-free respiration buffer with substrates (e.g., 15 mM glucose and 10 mM succinate) and then respiration rates were measured. After measuring basal respiration rates, cells were permeabilized with PFO and then ADP- and FCCP-stimulated respiration rates were measured successively. In this way, the spare capacities of the OxPhos and ETC/RC were determined (FIG. 5A). Without the addition of ADP to PFO permeabilized cells, the respiration declined to a steady-state, and remaining respiration was supported only by the proton ($H^+$) leak across the mitochondrial inner membrane (FIGS. 5B & C). Addition of ADP stimulated respiration close to the basal respiration level, and the presence or absence of Cytochrome c did not appear to make a substantial difference (FIG. 5C). The OxPhos and ETC/RC capacities are measured by the ADP-stimulated and the protonophore FCCP-stimulated respiration, respectively. Further increase in the respiration over ADP-stimulation by FCCP suggests that the OxPhos capacity is lower compared to ETC/RC capacity (FIG. 5A). This may be a common feature of certain cells such as fibroblasts, which may not face an acute ATP shortage that requires a larger spare OxPhos capacity (FIGS. 5A and 6A). However, in other cells (e.g., β-cells) that primarily rely on the mitochondrial OxPhos for their bioenergetic needs, both the OxPhos and ETC/RC capacities must be equal. This point is underscored by a similar level of respiratory stimulation by ADP and FCCP in pancreatic β-cells suggesting that their OxPhos and ETC/RC capacities are almost equal (FIG. 6). Taken together these data underscore the usefulness of PFO-based assays for assessing the relative capacities of OxPhos and ETC/RC in a single experiment. This is a very powerful approach as the information gained is physiologically relevant and reproducible. Further, this experimental system also permits the basis of respiration decline in a given cell to be determined following drug treatments that can impair cellular bioenergetics as described herein.

Example 6: Assessment of ETC/RC and Substrate Supply

Figure 7A:
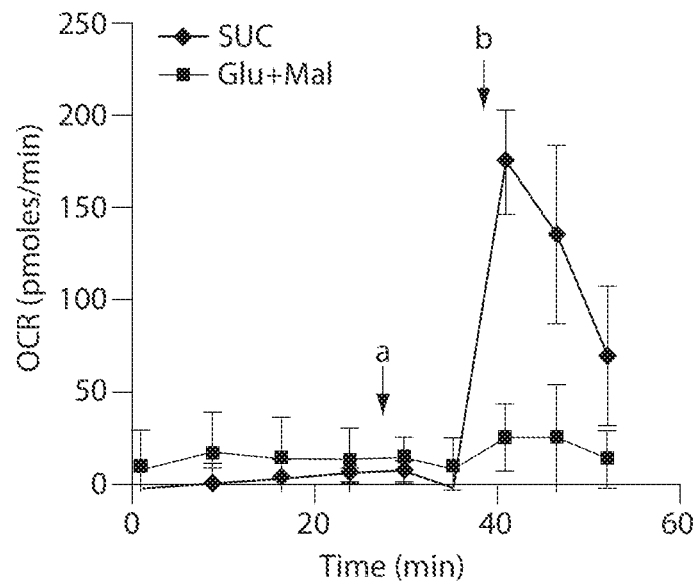
FIGS. 7A-7C show functional assays for Complex I deficiency using the PFO-based method.
Figure 7B:
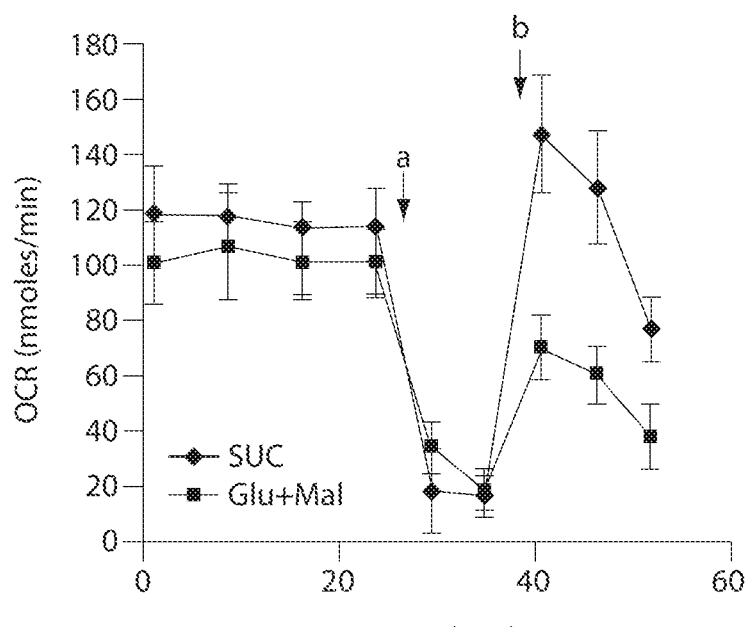
Figure 7C:
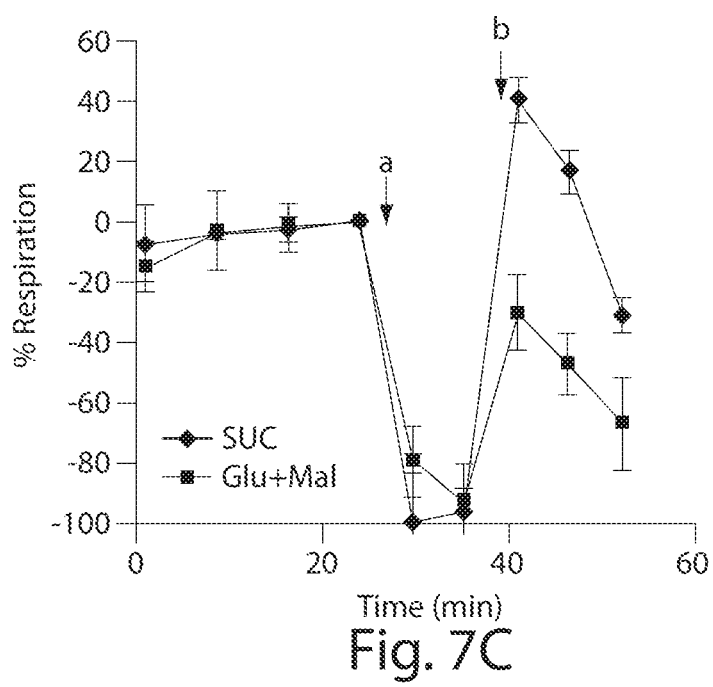

With the reproducibility of PFO-based cell permeabilization, functional screening of mutants with defects in ETC/RC complexes can be performed. The data in FIGS. 7A-7B illustrate an example of Complex I mutants. Complex I mutants lack respiration on substrates that generate NADH (e.g., glutamate+malate), while they show respiration comparable to control cells on succinate that generates FADH2. As described herein, the NADH & FADH2 feed electrons to Complexes I & II respectively. The activities of other complexes also can be assayed using specific substrates and inhibitors (see description of Complex III & IV assays provided herein).

Figure 8:
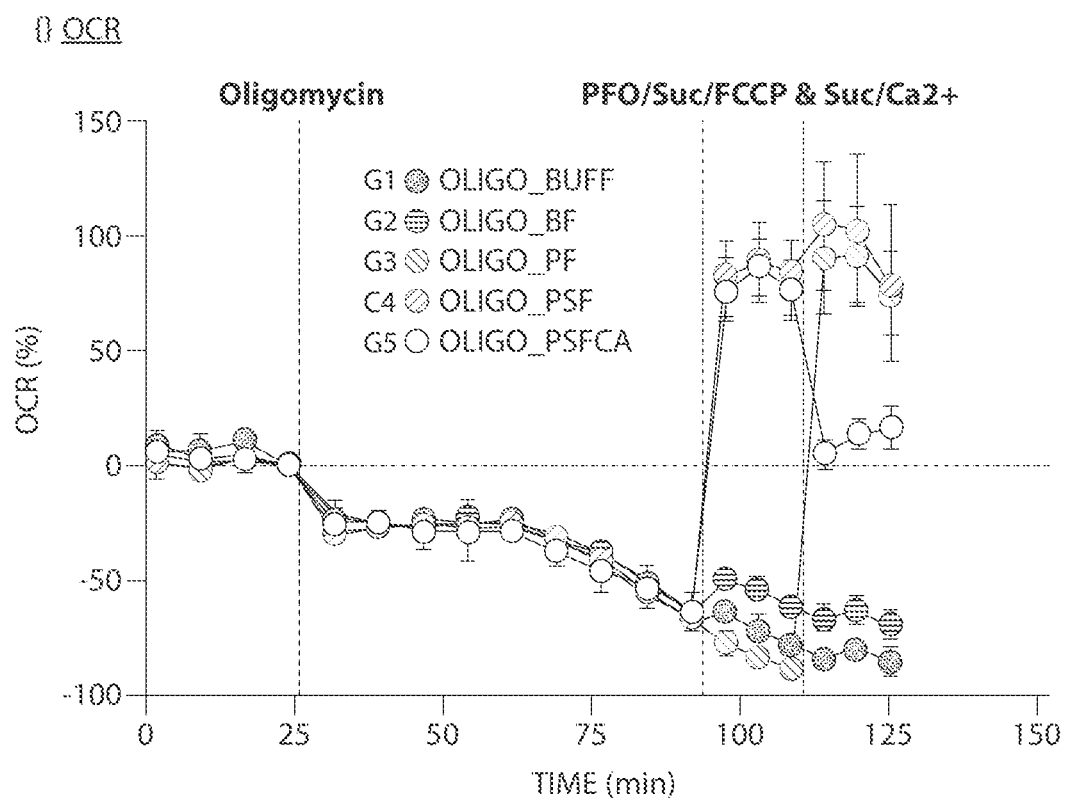
FIG. 8 illustrates limitations in substrate supply to β-cell ETC/RC following oligomycin treatment, and sensitivity to Ca2+-mediated mitochondrial permeability transition. All groups were treated with oligomycin (2 µg/ml) and then after >60 min cells were succinate and/or FCCP with or without nPFO. Groups are as followings. "Oligo_Buffer" indicates oligomycin treated only; "Oligo_SF" indicates oligomycin+succinate+FCCP only; "Oligo_PF" indicates oligomycin+nPFO+FCCP followed by succinate addition later, "Oligo_PSF" indicates oligomycin+nPFO+succinate+FCCP; "Oligo_PSFCa" indicates oligomycin and 1.3 mM CaCl$_2$ added after nPFO+succinate+FCCP additions.

Apart from the determinations of the functional impairments in ETC/RC, the PFO-based assays can be tailored to determine the limitations of substrate supply to the ETC/RC, which can cause respiratory decline under certain conditions. To address this issue, the respiratory decline caused by oligomycin in β cells was evaluated. Data in FIG. 8 show that this oligomycin-induced respiratory decline in β cells is due to limitations in substrate supply. Respiration could be restored only in the PFO-permeabilized cells in the presence of both succinate and FCCP. Further, the addition of $Ca^{2+}$ dropped the respiration significantly, which is believed to be due at least in part to the opening of the permeability transition pore.

In summary, the data presented demonstrate the feasibility of the PFO-based functional assays of mitochondrial function. These assays can be performed using any suitable technique. In some embodiments, microplate-based respirometry using the XF analyzer from Seahorse Biosciences can be used. The PFO can be used to permeabilize cells in a range of settings to study the mitochondrial metabolism apart from the XF analyzer based studies.

Example 7: Evaluation of Mitochondrial NADH Metabolism in Pancreatic β-Cells FIGS. 10-14 show results from assays described below involving PFO-based permeabilization. In association with the glucokinase, the role of mitochondrial metabolism is widely recognized in glucose sensing. It is thought that the low affinity glucokinase, which is insensitive to feedback inhibition by ATP, increases the flux through glycolysis and enhances pyruvate production. Pyruvate is suggested to be metabolized by TCA cycle to generate electron donors (NADH & FADH2 for respiratory Complexes I & II, respectively) for ATP production, and provide additional signals for sustained release of insulin. Although imaging based studies have suggested that pyruvate metabolism within mitochondria may not be efficient in generating NADH, its implication on mitochondrial function does not appear to have been explored in detail elsewhere.

Using an in situ respirometry assay with permeabilized INS1E and dispersed islet cells, the ability of β-cells to generate NADH on different substrates was explored. The data show that β-cell mitochondria do not display a detectable level of respiration on NADH-generating substrates, while the mitochondria from lung fibroblasts, astrocytes and neurons display robust respirations under the same experimental conditions. Furthermore, the respiration rates on succinate and α-glycerophosphate, the substrates for Complexes II & III respectively, were very robust. These data indicate a unique regulation of NADH metabolism within β-cell mitochondria, which may be associated with limited NADH production and/or consumption by enzymes other than Complex I. NADH levels were lower compared to that found in fibroblast and astrocyte mitochondria. It is proposed that β-cells regulate NADH output per glucose within mitochondria by negatively regulating key steps to favor the reliance on redox shuttles, and help export of malate and citrate to cytosol for tight coupling of glucose metabolism with insulin secretion.

β-cell bioenergetics is dependent on oxidative phosphorylation. It plays a role in insulin secretion by β-cells. The reliance of insulin secretion on cytosolic NADH oxidation via redox shuttles suggests that the Respiratory Chain function in β-cells is primarily dependent on the cytosolic electron donors. Therefore, whether NADH production within β-cell mitochondria is lower compared with other cells (such as astrocytes and fibroblasts) that are not glucose sensitive has been tested. The differences in Complex I-dependent respiration using various NADH generating substrates were monitored. Furthermore, in order to probe the role of oxidative phosphorylation in pyruvate cycling, the respiratory decline in the presence of oligomycin that blocks ATP synthase (Complex V) activity was monitored.

The results of PFO-based assays in Example 7 indicate that permeabilized β-cells do not show Complex-I dependent respiration due to limited NADH production within mitochondria. In intact β-cells respiration could be supported solely by the redox shuttles. The respiratory and oxidative phosphorylation capacities in β-cells are comparable. In these experiments, oxidative phosphorylation in β-cells was important to maintain respiratory activity irrespective of the substrate being used. The respiratory decline in the presence of oligomycin observed in this example is associated with substrate limitations, which occurs due to block in pyruvate cycling within β-cells.

Example 8: Determination of Spare Oxidative Phosphorylation Capacity and Cell-Specific Features of Mitochondrial Metabolism Using Perfringolysin O and Variants Thereof Overview:

In this Example, the effectiveness of using detergents for cell permeabilization in mitochondrial function assays was compared with cholesterol-dependent cytolysin (CDC) perfringolysin O (PFO) and certain variants thereof. CDCs are secreted as water soluble monomers of 50-70 kDa that form large ring- and are shaped homooligomeric pores (35-50 monomers/oligomer) in cholesterol containing membranes. The formed pores are approximately 250 Å in diameter and allow the passage of large molecules (e.g. antibodies, β-amylase, and thyroglobulin). Results described below indicate that mitochondrial integrity is better preserved when cells are permeabilized with PFO compared to detergents.

In addition, PFO-based methods have been develop that permit determination of spare OxPhos capacity and other bioenergetic features in small samples using microplate-based respirometry. Using these methods it was found that in bioenergetically demanding cells, such as β cells, the spare OxPhos capacity is comparable to the spare respiratory capacity, while in other cells such as fibroblasts, it is lower than the respiratory capacity. These data indicate that in the presence of adequate respiratory substrate such as succinate and ADP, the level of inorganic phosphate (Pi) has a significant effect on the OxPhos capacity.

Material and Methods:

Reagents:

Rotenone was from Calbiochem. Other reagents were from Sigma unless otherwise stated.

Preparation of the Functional PFO:

Native (nPFO), the Cysteine-free rPFO (nPFO containing the C459A mutation), and the engineered disulphide-bond containing mutant dbPFO (rPFO containing the double T319C-V334C mutation) were purified using art known methods. These derivatives contain the polyhistidine tag from the pRSET-B vector (Invitrogen). No significant functional or structural differences were detected among PFO derivatives bearing or lacking the polyhistidine tag.

Both nPFO and rPFO are cytolytically active, but rPFO utilizes higher cholesterol concentrations when tested using model membranes. In contrast, dbPFO binds to membranes but does not form pores because one of the transmembrane β-hairpins is covalently linked to domain 2 via a disulphide bond. Reduction of the disulphide bond by the addition of (2S,3S)-1,4-bis(sulfanyl)butane-2,3-diol (DTT) releases the locked transmembrane β-hairpin triggering the insertion of a large transmembrane barrel.

Following purification the Cysteine-free rPFO and the dbPFO were stored in buffer A [50 mM HEPES pH 7.5, 100 mM NaCl, and 10% (v/v) glycerol] while the nPFO was stored in buffer A supplemented with 5 mM DTT to retain its cytolytic activity. Proteins were kept at −80° C. until used. The protein concentration was calculated using a molar absorptivity ($\epsilon^{208}$) of 74260 cm$^{-1}$M$^{-1}$.

Cells and Culture Conditions:

Rat insulinoma INS1E cells were grown in RPMI1640 medium (Mediatech Inc, Manassas, Va.) which was supplemented with 11.1 mM of glucose, 10% fetal bovine serum (FBS), 1 mM HEPES (Invitrogen), and 50 μM of β-mercaptoethanol (2-Sulfanylethan-1-ol). Starvation medium contained 4 mM glucose instead of 11.1 mM glucose in the presence of 1 mM Na-pyruvate. Other cells such as Chinese hamster lung fibroblasts (V79-G3, CCL16-B2, CCL16-B2-MWFE), human embryonic kidney (HEK293) cells, and mouse C2C12 myoblasts were grown in Dulbecco's Modified Eagle's Medium (DMEM, Invitrogen, Grand Island, N.Y.) supplemented with 10% FBS (Invitrogen), 1% non-essential amino acids (Mediatech, Inc, Manassas. Va.), and 1% antibiotic mix (PenStrep, Invitrogen) at 37° C. in a humidified atmosphere of 5% CO2/95% air. The human neuroblastoma SHSY5Y cells were cultured in DMEM/F12 media with 10% FBS and 1% antibiotics mix. Cells were harvested after washing once with Ca2+ and Mg2+-free phosphate buffered saline (PBS: pH 7.4) using 0.05% trypsin-EDTA (Invitrogen).

Isolation of Rat Primary Pancreatic β-Cells:

Pancreatic islets were isolated from Wistar rats using methods known in the art. Collagenase P enzyme solution (1.2-1.4 mg/ml, Roche Diagnostics Corporation, Indianapolis, Ind.) was injected into the distal end of the donor pancreas. After digestion, islets were gradient purified and then handpicked and cultured in RPMI-1640 medium supplemented with 10% heat-inactivated FBS and 1% Pen-Strep (Mediatech, Manassas, Va.) in a 5% CO2 incubator. Single cells from islets were prepared using art known methods. After 24-48 hr post culture, islets were collected at 1100 rpm for 5 min at 4° C. followed by washing in PBS twice. Collected islets were treated with 0.05% trypsin supplemented with EDTA (Invitrogen) for 3 min and then triturated gently to separate cells. Trypsin activity was stopped by adding RPMI medium containing serum before triturating. 100,000 cells were seeded per well in polyethyleneimine (PEI)-coated V7 PS XF24 culture plates from Seahorse Bioscience (Billerica, Mass.). Cells were used for experiments 72 hr after seeding unless otherwise noted. In rat islets, β-cells are the predominant cell types (~80%). Unless otherwise indicated dispersed rat islet cells are referred to herein as primary β-cells.

Figure 23A:
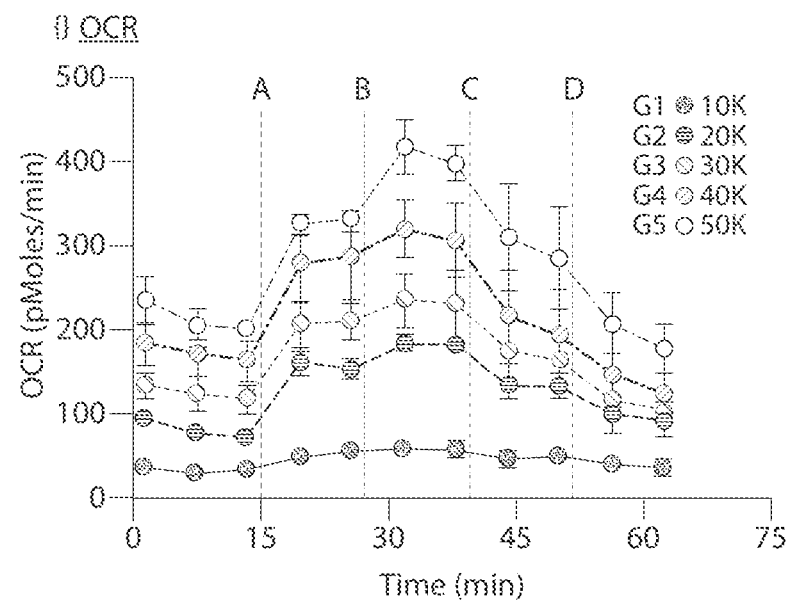
FIGS. 23A-23B show results of FCCP titrations using intact cells. HEK293 cells were seeded at indicated cells densities, and then respiration assay was performed as described in Example 8 using LKB buffer with 1.3 mM CaCl2 and 15 mM glucose without added EGTA.
Figure 23B:
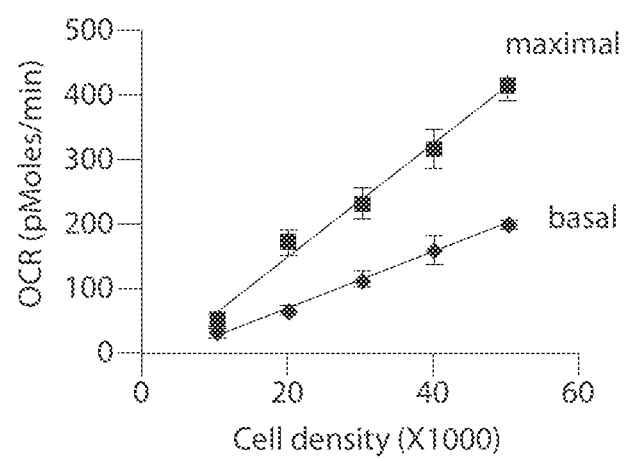

Respirometry and Cell Permeabilization:

Cells grown ~80% confluence in V7 tissue culture plates were used for in situ microplate-based respirometry using the XF24 Flux Analyzer (Seahorse Biosciences). All assays were performed with V7 PS plates unless otherwise specified. Cells were seeded at the following densities/well: 10-20,000 (lung fibroblasts-V79-G3, B2-MWFE; HT1080); 25,000 (primary astrocytes); 30,000 (HEK293); 50,000/well (INS1E): and 100,000 (primary β cells). Cells were grown for 24-72 hr after seeding, unless otherwise indicated, washed twice with 500 μl of the indicated respiration buffer (see Table 6) and then incubated in a non-CO$_2$ incubator at 37° C. for ~30-60 min. XF24 cartridges pre-hydrated for 24 hr were calibrated according to the manufacturer's instructions after loading injection ports with the indicated compounds. After calibration of the sensor cartridge per manufacturer's instructions, the V7 culture plate with cells was loaded into the XF24 analyzer. Respiratory activity of cells was measured using cycles of mixing, waiting and measuring at 0.5-2, 1.5-2 and 3-5 min. respectively, depending upon the cell type used. After 3-4 respiration rate measurements, cells were permeabilized with the indicated reagent (e.g., digitonin, saponin, PFO, rPFO, or dbPFO). The indicated respiratory substrates (e.g. succinate, or glutamate+malate) were either present in the respiration buffer before permeabilization of cells or added with the permeabilizing agent or afterward. Optimum concentrations of ADP (1-2 mM), and carbonylcyanide p-trifluoromethoxy phenylhydrazone (FCCP) were determined by titration assays for different types of cells used. FIGS. 23A-23B show a typical FCCP titration assay using HEK293 cells. Oligomycin was not used in FCCP titration assays. Same FCCP concentrations that gave maximal respiration in intact cells were applied to permeabilized cells. Successive (1st, 2nd, 3rd) additions of compounds were made using injection ports a, b, & c respectively. All respiratory substrates (succinate, malate, glutamate, pyruvate etc.) were used at 10 mM concentration unless otherwise noted. Cyt C was used at 10 μM concentration. Actual or normalized (basal respiration set to 100% or 0%) oxygen consumption rates (ORC) are presented as measures of respiration. Increase in the respiratory activity over basal respiration rate by ADP and FCCP were taken as spare (reserve) OxPhos capacity and spare respiratory capacity.

NAD(P)H Assays:

Mitochondria from INS1E and B2-MWFE cells were isolated using art known methods. Mitochondrial content was measured using a microplate-based BCA protein assay kit (Thermo Fisher). 20 g of mitochondria in 250 μl Ca2+ free LKB (without glucose) were incubated with glutamate+ malate (10 mM each) in the presence of 2 μM rotenone for 115 min at 37° C. FLUOstar Omega fluorimeter (BMG Labtech) was used to measure the relative levels of NAD (P)H at 355 nm excitation and 460 nm emission wavelengths. An NADH standard curve was used to determine concentrations of NAD(P)H.

Results:

Mitochondrial Integrity is Compromised in Detergent-Permeabilized Cells:

A rat insulinoma cell line, INS1E, was used to assess permeation conditions for mitochondrial function assays. INS1E cells are an experimental model for rat pancreatic β cells. Digitonin has been used for selective plasma membrane permeabilization to assess mitochondria function. A digitonin-based assay was evaluated to determine whether it would be suitable for a microplate based respirometry that employs a limited number of cells (e.g., 5000 to 100,000 cells).

Figure 16A:
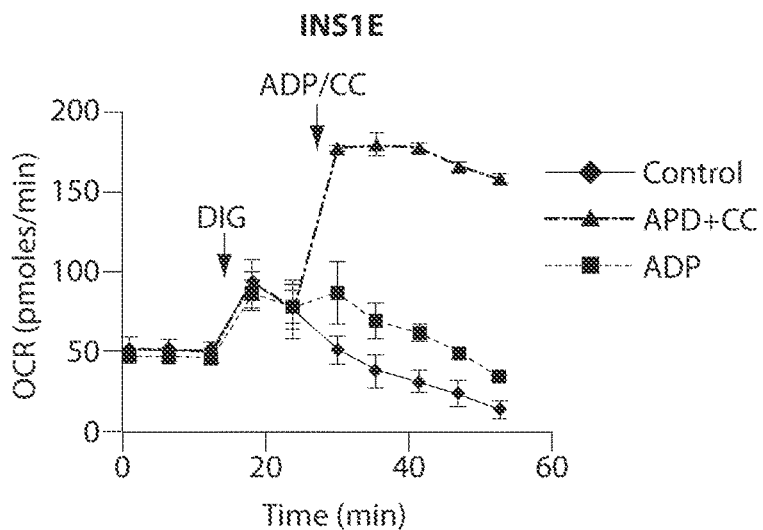
FIGS. 16A-16F show results of an assay of mitochondrial function with digitonin-permeabilized cells. β cells were grown as described in Example 8. Ca2+-free LKB buffer containing 10 mM succinate was used in the presence of 2 mM (FIGS. 16A-16C) or 15 mM glucose (FIGS. 16D-16F).

First, an appropriate digitonin concentration was determined for maximal ADP-stimulated respiration using succinate as the substrate. Maximal and sustained respiration was observed with 0.01% digitonin in the presence of 10 μM Cyt C (FIG. 16A). In the absence of Cyt C, maximal respiration was not achieved even at lower digitonin concentrations. These data indicate that digitonin impairs outer mitochondrial membrane integrity resulting in Cyt C release. With a different batch of digitonin obtained from the same source decreasing respiration rates were observed with increasing concentrations within 0.0025-0.01% range. The type of respiration buffer used had significant effect on mitochondrial function when cells were permeabilized with digitonin (FIG. 29). Thus even with careful titrations, a digitonin concentration that would work reproducibly in different assay conditions for a given cell type was not identified.

To test the coupling of respiratory activity with ATP synthesis, the extent to which ADP-stimulated respiration is sensitive to oligomycin was evaluated. Oligomycin is an inhibitor of the ATP synthase (Complex V) that uses Δp to synthesize ATP from ADP and Pi (see FIG. 15). The majority of the ADP stimulated respiration (~75%) was oligomycin sensitive when oligomycin was added along with ADP. The remaining respiration is expected to be supported by the H+ leak across inner mitochondrial membrane.

Figure 16B:
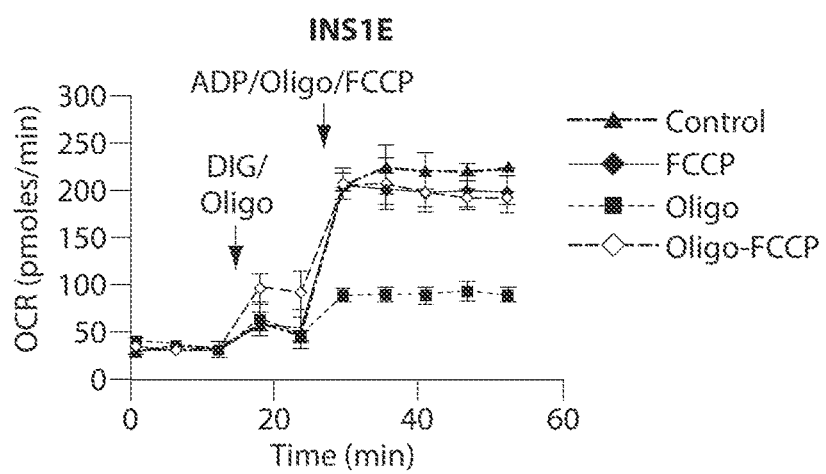
Figure 16C:
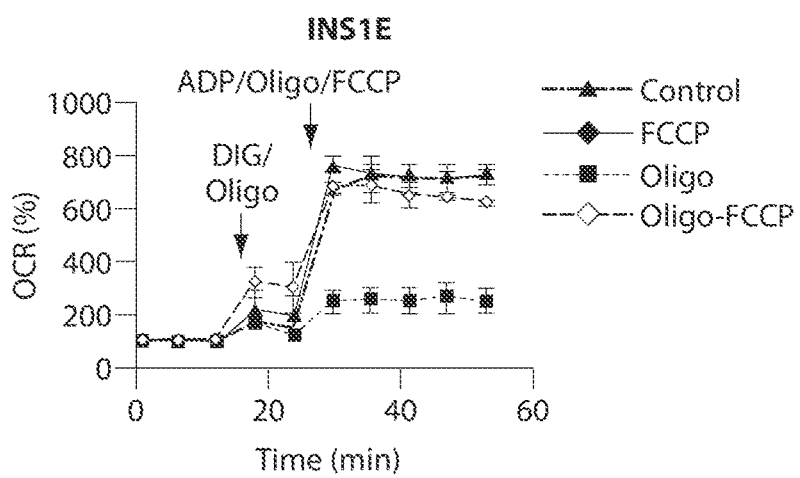

To determine the respiratory capacity, FCCP was used. FCCP, which is a protonophore, induces maximal respiration by dissipating the H+ gradient across the mitochondrial inner membrane. Thus, a suitable FCCP concentration as determined by titration was used to determine the respiratory capacity (maximal respiration) of INS1E cells. Both ADP and FCCP gave comparable respiratory stimulations indicating that spare OxPhos capacity and respiratory capacity, respectively, were comparable in INS1E cells (FIG. 16B, 16C). Significant differences were not observed between the spare OxPhos and respiratory capacities using succinate as the respiratory substrate. Furthermore, FCCP-stimulated respiration in the presence of oligomycin was not significantly different from that observed without oligomycin, which indicates that respiratory capacity was primarily determined by the functional capacity of ETC/RC.

Figure 16D:
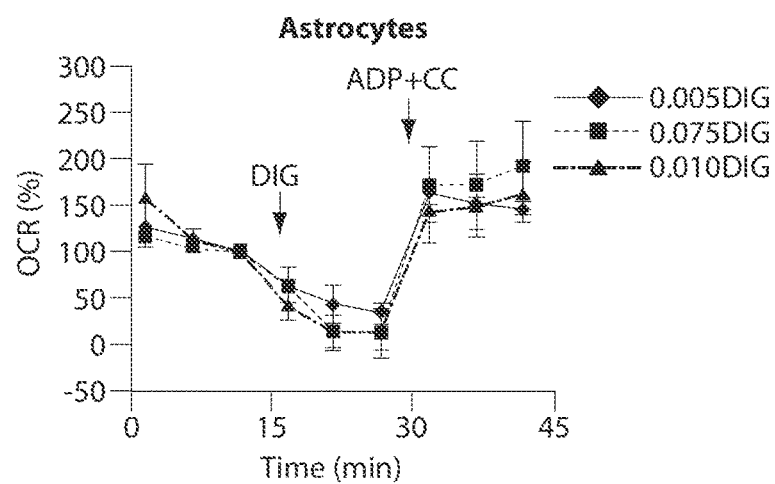
Figure 16E:
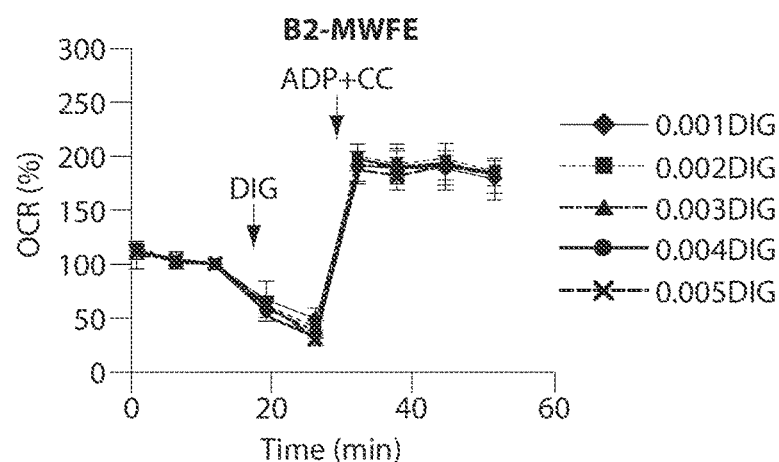
Figure 16F:
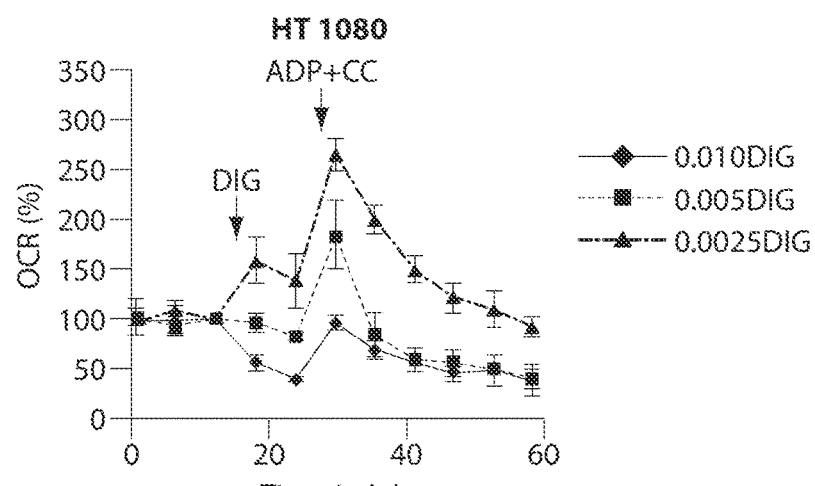

To assess the extent to which the same experimental conditions can be employed to assay mitochondrial function in other cells, ADP-stimulated, succinate-supported respiration was evaluated in various cell types, including primary rat astrocytes, Chinese hamster fibroblasts and human cells. Similar conditions were applicable to rat astrocytes (FIG. 16D), and digitonin titrations were utilized for hamster (B2-MWFE) and humans (HT1080) cells (FIG. 16E, F).

Figure 24A:
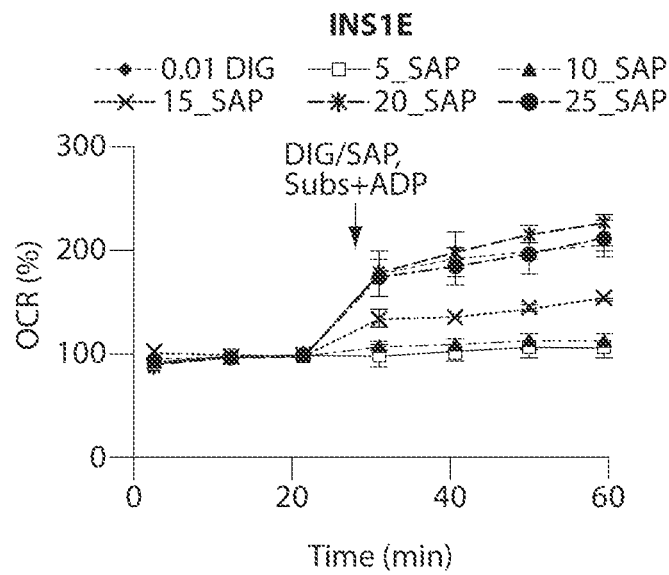
FIGS. 24A-24B shows the relative performance of certain cell permeabilizing agents compared to digitonin. INS1E cells were grown and assays were performed as described in Example 8. β cells were permeabilized with indicated agents and respiration was monitored in the presence of succinate (10 mM), ADP (1 mM) and Cyt c (10 μM).
Figure 24B:
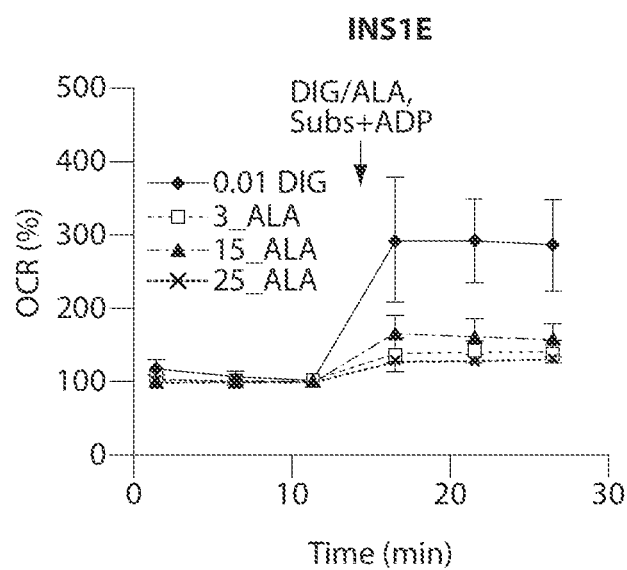
Figure 25A:
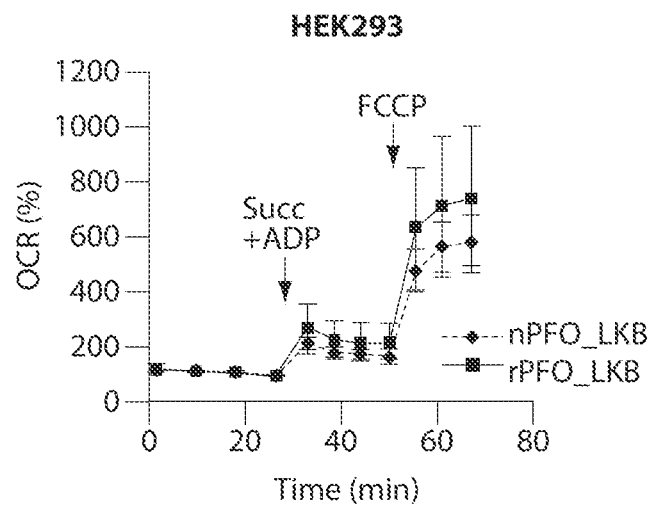
FIGS. 25A-25F shows comparative performances of different PFO variants and the effects of DTT on respiration. Respiratory rates in nPFO- and rPFO-permeabilized HEK293 cells were determined in Ca2+-free LKB (FIG. 25A) and HKB (FIG. 25B) buffers. The rPFO data from panels
Figure 25B:
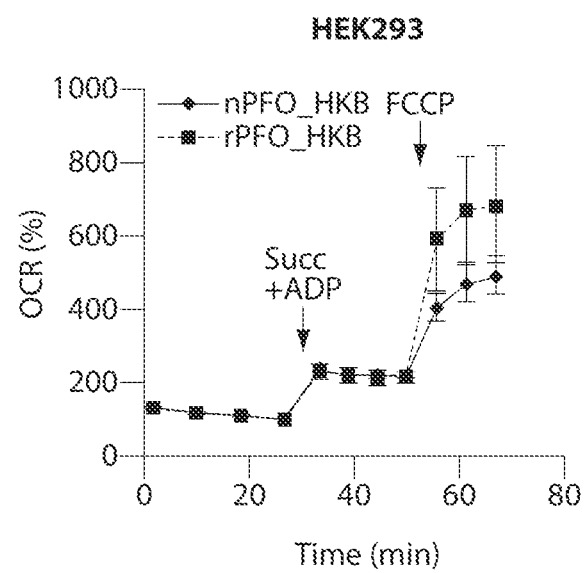
Figure 25C:
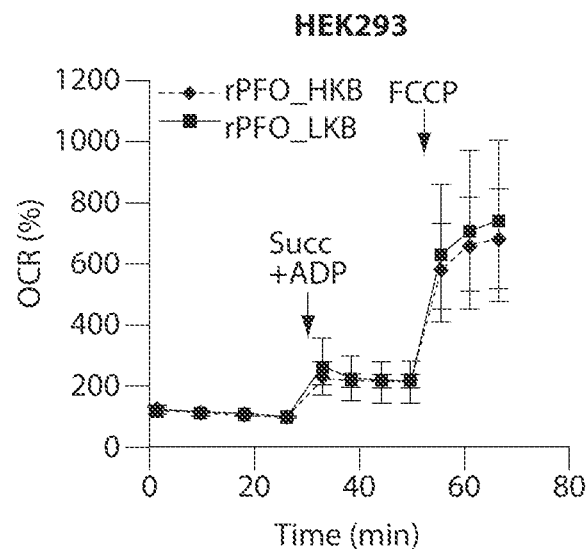
Figure 25D:
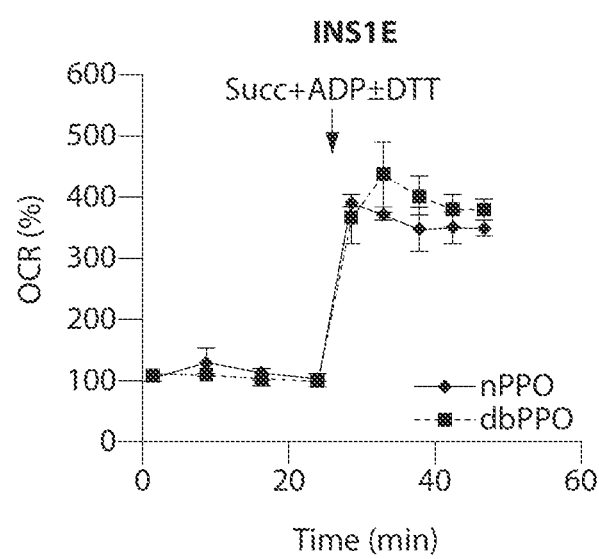
Figure 25E:
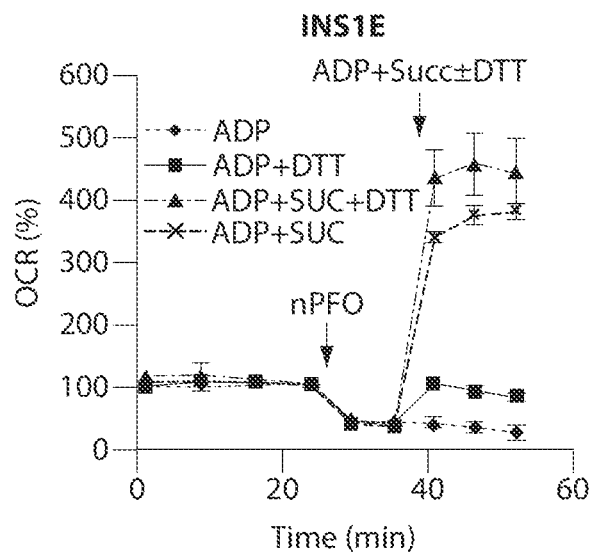
Figure 25F:
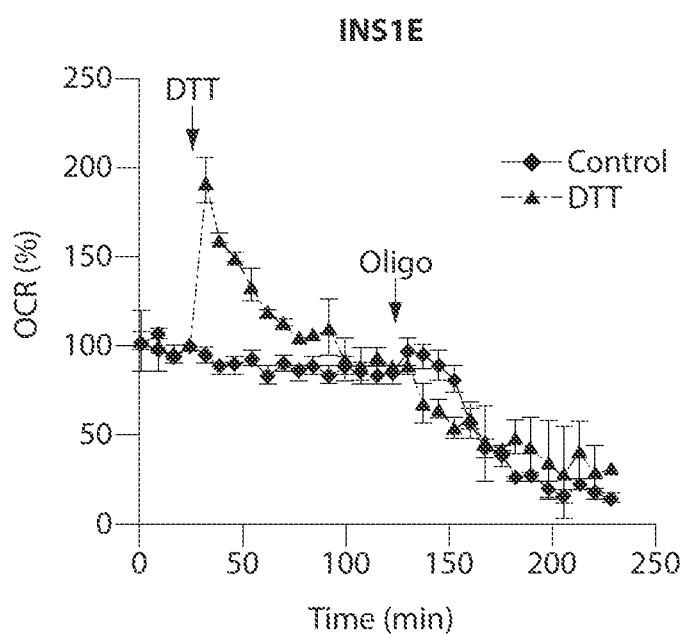
Figures 26A, 26B:
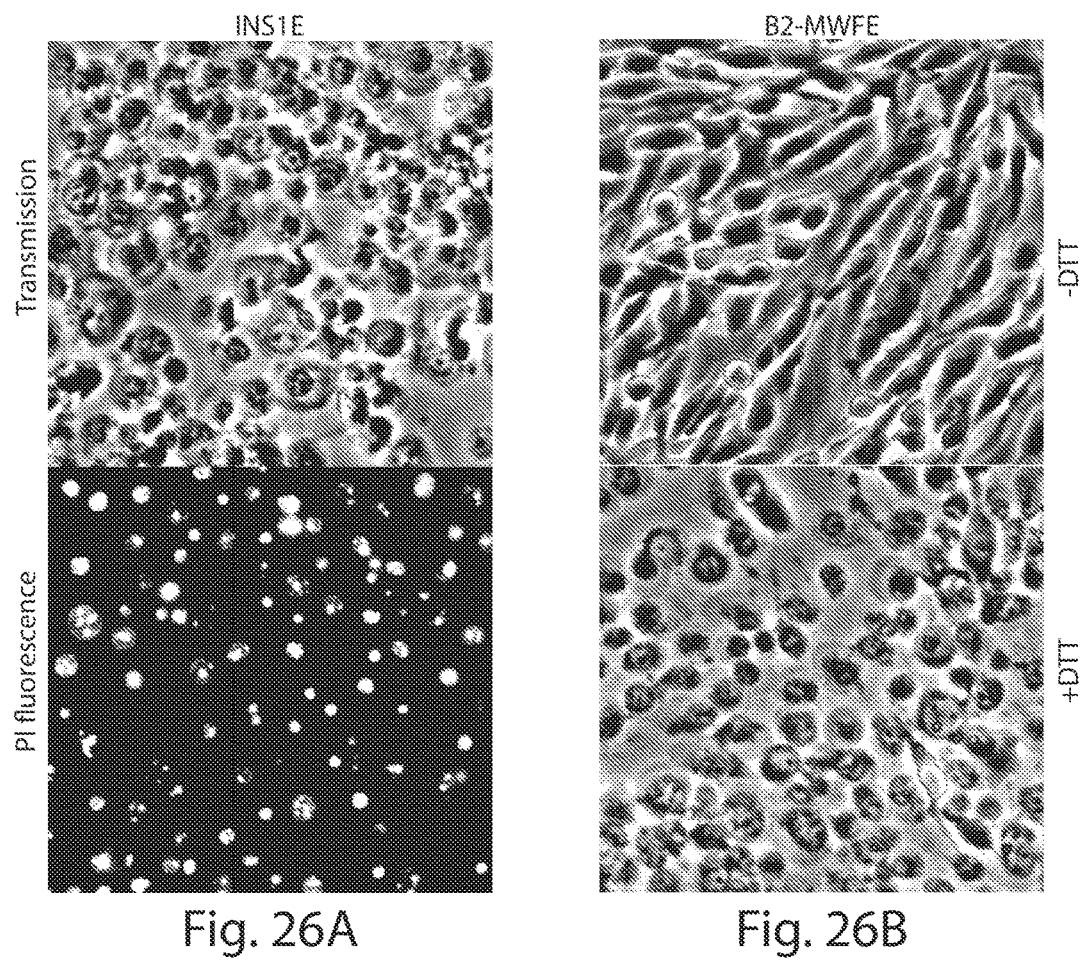
FIG. 26A shows rPFO-permeabilized INS1E cells. Cells permeabilized with 1 nM rPFO were observed under microscope at the end of experiments in V7 culture plates. Propidium iodide (PI) staining was used to confirm complete permeabilization (bottom), which was evident from cytoplasmic swelling (top).
FIG. 26B shows dbPFO-mediated permeabilization of B2-MWFE cells. 100 nM DTT was used to induce the pore formation in 1 nM dbPFO-treated cells.

The relative performances of other agents such as saponin (another detergent), and alamethicin (a pore forming peptide) were compared to digitonin. Both saponin and alamethicin have been used in assays of mitochondrial function in different experimental settings. Results with saponin, but not alamethicin, were comparable to digitonin in INS1E cells (FIG. 24A, 24B). Compared to digitonin results with saponin were less reproducible.

Mitochondrial Integrity Remains Intact in PFO-Permeabilized Cells:

Cholesterol-dependent cytolysins (CDCs) were used to preserve mitochondrial integrity following cell permeabilization. CDCs (e.g., perfringolysin O (PFO)) bind to membranes containing relatively high amounts of cholesterol. Pores formed by the insertion of transmembrane β-barrels of a CDC were found to be better controlled and more homogenous than those obtained with detergents. Intracellular organelles therefore remain structurally and functionally intact in the presence CDCs.

Figure 17A:
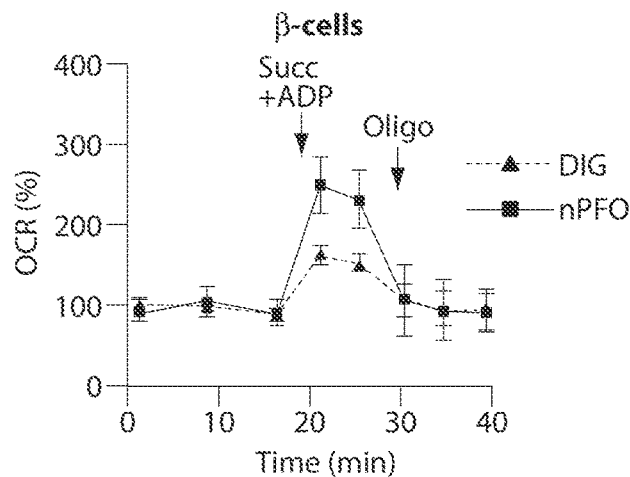
FIGS. 17A-17F show results of an assay of mitochondrial function with nPFO-permeabilized cells. Cells were prepared as described in Example 8 and the assays were performed in Ca2+-free LKB buffer containing 2 mM glucose (FIGS. 17A-17D) or 15 mM glucose (FIGS. 17E-17F).
Figure 17B:
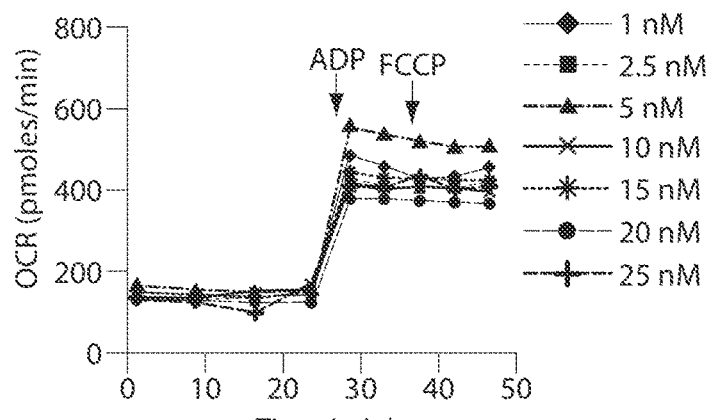
Figure 17C:
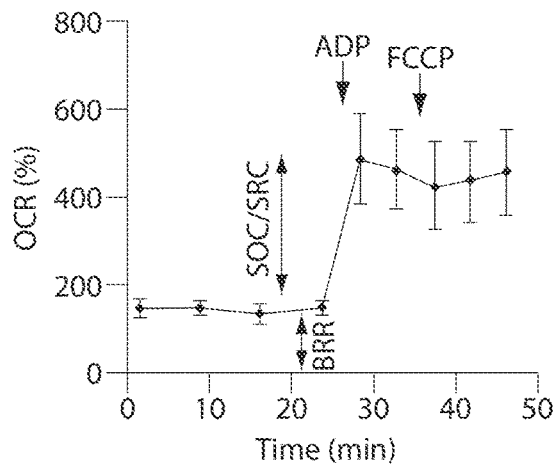
Figure 17D:
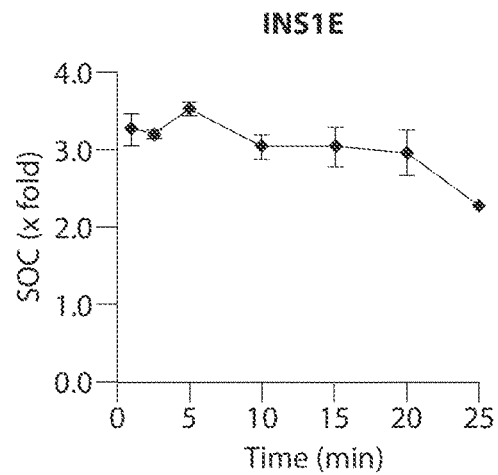

Several perfringolysin O (PFO) derivatives were developed for permeabilization assays. It was found that the respiratory response was more robust in P cells permeabilized with nPFO compared with digitonin (FIG. 17A). Such an improvement in mitochondrial function with nPFO was also observed in Chinese hamster lung fibroblasts as well (V79-G3). nPFO dose-response analyses were performed to determine a minimal concentration required for maximal mitochondrial function. Spare OxPhos and respiratory capacities of INS1E and V79-G3 cells were measured at different doses. It was found that, in some embodiments, 1 nM PFO was adequate for maximal mitochondrial performance (FIGS. 17B-D). A further increase in respiration was not observed by FCCP addition beyond ADP-stimulation at all nPFO doses tested (FIG. 17B).

Figure 17E:
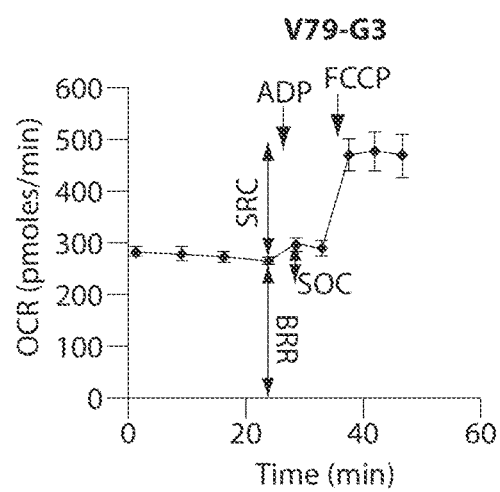
Figure 17F:
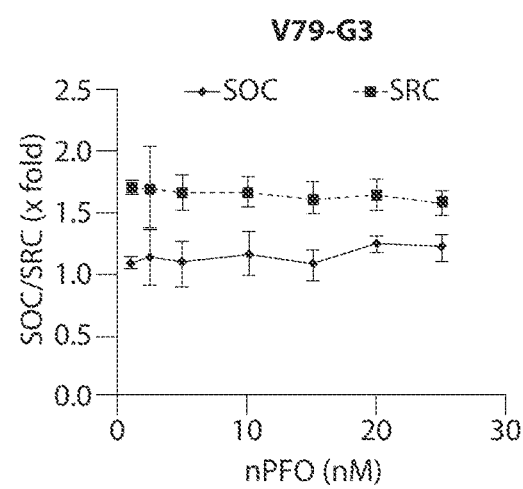

Using an nPFO-based assay it was found that OxPhos capacity of INS1E cells was comparable to respiratory capacity (FIGS. 16B, C and FIGS. 17B, C). Unlike in INS1E cells, the spare OxPhos capacity in V79-G3 cells was lower compared to respiratory capacity (FIGS. 17E, F). There was no change in spare OxPhos and respiratory capacities against a wide range of nPFO concentration in V79-G3 cells. Even for Chinese hamster V79-G3 cells as little as 1 nM nPFO was sufficient for maximal mitochondrial performance (FIG. 17F).

Figure 18A:
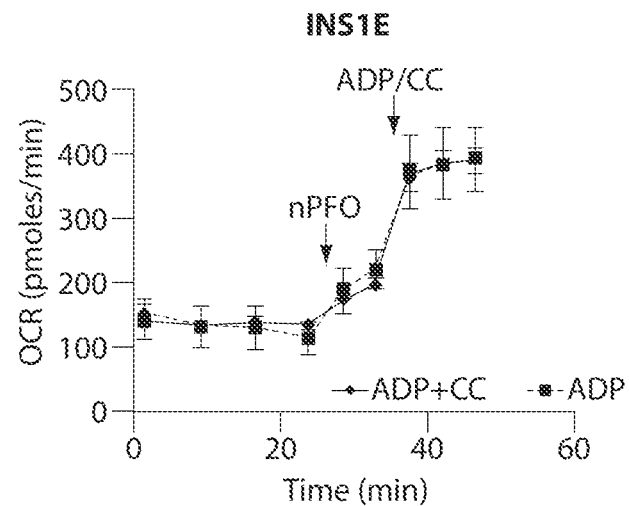
FIGS. 18A-18H show an assessment of mitochondrial integrity and respiratory coupling in nPFO-permeabilized cells. After growing cells as described in Example 8 respiration was measured in Ca2+-free LKB buffer containing 10 mM succinate with 2 mM glucose (FIGS. 18A-18C) or 15 mM glucose (FIGS. 18D-18H) β cells were first permeabilized with at least 1 nM nPFO, and then changes in respiration rates were measured following addition of the indicated compounds.
Figure 18B:
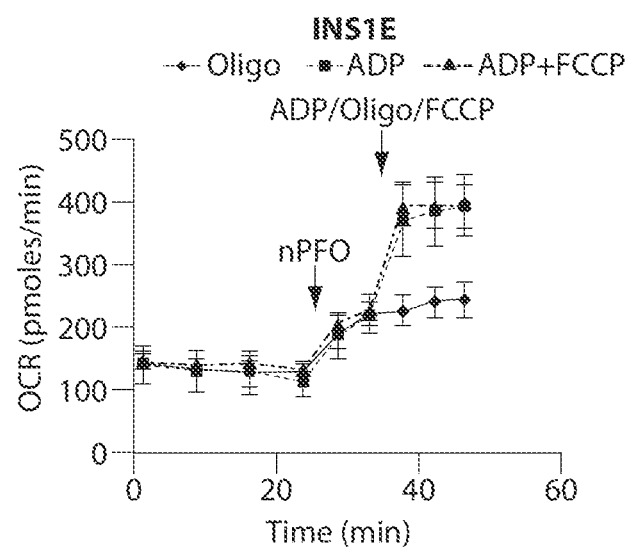
Figure 18C:
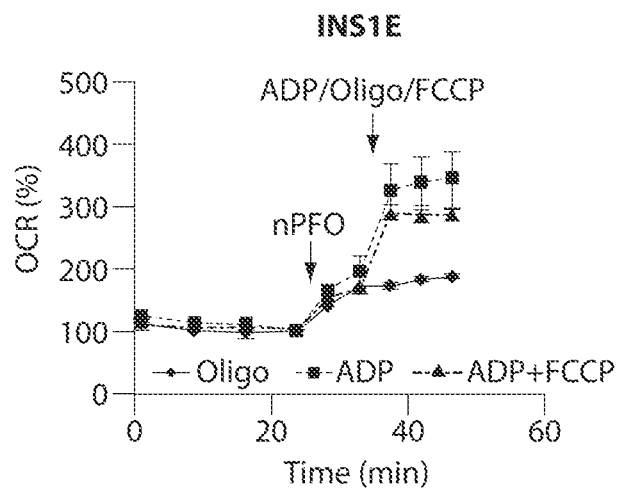
Figure 18D:
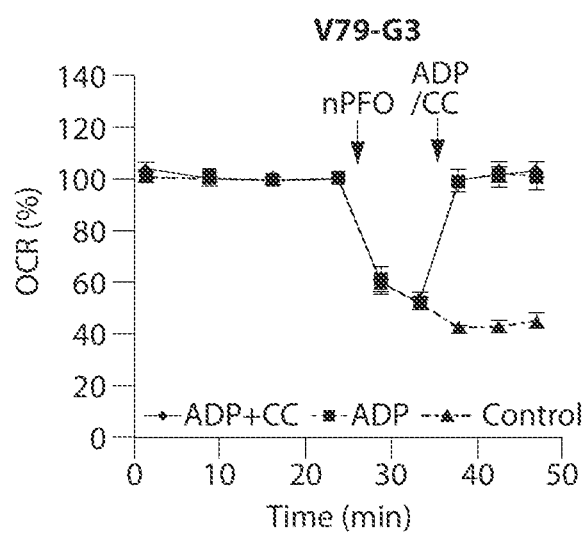
Figure 18E:
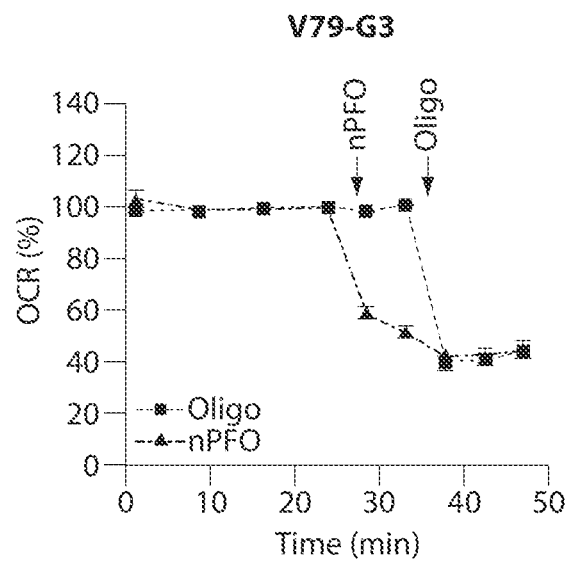

In contrast to digitonin based-assays, exogenous Cyt C was not required when mitochondrial function was assayed in nPFO-permeabilized cells. There were no differences observed in mitochondrial performance in the absence or presence of added Cyt C across different cell types (FIGS. 18A, D, G, H). In β cells respiratory activity is generally proportional to external glucose concentration, while in other cell types it is not. When glucose is not limiting, β cell permeabilization also results in respiratory decline (FIG. 19F). In the presence of succinate alone, respiration declined to a steady-state level in permeabilized V79-G3 cells (FIG. 18D). The remaining respiration was supported by H+ leak as it was comparable to oligomycin insensitive respiration in intact cells (FIG. 18E). Addition of ADP alone restored the respiration close to the basal level (pre-permeabilization state, FIG. 18D). When ADP was added simultaneously with nPFO, there was no respiratory decline, and instead there was ~20% increase in respiration over the basal level (FIGS. 17E, 18F).

Figure 18F:
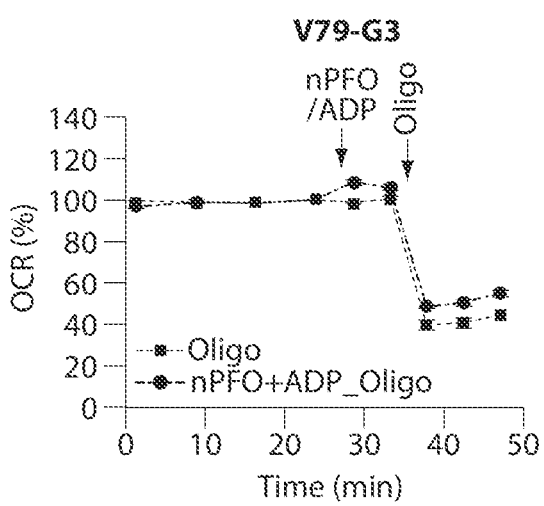
Figure 18G:
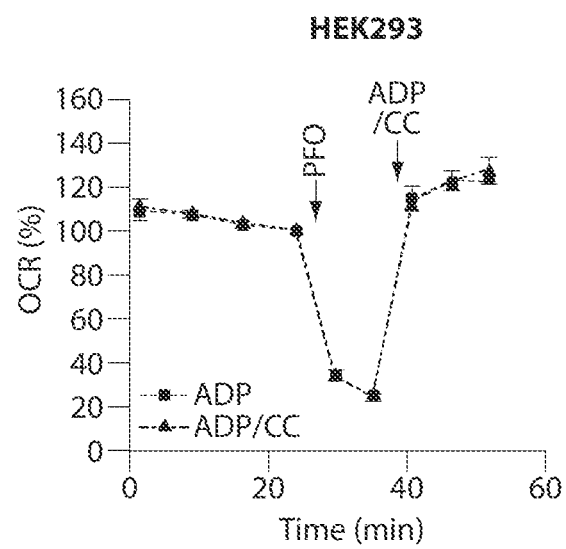
Figure 18H:
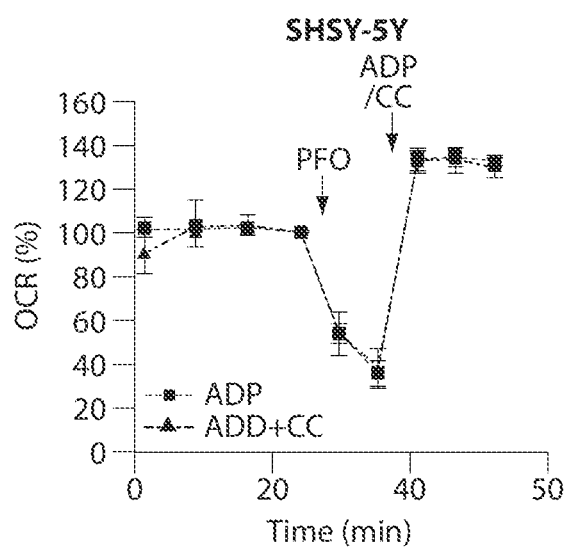

ADP-stimulated respiration was sensitive to oligomycin, indicating respiratory coupling with ATP synthesis (FIG. 18F). ADP alone result in respiratory stimulation indicating that plasma membrane was impermeable to ADP. The respiratory decline in the presence of oligomycin overlapped with that of nPFO-permeabilized cells (FIG. 18E). These data indicate that ETC/RC function was coupled with ATP synthesis in both INS1E and V79-G3 cells and mitochondrial integrity was preserved.

Figure 19A:
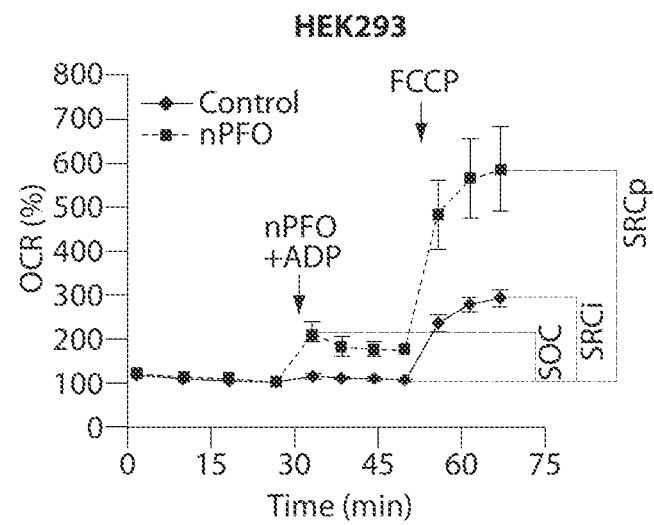
FIGS. 19A-19F show estimations of the spare (reserve) and total capacities of OxPhos and ETC/RC. β cells were grown as described in Example 8 and assays were measured in Ca2+-free LKB (FIGS. 19A, and 19D-19F) or LPBT (FIGS. 19B and 19C) buffers containing 15 mM glucose. 10 mM succinate was added with 1 mM ADP to measure spare OxPhos capacity (SOC). After measuring the ADP-stimulated respiration FCCP was added to measure spare ETC/RC capacity (SRC).

Determination of the Spare OxPhos Capacity Using PFO-Based Assays:

Respiratory stimulation with appropriate amounts of ADP in the presence of saturating substrate concentration at the time of permeabilization permits measurement of spare OxPhos capacity. Data in FIG. 19A show a typical experiment for determining spare OxPhos and respiratory capacities. Human HEK293 cells were used for these assays. β cells were incubated in Ca2+-free respiration buffer containing 15 mM glucose, and then succinate and ADP were added with nPFO simultaneously. The ADP-stimulated respiration over the basal respiration gives the estimate of spare OxPhos capacity. To determine whether spare OxPhos capacity (SOC) matched the spare respiratory capacity (SRC), FCCP was added to the same cells. By monitoring the ADP- and FCCP-stimulated respiration within the same cells, the fraction of spare respiratory capacity supporting ATP synthesis (SOC/SRC) was determined. Comparison of the spare respiratory capacity of intact and PFO permeabilized cells (SRCi vs. SRCp) indicated that SRC could be underestimated by ~60% in intact cells using glucose as the respiratory substrate in some cases (FIG. 19A).

Figure 19B:
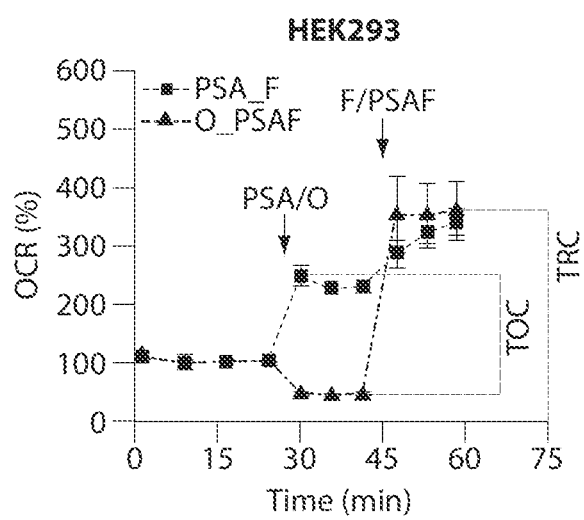
Figure 19C:
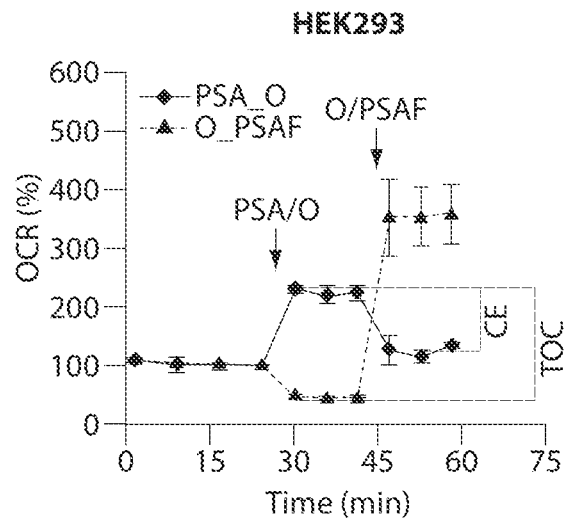

FIG. 19B show data from which an estimation of total OxPhos capacity may be made. It shows that by adding spare OxPhos capacity (SOC) to the oligomycin-sensitive respiration (OSR) total OxPhos capacity (TOC) of a given cell type can be determined under a given experimental condition. Since the oligomycin effect is relatively instantaneous, the sum of spare OxPhos capacity (SOC) and oligomycin-sensitive respiration (OSR) in intact cells provides an accurate estimate of total OxPhos capacity (TOC=SOC+OSR). Further coupling efficiency (CE) can be determined by monitoring oligomycin-sensitivity of the ADP-stimulated respiration (FIG. 19C). The presence of oligomycin did not appear to affect spare and total respiratory capacities (FIG. 19B).

Figure 19D:
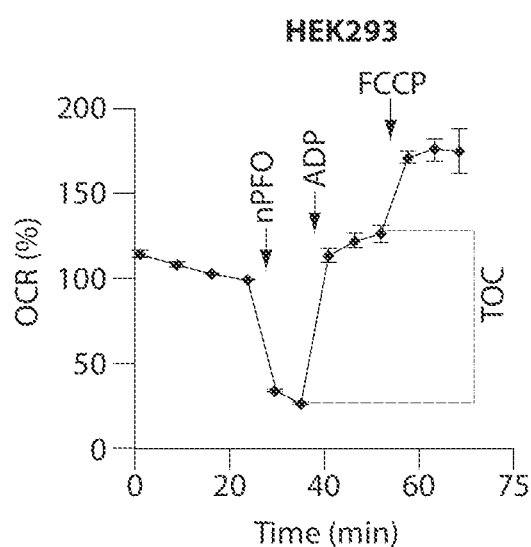
Figure 19E:
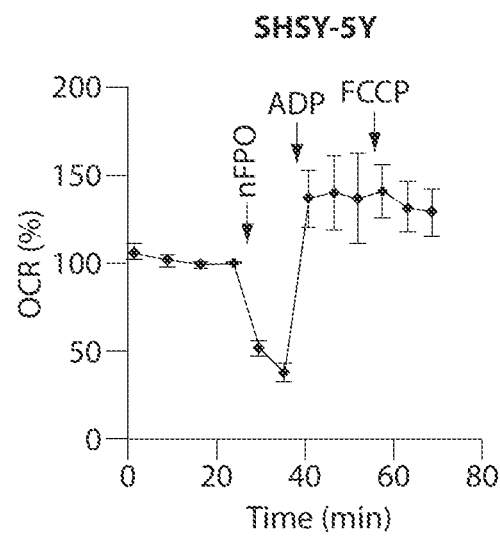
Figure 19F:
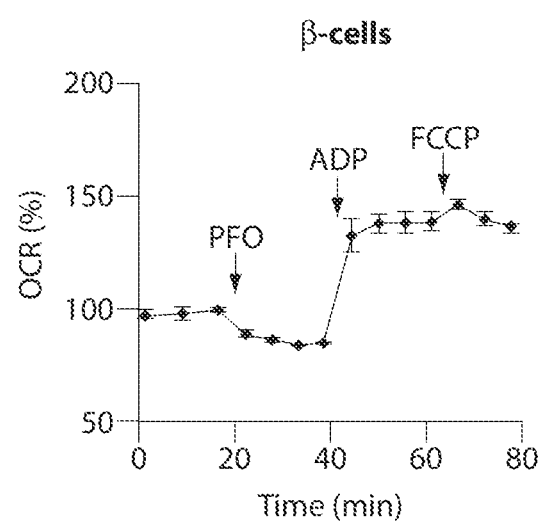

In the presence of substrate respiratory decline in PFO-permeabilized cells is associated with ADP leaking from the cytoplasm, (FIG. 18D, G, H). An alternative assay design was used to determine total OxPhos capacity (FIG. 19D). This permits an analysis of the relationship between OxPhos and respiratory capacities on a given substrate. Experimental conditions, such as the time taken to achieve steady-state respiration rate following PFO-permeabilization may be optimized for a given cell type.

Figure 20A:
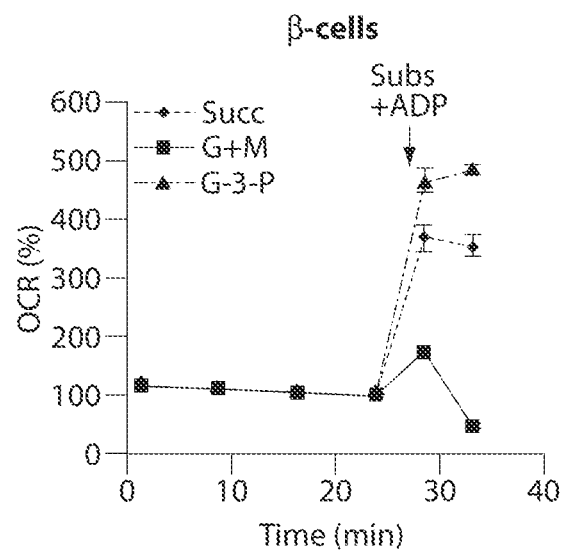
FIGS. 20A-20I show the effects of different factors on OxPhos capacity. Experimental conditions were as described in Example 8 and with reference to FIG. 19. Respiratory substrates (10 mM each) and ADP (1 mM) were either added simultaneously with nPFO (FIGS. 20A, 20B, 20C, 20G, 20H) or afterwards (FIGS. 20E, 20F).
Figure 20B:
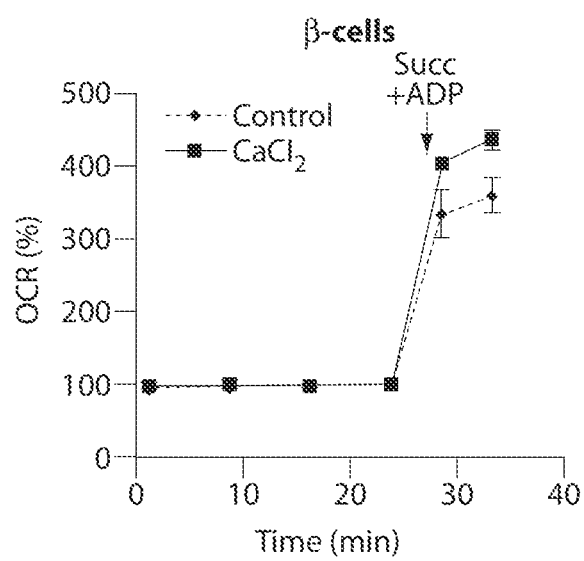

Assessment of OxPhos Capacity Using PFO-Based Assays:

OxPhos capacity can be influenced by certain factors, including, for example, substrate(s) and experimental conditions. Having determined that the PFO-based assay was robust and reproducible, factors that could influence OxPhos capacity were assessed. Spare OxPhos capacity was found to vary with different substrates such as glutamate+malate, succinate, and glycerol-3-phosphate, which support ETC/RC function at Complex I, II and III respectively (FIG. 20A). OxPhos was significantly increased in the presence of free Ca2+ (~220 nM) even with succinate, which oxidation is considered insensitive to Ca2+ (FIG. 20B). Experiments were performed using LKB buffer to facilitate a comparison of mitochondrial bioenergetics in intact and permeabilized cells under the same conditions.

Figure 20C:
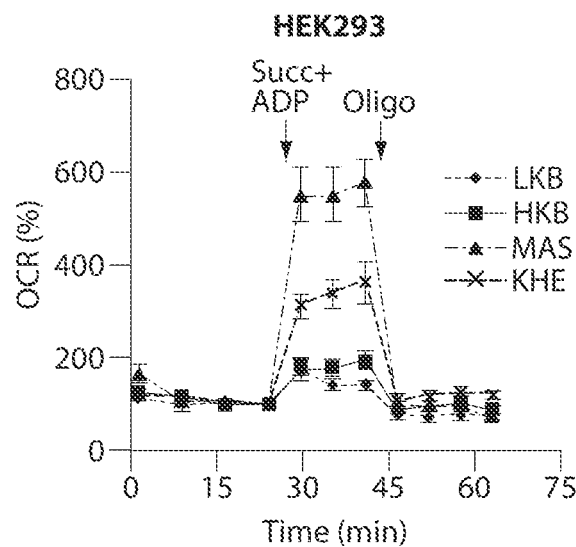
Figure 20D:
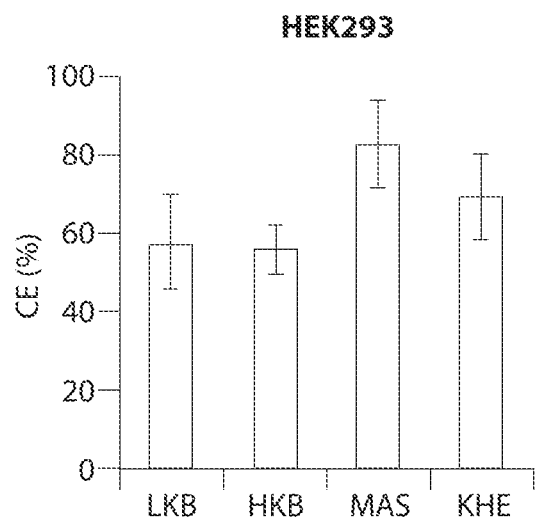

Considering that intracellular K+ concentration is higher in cytoplasm of cells, and PFO-based method is robust and consistent, the extent to which OxPhos capacity was affected by the choice of the respiration medium was evaluated. Table 6 shows a list of respiration buffers that were compared based on effects on OxPhos capacity of HEK293 cells. HEK293 cells were used because they show lower OxPhos capacity than respiratory capacity (FIG. 19A, B). ADP-stimulated respiration was minimal in the LKB buffer. The maximal respiration was observed in MAS buffer (FIG. 20C). Compared to LKB and HKB buffers, the coupling efficiency was significantly higher in the MAS buffer (p<0.05, FIG. 20D).

Figure 20E:
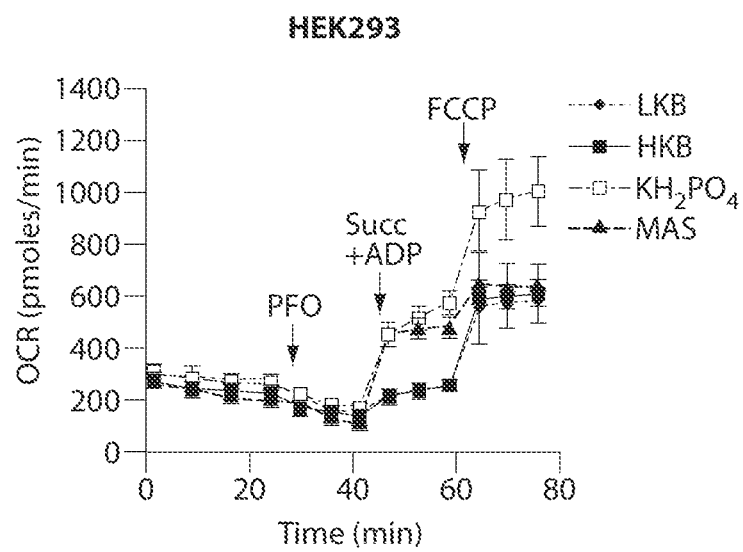

Further analyses indicated that the concentration of $KH_2PO_4$ was a factor that influenced OxPhos capacity (FIG. 20E). Other components of the respiration medium such as BSA (0.2% and 0.4%) and the concentration of buffering agent (e.g. TES or HEPES) had minimal effects on the FCCP-stimulated respiration and did not produce significant effects on ADP-stimulated respiration. When the concentration of $KH_2PO_4$ was increased from 0.4 mM to 10 mM, the spare OxPhos capacity was comparable to that observed in MAS buffer (FIG. 20E). Under these conditions, the OxPhos capacity was lower than the respiratory capacity. These data indicate that, apart from substrate and ADP, Pi availability can limit OxPhos capacity.

Figure 20F:
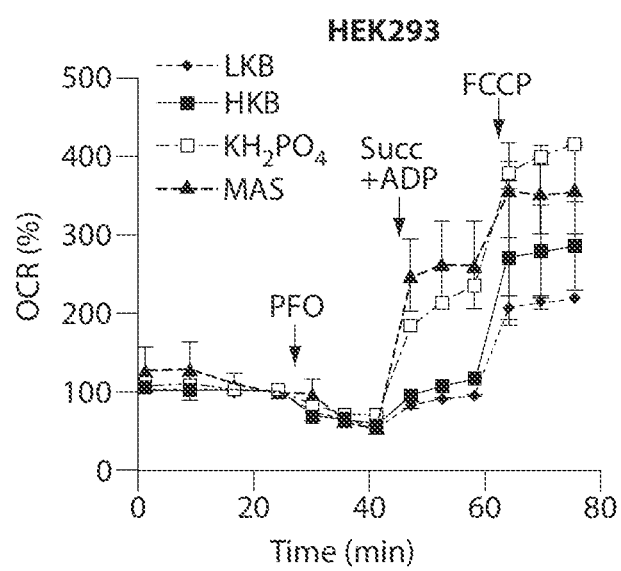
Figure 20G:
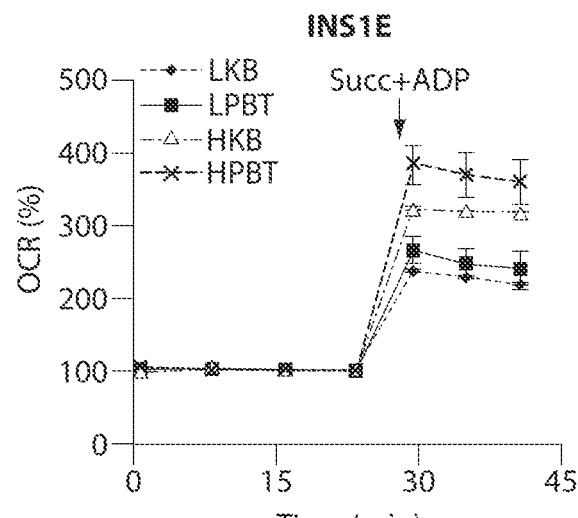
Figure 20H:
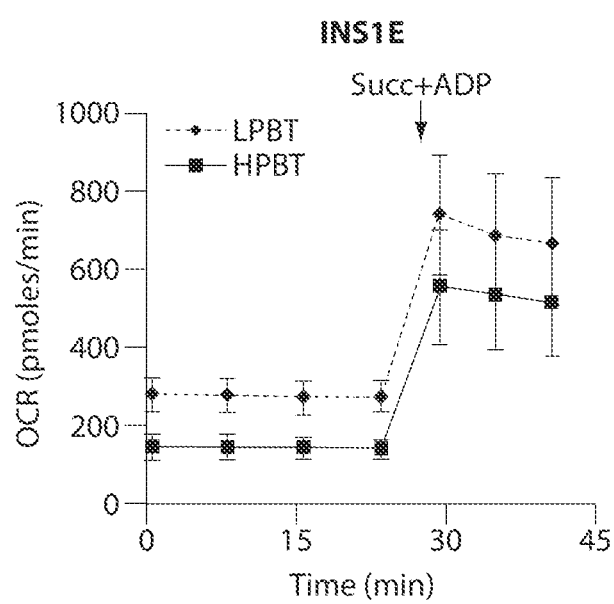
Figure 20I:
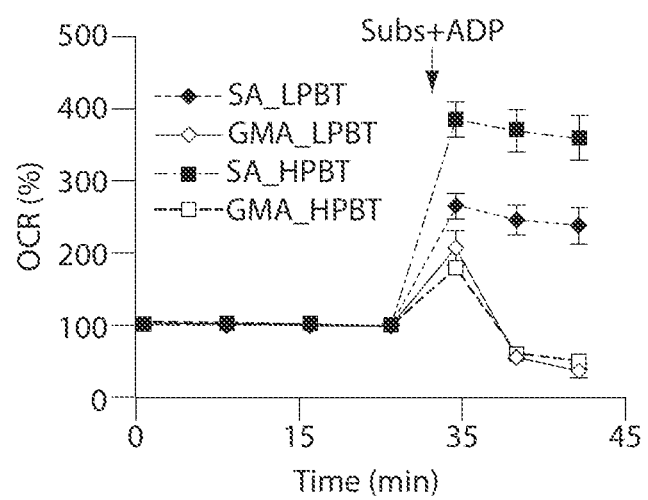

The choice of Na+ vs. K+ buffer may have relatively minor effects on the determination of spare Phos/respiratory capacities in non-excitable cells such as HEK293 (FIG. 20C, E, F) compared to excitable cells such as INS1E (FIG. 20G, H). In INS1E cells, while the spare OxPhos capacity was significantly higher with succinate, a Complex II substrate, significant difference were not observed on Complex I substrates glutamate+malate (FIG. 20I).

Figure 21A:
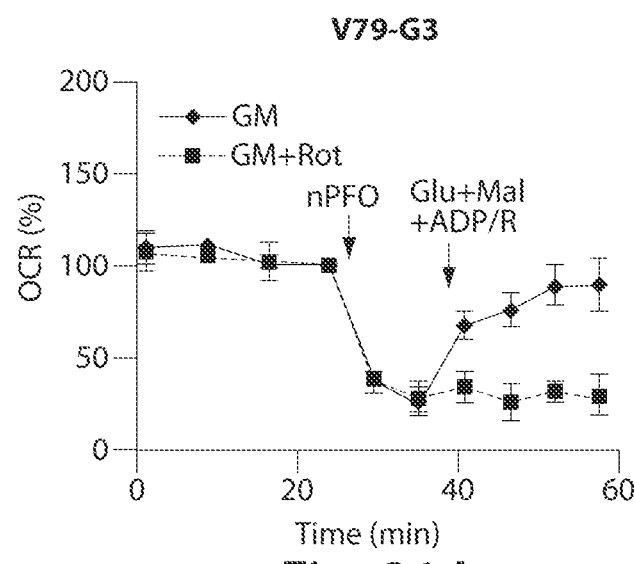
FIGS. 21A-21F show data relating to mitochondrial dysfunction and specific features of mitochondrial metabolism.
Figure 21B:
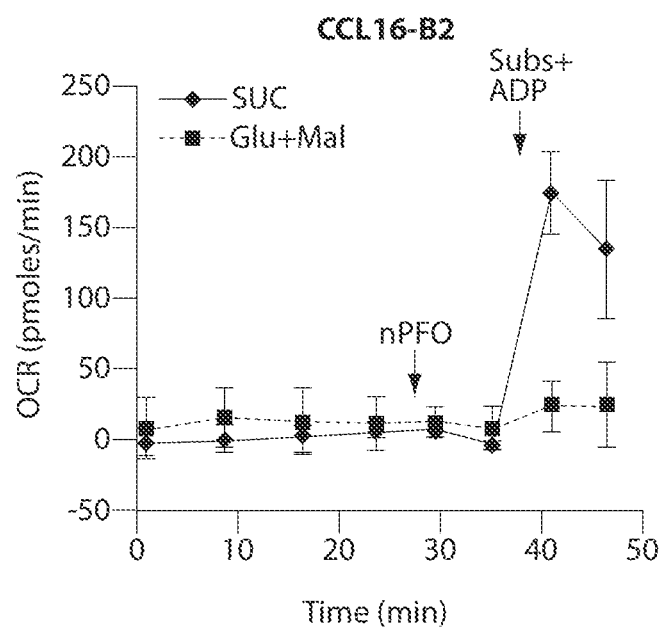
Figure 21C:
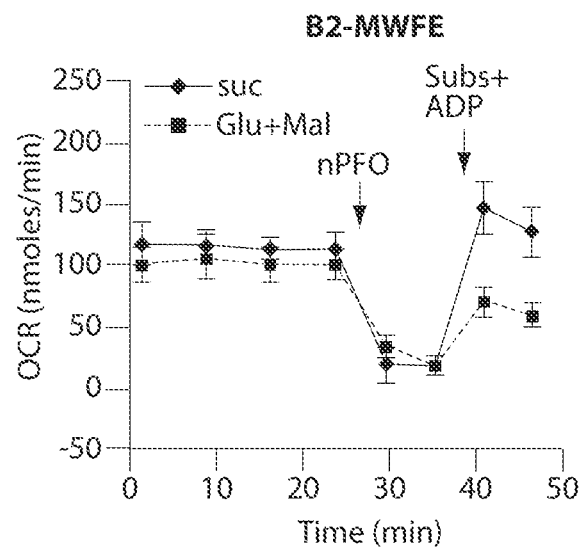

Assessment of ETC/RC Using PFO-Based Assays:

To demonstrate that PFO-based assays can identify specific defects in ETC/RC assembly, Complex I-deficient CCL16-B2 cells were used. The CCL16-B2 cells are impaired in Complex I assembly due to the absence of MWFE subunit encoded by the Ndufa1 gene. First, rotenone sensitivity of glutamate+malate supported respiration was tested in respiration competent V79-G3 cells as shown in FIG. 21A. Glutamate+malate-supported respiration was sensitive to rotenone, a specific inhibitor of Complex I. No glutamate+malate supported respiration was detected in CCL16-B2 cells, while robust respiration was observed using succinate (FIG. 21B). In contrast, B2-MWFE cells, which are CCL16-B2 cells complemented with wild type MWFE protein, showed both glutamate+malate- and succinate-supported respirations under the same conditions (FIG. 21C). These data indicate that, using the PFO-based assays disclosed herein, specific defects in ETC/RC function can be identified using specific substrate and inhibitor combinations from a limited amount of sample, without isolating mitochondria.

Assessing TCA Cycle Metabolism by Respirometry Using PFO-Based Assays:

Since the TCA cycle is the main source of NADH within mitochondria, Complex I-dependent respiration can also provide information about the functional status of individual NADH generating steps, and the factors affecting transport of metabolites into mitochondria. Malate is a TCA cycle metabolite that regulates transport of citrate/isocitrate, α-ketoglutarate and Pi across the mitochondrial inner membrane.

Figure 21D:
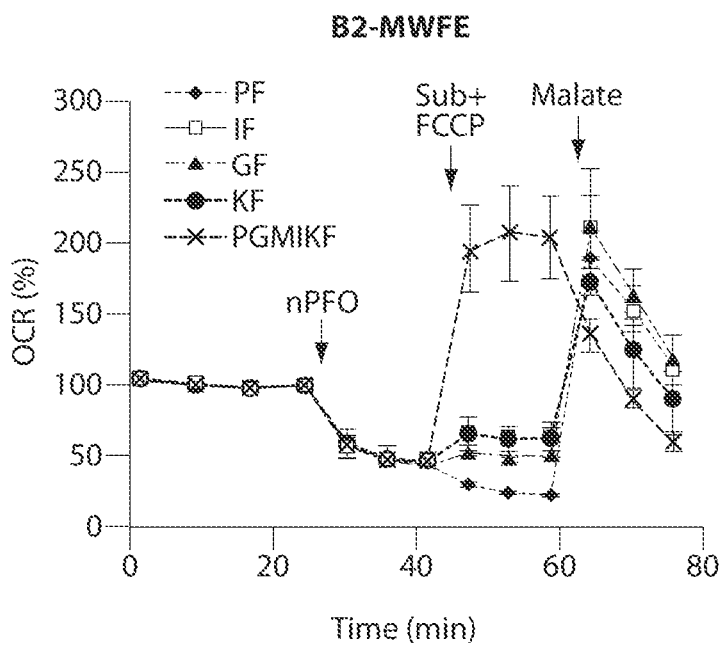

To determine whether and to what extent malate would affect the utilization of pyruvate, isocitrate and α-ketoglutarate to support respiratory activity, respiration rates were measured first in the absence of malate and then in its presence within same assay. This was done in B2-MWFE cells that showed Complex I-dependent respiration (FIG. 21C). Maximal respiratory response with isocitrate and α-ketoglutarate was achieved after addition of malate (FIG. 21D). A similar response was also observed for pyruvate and glutamate, both of which showed even lower respiratory response in the absence of malate. This was unexpected as transport of pyruvate and glutamate is not expected to be directly affected by the presence of malate.

Figure 21E:
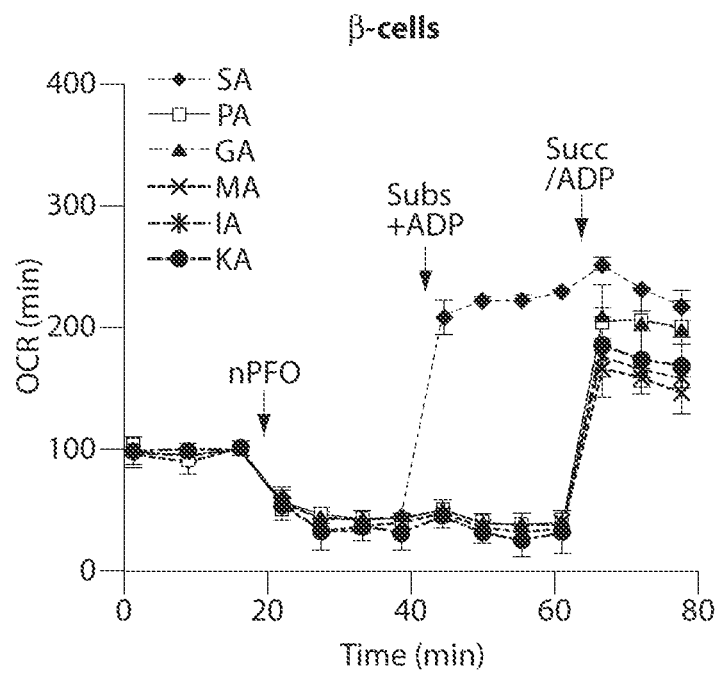

Individually, pyruvate, glutamate, malate, isocitrate and .-ketoglutarate were not observed to support respiration in primary β-cells, while succinate supported respiration was normal in the same cells (FIG. 21E). These data indicate that malate supports maximal respiratory response with NADH generating substrates such as pyruvate, glutamate, isocitrate, and α-ketoglutarate.

Figure 21F:
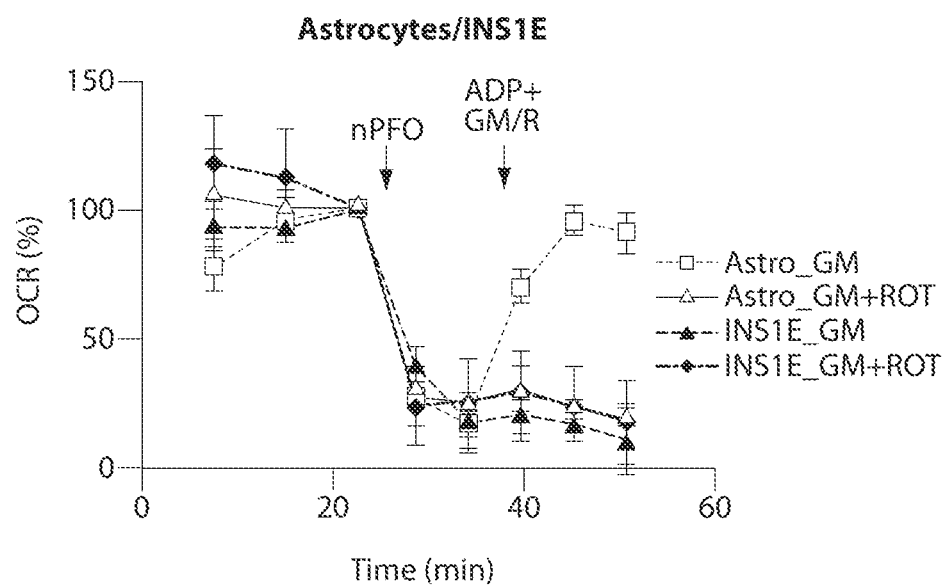

Under conditions that showed Complex I-dependent respiration in primary rat astrocytes, no significant respiration in INS1E was observed (FIG. 21F). This may be due at least in part to β-cell specific negative regulation of NADH metabolism within mitochondria. Such a regulation would permit β cells to rely mostly on cytosolic NADH for their bioenergetic needs in insulin secretion.

When mitochondria were treated with glutamate+malate for 15 min at 37° C. in the presence of 2 μM rotenone to inhibit NADH oxidation, the NAD(P)H level was lower ~40% (4.05±0.65 μM compared with 6.83±0.11 μM, p<0.002 by students t test) in INS1E mitochondria compared to B2-MWFE mitochondria. B2-MWFE cells, whose mitochondria were used as positive controls, show Complex I dependent respiration (FIG. 21C).

Figure 22A:
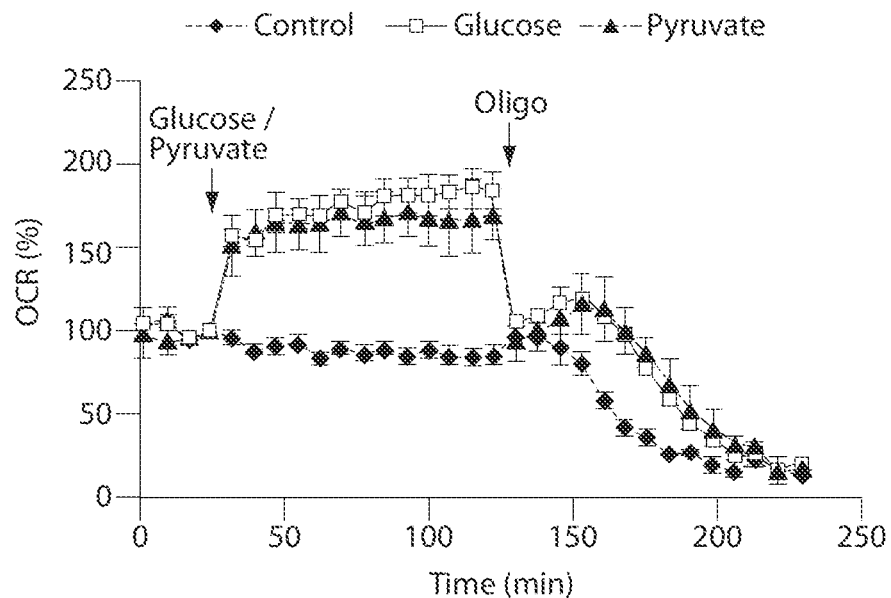
FIGS. 22A-22B show the effects of oligomycin treatment on substrate supply to β cell ETC/RC. INS1E cells were grown and starved as described in the Examples.

Assessment of OxPhos System:

PFO-based assays were used to distinguish the effect of substrate limitations from the direct effects on OxPhos system. INS1E cells, a β-cell model, showed robust glucose-stimulated respiration (FIG. 22A) and progressive respiratory decline when treated with oligomycin (FIG. 22A). The respiratory decline in the presence of oligomycin was observed in both low and high glucose-treated cells (FIG. 22A). These data indicate that in low glucose, respiration is supported by the H+ leak across the inner mitochondrial membrane; whereas in high glucose substantially all glucose-induced respiration supports ATP synthesis (FIG. 22A).

In both cases oligomycin-insensitive respiration declined progressively with time. A faster decline in low glucose medium indicated that substrate supply to ETC/RC could become limiting over time. A similar effect was observed in the presence of pyruvate suggesting that the effect was mostly downstream of glycolysis, and was related to pyruvate metabolism (FIG. 22A).

Figure 22B:
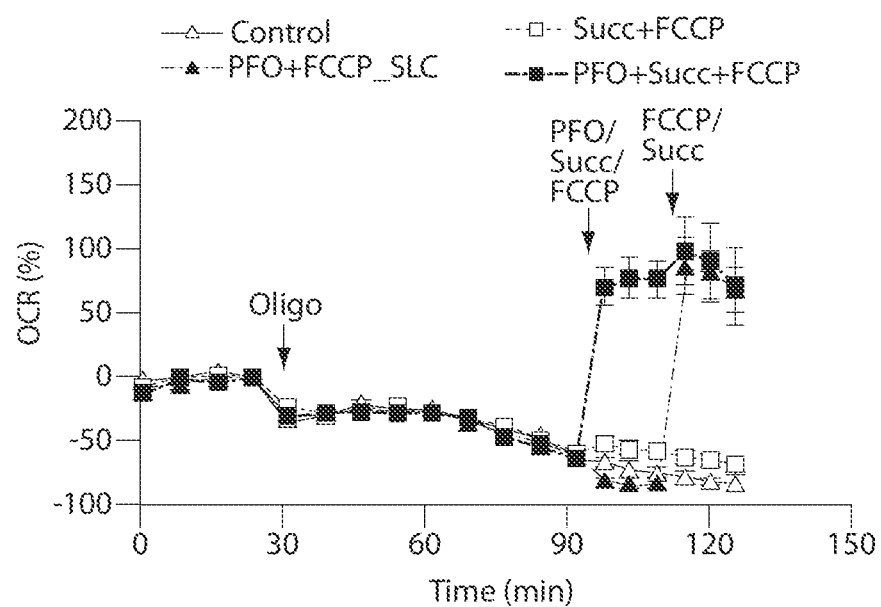

To assess limitations in substrate supply to ETC/RC, respiration rescue experiments were performed in the same cells after permeabilization with nPFO. First INS1E cells were treated with oligomycin in LKB respiration medium (without $CaCl_2$, no EGTA added). Approximately 30 min after oligomycin addition, respiration started to decline gradually (FIG. 22B). When intact cells were treated with FCCP there was no observed increase in respiration. The FCCP could restore respiration only in permeabilized cells when a substrate (succinate) was added. These data indicate that substrate limitation effects a respiratory decline in INS1E cells when OxPhos is completely blocked. This is consistent with the notion that shuttling between mitochondria and cytoplasm of metabolites that influence β cell physiology will be halted in the absence of continuous ATP synthesis. This may result in substrate limitation to the ETC/RC where glycerol-3-phosphate generation by metabolic cycling may be important for β-cell bioenergetics. These experiments illustrate that the PFO-based assays disclosed herein may be used to evaluate direct and indirect effects on ETC/RC function.

Example 9: Analysis of PFO Variants

Figure 27:
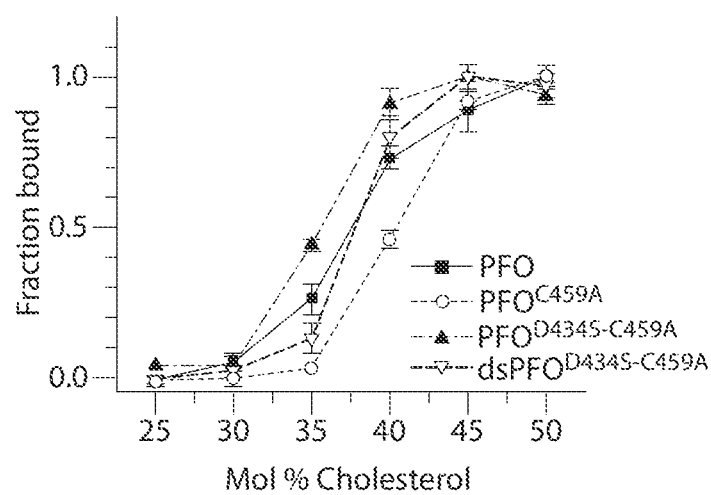
FIG. 27 shows cholesterol-dependence of Cysteine-free PFO derivatives for membrane binding. The fraction of bound PFO derivatives (0.1 μM final concentration) to liposomes of varying cholesterol content and POPC, POPE and SM in a constant 1:1:1 ratio (0.2 mM total lipid final concentration) was determined using intrinsic Trp fluorescence as described in experimental procedures. The cholesterol-dependent binding isotherms for various derivatives: nPFO (PFO) (squares), rPFO (circles), rPFO$^{D434S}$ (upward triangles) and dbPFO$^{D434S-C459A}$ (downward triangles) are shown. Data points are the average of at least two measurements±standard deviation.
Figure 28A:
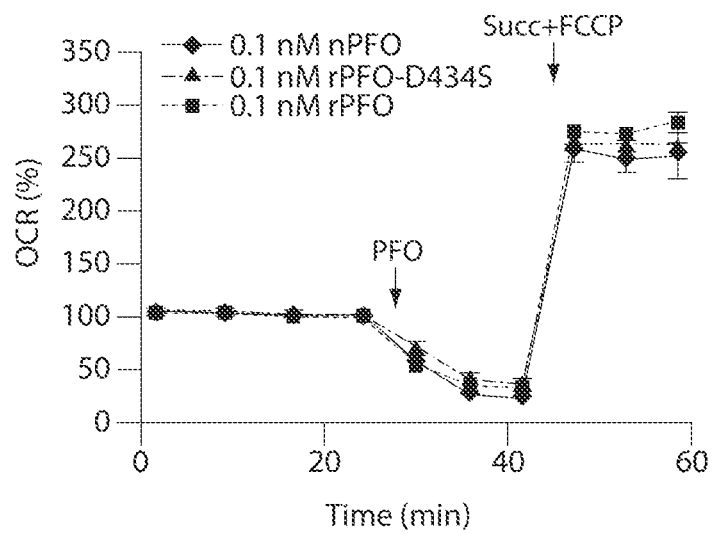
FIGS. 28A-28D show the relative performance of Cysteine-free PFO derivatives in mitochondrial function assays. HEK293 cells were permeabilized using nPFO, rPFO and rPFO$^{D434S}$ (see Table 5) at two different concentrations (0.1, 1.0 nM). Subsequently succinate (Succ: 10 mM) and FCCP (3 mM) were added together to measure maximal respiratory activity.
Figure 28B:
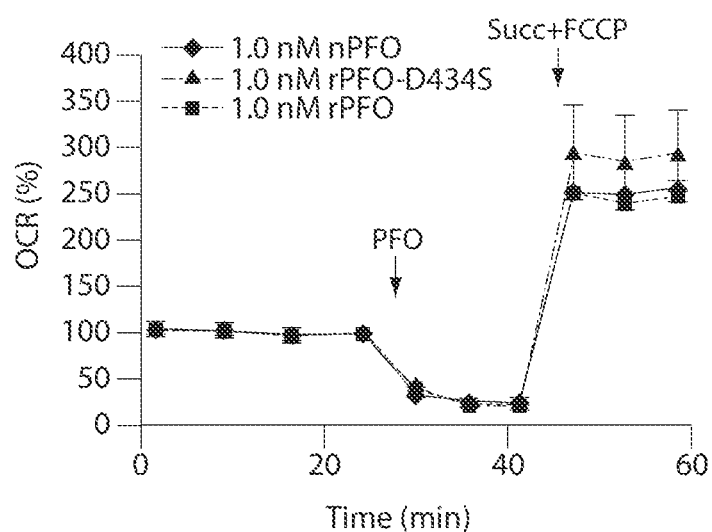
Figure 28C:
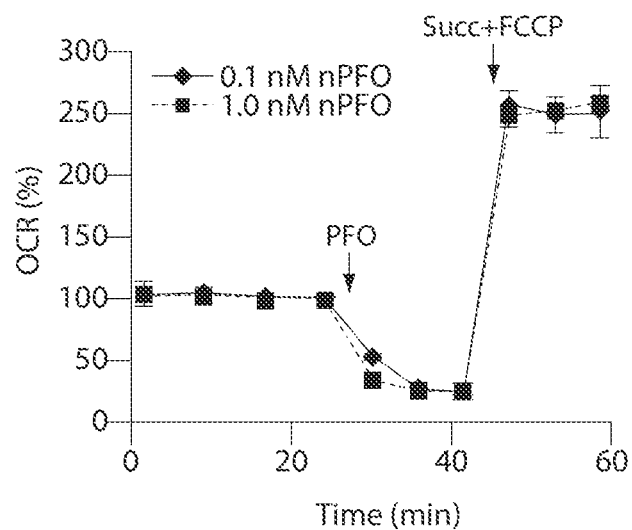
Figure 28D:
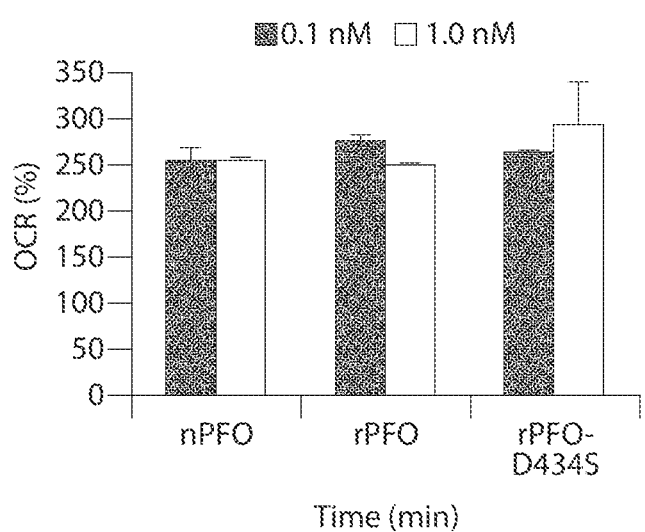
Figure 29A:
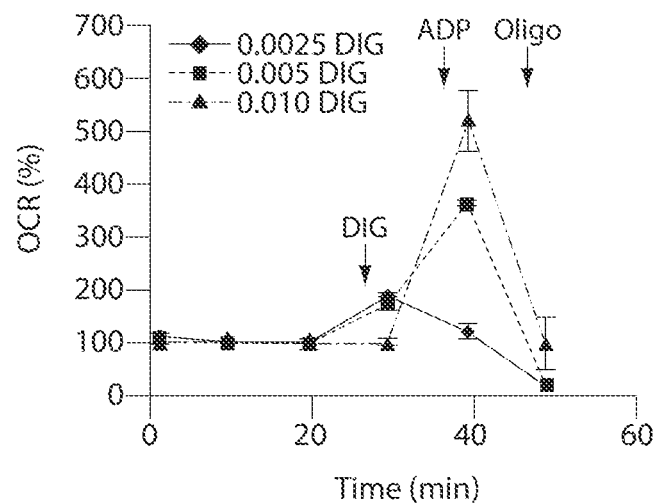
FIGS. 29A-29F show that digitonin mediated cell permeabilization does not give stable respiration. Cells were permeabilized in the presence of different concentrations of digitonin (% DIG) and ADP stimulated respiration using succinate as substrate was monitored. Assays were performed either in LKB or LPBT buffer (see Table 6).
Figure 29B:
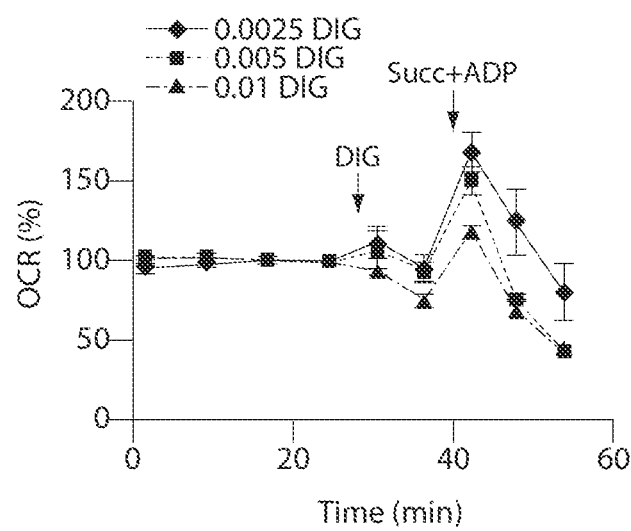
Figure 29C:
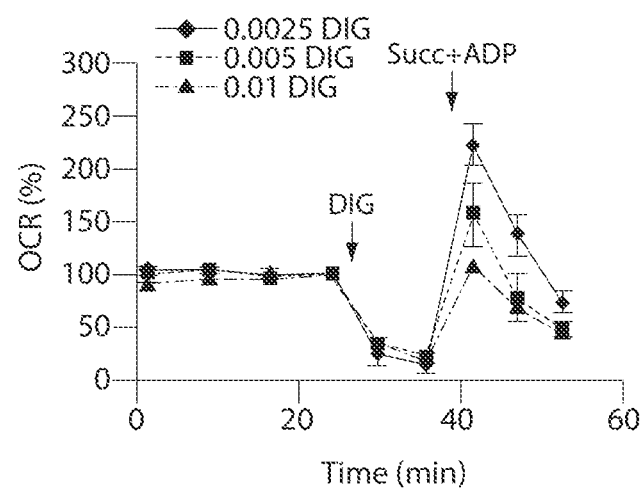
Figure 29D:
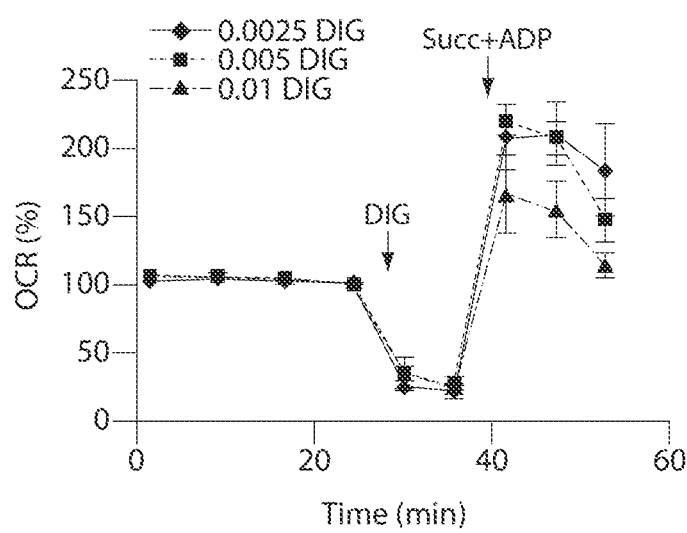
Figure 29E:
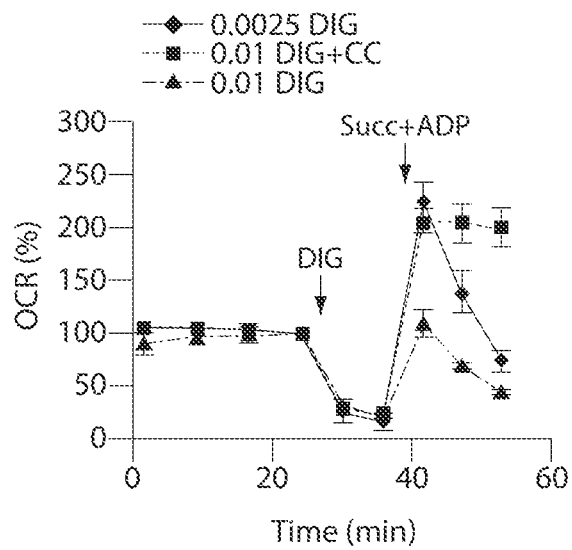
Figure 29F:
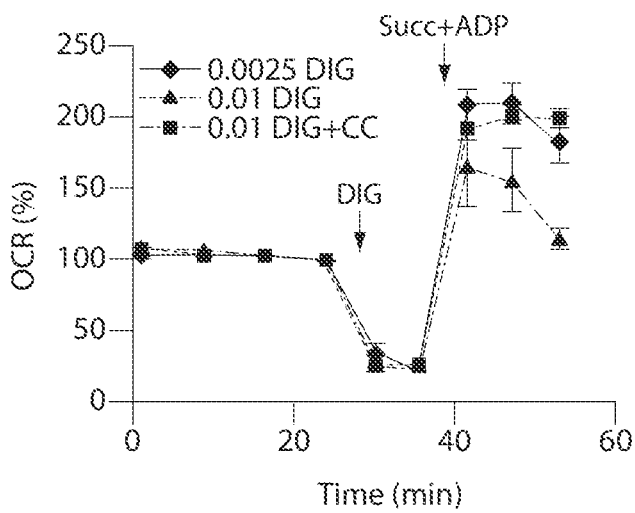

The cholesterol dependent binding of different PFO variants was tested using artificial membranes (liposomes), as shown in FIG. 27. rPFO binding utilized ~4 mol % more cholesterol than the native PFO (nPFO). Introduction of the D434S mutation into the rPFO derivative shifted the membrane binding properties of the mutant protein such that it could be used in the context of similar cholesterol levels as for nPFO. Similarly, when the same mutation was introduced into a PFO derivative containing a disulfide bond (i.e., $rPFO^{T319C-V334C}$) the binding properties of resulting protein $dbPFO^{D434S-C459A}$ were similar to the native PFO. We have therefore restored the cholesterol binding properties of the native toxin in the rPFO and its disulfide bond containing derivative $rPFO^{T319C-V334C}$. These mutants may be used in the absence of reducing agents such as DTT in binding assays to avoid Cys oxidation or disulfide-bond formation between proteins. When using the $rPFO^{T319C-V334C}$ or $dbPFO^{D434S-C459A}$ mutants, the reducing agent may be added after the protein is bound to the target membranes to induce pore formation. Furthermore, the unbound protein may be removed before triggering pore formation using the $rPFO^{T319C-V334C}$ or $dbPFO^{D434S-C459A}$ mutants. The fraction of bound PFO derivatives (0.1 μM final concentration) to liposomes of varying cholesterol content and POPC, POPE and SM in a constant 1:1:1 ratio (0.2 mM total lipid final concentration) was determined using intrinsic Trp fluorescence as described in experimental procedures. The FIG. 27 shows the cholesterol dependent binding isotherms for various derivatives: native PFO (squares), $PFO_{C459A}$ (circles), $PFO^{D434S-C459A}$ (upward triangles) and $PFO^{T319C-V334C-D434S-C459A}$ (or $dbPFO^{D434S-C459A}$, downward triangles). In FIG. 27, data points are the average of at least two measurements and standard deviations.

TABLE 5

PFO variants and their properties:

| PEO derivative | Comments | Pore formation | SEQ ID NO |
|---|---|---|---|
| PFO (nPFO) | Native or wild type protein, utilizes DTT for maintaining activity and storage | Yes | 8 |
| rPFO | Recombinant, Cys less (Cysteine Free) derivative of PFO ($PFO^{C459A}$); it does not require DTT; cholesterol sensitivity is reduced slightly compared to PFO | Yes | 9 |
| $rPFO^{D434S}$ | rPFO with D434S mutation which restores cholesterol sensitivity comparable to that in wild type PFO; it does not require DTT | Yes | 10 |
| $rPFO^{T319C-V334C}$ | Disulfide bond introduced in rPFO by double mutation T319C-V334C; monomeric binding and gets inserted in the membrane; also referred as dbPFO; cholesterol sensitivity lower than PFO | Yes, triggered by DTT | 11 |
| $dbPFO^{D434S-C459A}$ (may be referred to as be $rPFO^{T319C-V334C-D434S}$) | $rPFO^{T319C-V334C}$ with D434S mutation; cholesterol sensitivity comparable to PFO | Yes, triggered by DTT | 12 |

Note:
The amino acid numbering of the substitutions set forth in Tables 3 and 5 are based on the sequence set forth in SEQ ID NO: 1 or 2. Analogous substitutions may be made in PFOs having different sequence lengths. For example, in some embodiments, a PFO may have a truncated N-terminus (e.g., a PFO without an N-terminal signal sequence, e.g., without the first 28 amino acids of SEQ ID NO: 1 or 2) or an extended N-terminus (e.g., a PFO having an N-terminal peptide tag). In such embodiments, the same amino acids may be substituted although the relative position of those amino acids from the N-terminus may be different than in the context of the sequence set forth in SEQ ID NO: 1 or 2.

Preparation of PFO Derivatives.

PFO derivatives were express and purified using appropriate methods known in the art for protein expression and purification. The PFO derivative containing a native PFO sequence (amino acids 29-500 of SEQ ID NO: 2) plus the polyhistidine tag that came from the pRSETB vector (Invitrogen) is named nPFO. The PFO Cys-less derivative (nPFO$^{C459A}$, where Cysteine 459 is replaced by Alanine) is named rPFO. Mutagenesis of PFO was done using the QuickChange (Stratagene) procedure as described previously. Table 5 provides additional information regarding PFO derivatives.

Assay for Binding.

Binding to liposomes was performed using the change in the Trp emission intensity produced by the binding of PFO to cholesterol containing membranes as described previously. Briefly, emission for Trp fluorescence was recorded at 348 nm (4 nm bandpass) with the excitation wavelength fixed at 295 nm (2 nm bandpass). The signal of monomeric PFO derivatives were obtained with samples containing 200 nM protein in buffer A (HEPES 50 mM, NaCl 100 mM, DTT 1 mM, EDTA 0.5 mM, pH 7.5) using 4 mm×4 mm quartz cuvettes. The net emission intensity ($F_0$) for monomers was obtained after subtracting the signal of the sample before the protein was added. Liposomes were added (~200 µM total lipids) and the samples were incubated 20 min at 37° C. Trp emission after membrane incubation was measured after re-equilibration of the sample at 25° C., and the signal from an equivalent sample lacking the protein was subtracted (F). Fraction of protein bound was determined as $(F-F_0)/(F_r-F_0)$, where $F_r$ is the emission intensity when all the protein is bound. Binding of PFO derivatives to cholesterol dispersions in aqueous solutions was done as describe previously.

Preparation of Lipids and Liposomes.

Nonsterol lipids were obtained from Avanti Polar Lipids (Alabaster, Ala.), and cholesterol was from Steraloids (Newport, R.I.). Large unilamellar vesicles were generated as described previously. Briefly, equimolar mixtures of 1-palmitoyl-2-oleoyl-sn-glycero-3-phosphocholine (POPC), 1-palmitoyl-2-oleoyl-sn-glycero-3-phosphoethanolamine (POPE), and sphingomyelin (SM, porcine brain), were combined with the indicated amount of cholesterol (5-cholesten-3β-ol) in chloroform. The thin film of lipids formed after chloroform evaporation was resuspended in buffer A and passed through an extruder equipped with 0.1 µm filter 21 times. Liposomes were stored in ice and discarded after three weeks.

Example 10: PFO Derivatives Show Comparable or Better Performance to Native PFO in Mitochondrial Function Assays Several cysteine-free derivatives of PFO were produced and evaluated. Like native PFO, these derivatives can permeabilize mammalian cells. In some embodiments, it was found that the derivatives can permeabilize cells as efficiently as the native PFO. The cholesterol sensitivity of these derivatives was assessed using liposomes as artificial membranes. Side-by side comparisons of cysteine-free PFO derivatives show comparable or relatively better performance than native PFO.

FIGS. 28A-28D show the relative performance of nPFO, rPFO and rPFO$^{D434S}$ in mitochondrial function assays using human HEK293 cells, rPFO and rPFO$^{D434S}$ were comparable, and maintained their activity in the absence of added reducing agents. A visual inspection under microscope indicated that the overall cellular morphology following permeabilization with rPFO$^{D434S}$ was better preserved compared to other derivatives under the conditions tested. Swelling of cytoplasm/cell ghosts was relatively low after permeabilization with rPFO$^{D434S}$. In some embodiments, therefore, rPFO$^{D434S}$ is advantageous for general use.

In some embodiments, rPFO is advantageous for permeabilization of cells because it has a relatively lower cholesterol sensitivity than other PFO derivatives. For example, cholesterol content in certain mammalian cells may rise under certain pathophysiological conditions (e.g., metabolic syndrome), in such cases cholesterol can accumulate in mitochondria, which may compromise mitochondrial function if the PFO is left in the assay medium. Because rPFO has a relatively low cholesterol sensitivity it may be advantageous for cell permeablization of such cells. Derivatives of PFO that are conditionally active have been developed. In some embodiments, the derivatives of PFO (dbPFO$^{D434S-C459A}$ and rPFO$^{T319C-V334C}$) are triggered to form pores in plasma membranes by ≤50 nM DTT. The use of DTT at concentrations of approximately 50 nM or less does not significantly interfere with cell function when used with these derivatives. These derivatives are useful in cells having high levels of cholesterol. In such cases, removing excess PFO before permeabilization can preserve mitochondrial function after permeabilization. In some embodiments, rPFO$^{T319C-V334C}$ and dbPFO$^{D434S-C459}$ are useful for cell permeabilization because they can be removed before inducing pore formation with ≤50 nM DT. These are concentrations of DTT that are not expected to affect mitochondrial function significantly. In some embodiments, dbPFO$^{D434S-C459A}$ is functionally comparable rPFO$^{T319C-V334C}$.

Example 11: Comparison of PFO Derivatives with Digitonin

Assays for assessing mitochondrial function that utilize digitonin for cell permeabilization are, in some embodiments, limited because (i) observed effects of digitonin on cell permeabilization are concentration dependent, (ii) observed effects of digitonin are influenced by buffer composition, (iii) stable respiration is often not obtained even after careful titration of digitonin, and (iv) observed effects of digitonin have low reproducibility due to limited dynamic range of the digitonin concentration (see FIGS. 29A-29F). In some embodiments, relatively high concentrations of digitonin can damage mitochondrial membranes and release Cytochrome c which is important for respiratory chain function.

As disclosed herein. PFO derivatives overcome these limitations of digitonin. PFO is useful as a permeabilizing agent, in part, because it can be handled with high precision facilitating reliable and reproducible assays. In comparison with digitonin, PFO derivatives produce reproducible results within a concentration range of 0.1-20 nM without significant difference in the experimental output (compare FIGS. 28A-28D and FIGS. 29A-29F). In addition, respiratory activity of cells permeabilized with PFO (in contrast with digitonin) is stable in all the buffers tested (See Example 8).

Choice of Buffers Affects Aspects of Mitochondrial Bioenergetics in Intact and Permeabilized Cells:

Respiratory buffers differing in K+ and inorganic phosphate contents (Pi) (see Table 6) were used to evaluate their impact on mitochondrial function. FIG. 20E-20F shows that buffer choice can affect the oxidative phosphorylation (OxPhos) capacity of cells, which was maximal in MAS buffer.

Figure 30A:
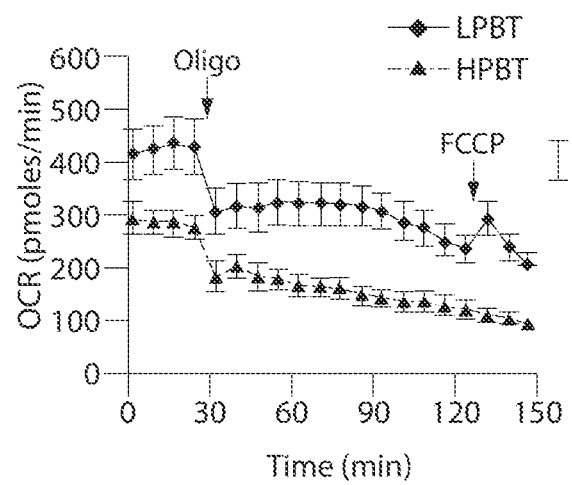
FIGS. 30A and 30B show effects of low K+(LPBT buffer) compared with high K+(HPBT) buffer on INS1E cell bioenergetics.
Figure 30B:
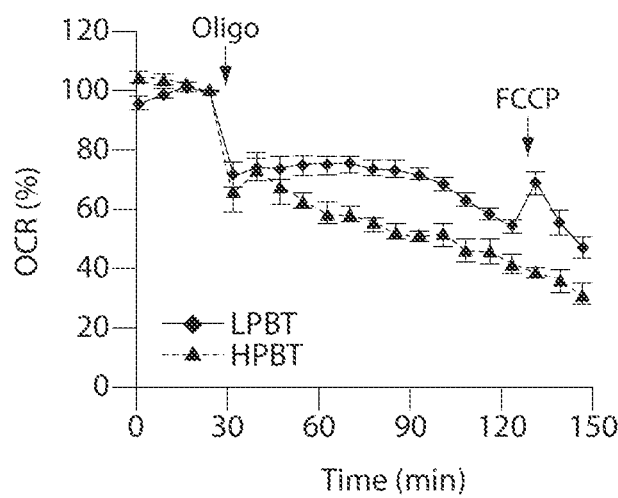

By changing the phosphate (Pi) concentration in LKB from 0.4 mM to 10 mM, the OxPhos capacity in LKB could be increased to the level observed in MAS buffer (FIG. 20E, 20F). Given that different cells (INS1E, and others) look morphologically healthy in low K+ buffers (LKB, LPBT; see Table 6), these buffers have been used in many assays. An example of data showing relatively faster respiratory decline in INS1E cells in the presence of oligomycin (an ATP synthase inhibitor) in HPBT (high K+ buffer) is shown in FIG. 30.

Figure 31A:
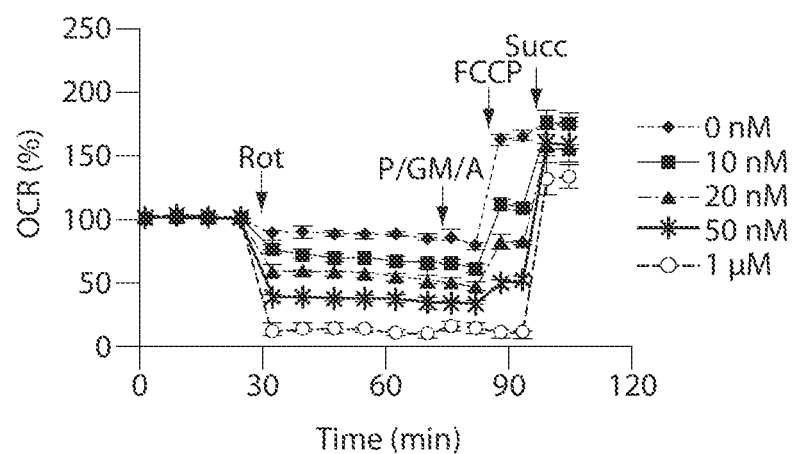
FIGS. 31A-31F show dose-dependent effects of rotenone on overall cellular respiration in intact cells and on Complex I activity in PFO permeabilized cells.
Figure 31B:
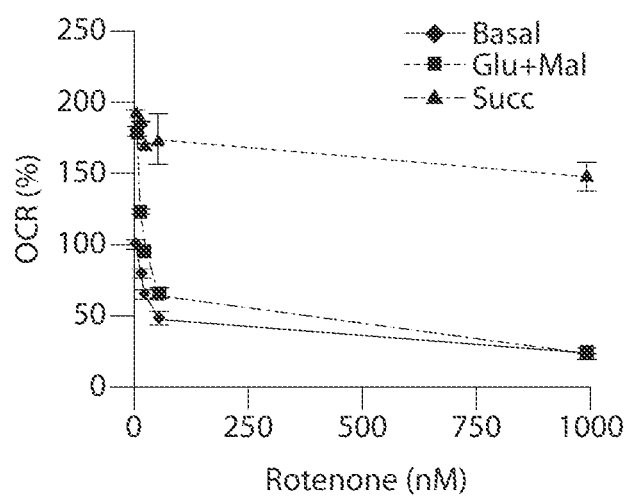
Figure 31C:
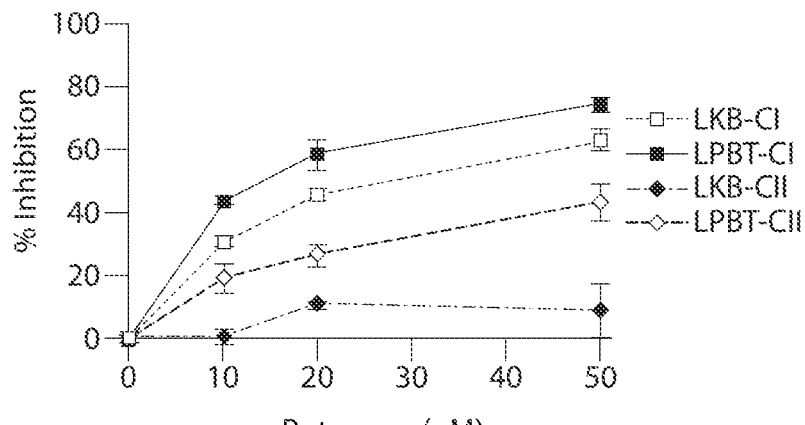
Figure 31D:
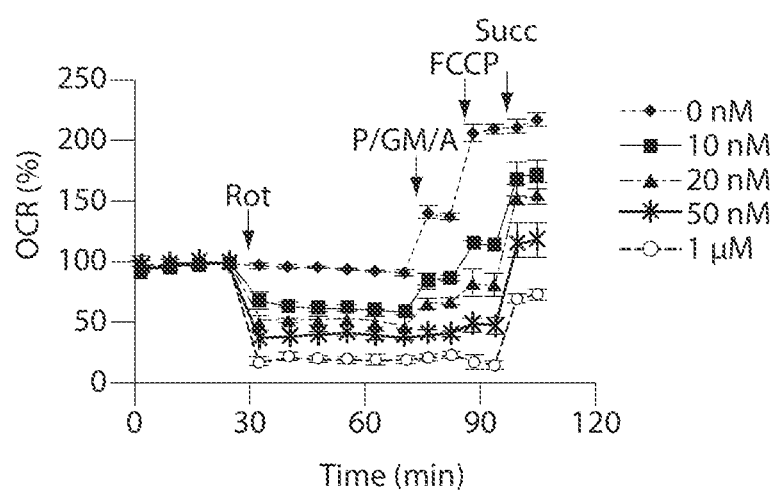
Figure 31E:
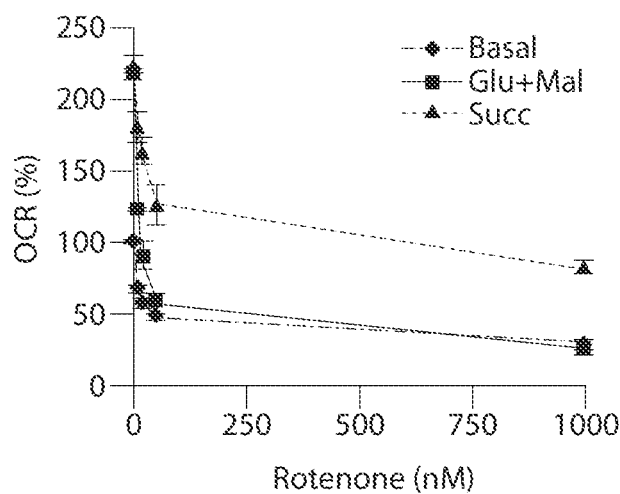
Figure 31F:
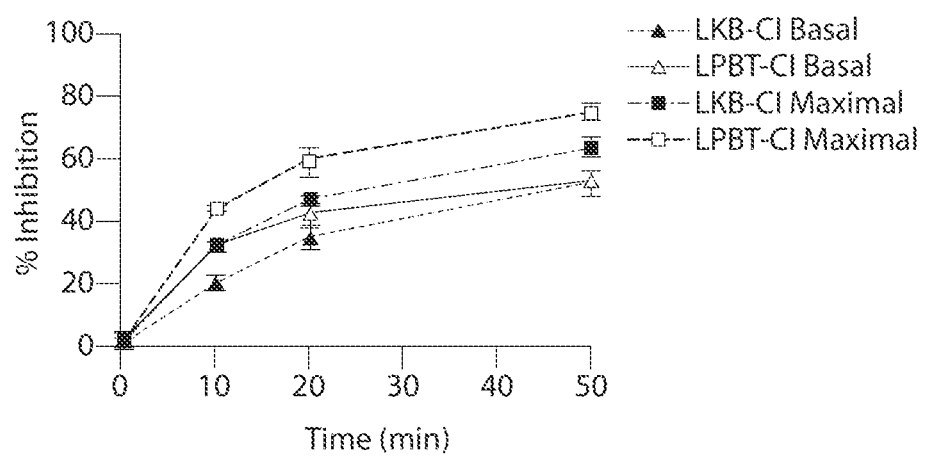

Assessing Respiratory Inhibition in Intact and Permeabilized Cells Simultaneously:

To determine how a drug-induced respiratory inhibition in intact cells translates in to maximal inhibition of a respiratory chain complex, rotenone was used as an example for inhibiting Complex I. FIG. 31A shows the dose-dependent inhibition of the cellular respiration. While in low phosphate LKB buffer (0.4 mM Pi), the ADP-stimulated respiration was not apparent (FIG. 31A), ADP-stimulated respiration was observed in high phosphate LBPT buffer (10 mM Pi). ADP-stimulated respiration was inhibited by rotenone dose-dependently (FIG. 31D). Complex I inhibition was measured in the presence of 3 µM FCCP using the respiration supported by glutamate+malate (FIG. 31A, 31D). It was recognized that with increasing Complex I inhibition by rotenone, Complex II-dependent respiration was also significantly inhibited in LBPT buffer (FIG. 31D, 31E) and was minimal in LKB buffer (FIG. 31A, 31B).

This observation could be due to the build-up of oxaloacetate, which is a physiological inhibitor of Complex II. In the presence of significant Complex I inhibition by the rotenone oxaloacetate may not be converted into citrate due to NADH build up. When Complex II-dependent respiration was measured in rotenone-treated cells in the absence of glutamate+malate, there was no significant Complex II inhibition detected. Thus, Complex II function may be measured in the absence of glutamate+malate when Complex I is significantly inhibited. A higher level of phosphate can also result in succinate exit from mitochondria in exchange for its entry. Thus, maintaining a succinate/phosphate ration >1 for Complex II assay in the presence of Complex I inhibition may be desirable to avoid limitations in succinate supply to Complex II.

Figure 32A:
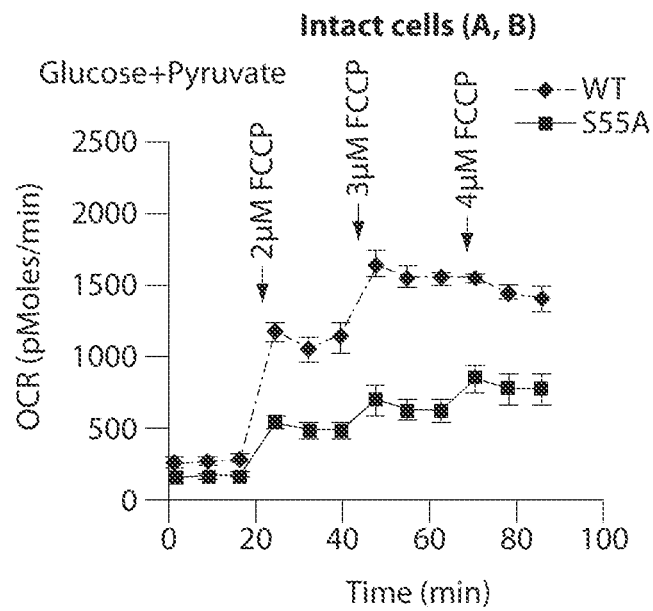
FIGS. 32A-32D show reduced respiratory activity in Ndufa1S55A-derived MEFs.
Figure 32B:
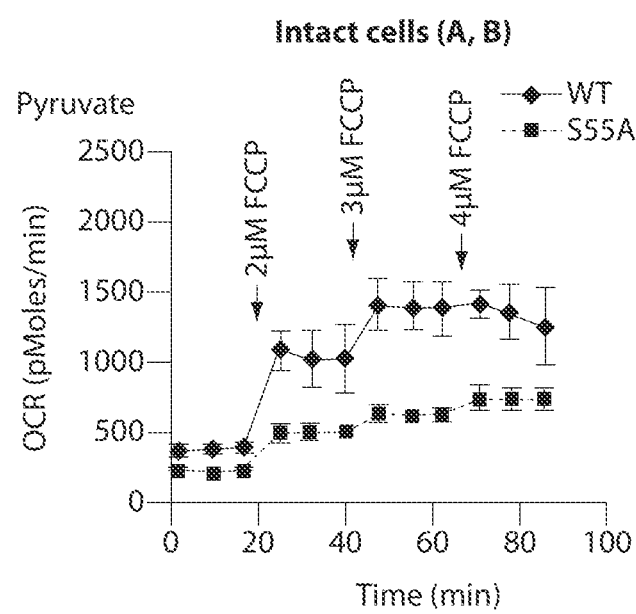
Figure 32C:
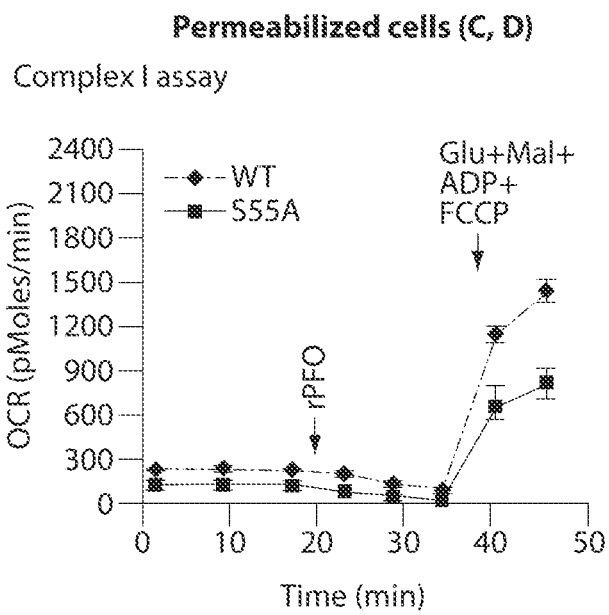
Figure 32D:
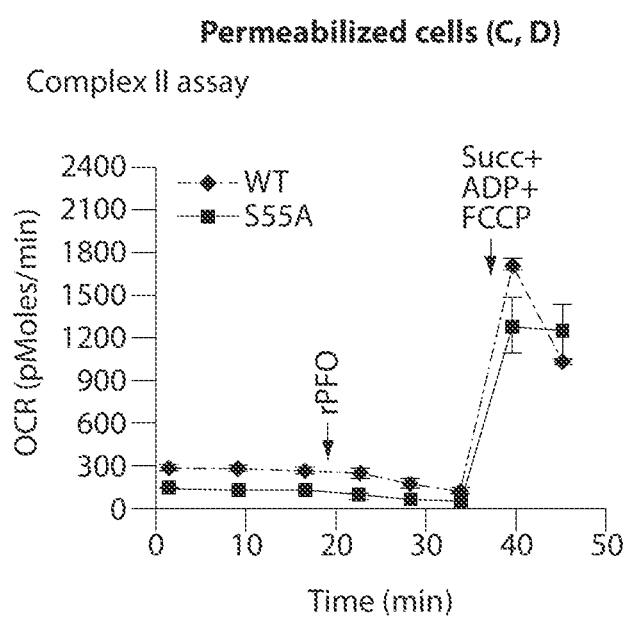

Mouse embryonic fibroblasts (MEFs) derived from a Complex I deficient mouse model (Ndufa1S55A) were used to assess the extent to which genetically encoded partial respiratory chain deficiencies could be detected using PFO-based assays. Intact MEFs from the mutant mice showed reduced cellular respiration on glucose+ pyruvate or pyruvate alone (FIG. 32A, 32B). Observed differences in pyruvate containing respiration buffer confirmed the deficiency in oxidative metabolism, and indicated lack of impaired glycolysis.

In rPFO permeabilized MEFs, there was ~50% reduced Complex I function, while Complex II function was normal. To minimize confounding effects of glutamate+malate in the presence of Complex I deficiency, Complex II function was measured in parallel separately. In summary, these assays provide a framework that can be used for detecting partial respiratory chain deficiencies in human patients with different pathological conditions including mitochondrial diseases.

TABLE 6

Compositions of the respiration buffers. The Ca2+-free buffers contained no added $CaCl_2$, whereas the regular LKB contained 1.3 mM CaCl2 and no added EGTA. Glucose was added at indicated concentrations in the respiration buffers as described in the text and/or figure legends for specific assays.

| Component | LKB[1] | HKB[2] | KHE[3] | MAS[4] | LPBT[5] | HPBT[6] |
|---|---|---|---|---|---|---|
| KCl (mM) | 3.5 | 120 | 115 | | 3.5 | 120 |
| NaCl (mM) | 120 | 3.5 | | | 120 | 3.5 |
| $KH_2PO_4$ (mM) | 0.4 | 0.4 | 10 | 10 | 10 | 10 |
| $Na_2SO_4$ (mM) | 1.2 | 1.2 | | | 1.2 | 1.2 |
| $MgCl_2$ (mM) | 2 | 2 | 2 | 5 | 2 | 2 |
| EGTA (mM) | 1 | 1 | 1 | 1 | 1 | 1 |
| TES (mM)[a] | 20 | 20 | | | 3 | 3 |
| HEPES (mM)[b] | | | 3 | 2 | | |
| Mannitol (mM) | | | | 220 | | |
| Sucrose (mM) | | | | 70 | | |
| BSA (%)c | 0.4 | 0.4 | 0.2 | 0.2 | 0.2 | 0.2 |
| pH | 7.4 | 7.4 | 7.2 | 7.2 | 7.4 | 7.4 |

[a]Na—N-Tris-(hydroxymethyl)-methyl-2-amino-ethanesulphonic acid;
[b]4-(2-hydroxyethyl)-1-piperazineethanesulfonic acid;
cBovine serum albumin (fatty-acid free)
[1]Low K+ buffer;
[2]High K+ buffer;
[3]K+-HEPES-EGTA buffer;
[4]Mannitol and sucrose buffer;
[5,6]Phosphate, BSA and TES concentrations changed in LKB and HKB respectively.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for introducing an exogenous agent into a permeabilized cell comprising:
   (a) incubating a cell with a cholesterol-dependent cytolysin that lacks cysteine residues and that lacks an N-terminal signal sequence, thereby selectively permeabilizing the plasma membrane of the cell; and
   (b) introducing an exogenous agent into the permeabilized cell.

2. The method of claim 1, wherein the exogenous agent is a nucleic acid.

3. The method of claim 1, wherein the exogenous agent is protein.

4. The method of claim 1, wherein the exogenous agent is an antibody.

5. The method of claim 1, wherein the exogenous agent is a dye or fluorescent protein.

6. The method of claim 1, wherein the dye is a calcium sensitive dye or a pH-sensing dye.

7. The method of claim 1, wherein the exogenous agent is a reducing agent, a respiratory chain inhibitor, an oxidative phosphorylation inhibitor, an uncoupling agent, a transport inhibitor, an ionophore or a Krebs cycle inhibitor.

8. The method of claim 1, wherein the exogenous agent is a test agent.

9. The method of claim 1, further comprising measuring the effect of the exogenous agent on the cell.

10. The method of claim 9, wherein said measuring comprises measuring an intracellular function of the cell.

11. The method of claim 10, wherein the intracellular function is a mitochondrial function.

12. The method of claim 1, wherein the cell is a mammalian cell.

13. The method of claim 1, wherein the exogenous agent cannot cross the plasma membrane of a non-permeabilized cell.

14. The method of claim 1, wherein the cholesterol-dependent cytolysin is a variant of a Perfringolysin O (PFO).

15. The method of claim 1, wherein the exogenous agent is a substrate for a mitochondrial enzyme.

\* \* \* \* \*